(12) United States Patent
Preston, III et al.

(10) Patent No.: US 8,119,367 B2
(45) Date of Patent: Feb. 21, 2012

(54) NUCLEIC ACIDS, COMPOSITIONS AND USES THEREOF

(75) Inventors: James F. Preston, III, Micanopy, FL (US); Virginia Chow, Gainesville, FL (US); Guang Nong, Gainesville, FL (US); John D. Rice, Gainesville, FL (US); Franz J. St. John, Baltimore, MD (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 529 days.

(21) Appl. No.: 12/256,155

(22) Filed: Oct. 22, 2008

(65) Prior Publication Data
US 2009/0123981 A1 May 14, 2009

Related U.S. Application Data

(60) Provisional application No. 60/982,623, filed on Oct. 25, 2007, provisional application No. 60/981,599, filed on Oct. 22, 2007.

(51) Int. Cl.
*C12P 13/06* (2006.01)
(52) U.S. Cl. ...................................... 435/69.1
(58) Field of Classification Search ........................ None
See application file for complete search history.

(56) References Cited

U.S. PATENT DOCUMENTS
5,424,202 A 6/1995 Ingram et al.
7,858,353 B2 * 12/2010 Thompson et al. ........... 435/209

OTHER PUBLICATIONS

Preston, J. F. et al. "Microbial strategies for the depolymerization of glucuronoxylan: leads to biotechnological applications of endoxylanases" In S. D. Mansfield and J. N. Sadler (ed.), Applications of enzymes to lignocellulosics, American Chemical Society, Washington D.C., 2003, pp. 191-210.
Nong G. et al. "An aldouronic acid-utilization operon in a *Paenibacillus* sp. encodes an alpha-glucuronidase with activity on aldouronic acids generated by acid and enzyme-mediated digestion of methyglucuronoxylan" Abstracts of the 105th National Meetings of the American Society of Microbiology in Atlanta, GA, 2005, p. 1.
St. John, F.J. et al. "*Paenibacillus* sp. Strain JDR-2 and $XynA_1$: a Novel System for Methylglucuronoxylan Utilization" *Applied and Environmental Microbiology*, Feb. 2006, pp. 1496-1506, vol. 72, No. 2.
Tabernero, C. et al. "Cloning and DNA Sequencing of xyaA, a Gene Encoding an Endoβ-1,4-Xylanase from an Alkalophilic *Bacillus* Strain (N137)" *Applied and Environmental Microbiology*, Jun. 1995, pp. 2420-2424, vol. 61, No. 6.
Takami, H. et al. "Reidentification of Facultatively Alkaliphilic *Bacillus* sp. C-125 to *Bacillus halodurans*" *Biosci. Biotechnol. Biochem.*, 1999, pp. 943-945, vol. 63, No. 5.
Dien, B.S. et al. "Bacteria engineered for fuel ethanol production: current status" *Appl. Microbiol Biotechnol.*, 2003, pp. 258-266, vol. 63.

* cited by examiner

*Primary Examiner* — Hope Robinson
(74) *Attorney, Agent, or Firm* — Saliwanchik, Lloyd & Eisenschenk

(57) ABSTRACT

The subject invention provides at least one nucleic acid sequence encoding an aldouronate-utilization regulon isolated from *Paenibacillus* sp. strain JDR-2, a bacterium which efficiently utilizes xylan and metabolizes aldouronates (methylglucuronoxylosaccharides). The subject invention also provides a means for providing a coordinately regulated process in which xylan depolymerization and product assimilation are coupled in *Paenibacillus* sp. strain JDR-2 to provide a favorable system for the conversion of lignocellulosic biomass to biobased products. Additionally, the nucleic acid sequences encoding the aldouronate-utilization regulon can be used to transform other bacteria to form organisms capable of producing a desired product (e.g., ethanol, 1-butanol, acetoin, 2,3-butanediol, 1,3-propanediol, succinate, lactate, acetate, malate or alanine) from lignocellulosic biomass.

18 Claims, 9 Drawing Sheets

NUCLEIC ACIDS, COMPOSITIONS AND USES THEREOF

CROSS-REFERENCE TO RELATED APPLICATIONS

This application claims the benefit of U.S. Provisional Application Ser. No. 60/981,599, filed Oct. 22, 2007 and U.S. Provisional Application Ser. No. 60/982,623, filed Oct. 25, 2007, the disclosures of which are hereby incorporated by reference in their entirety, including all figures, tables and amino acid or nucleic acid sequences.

The subject invention was made with government support under research projects supported by U.S. Department of Energy grants DE-FG-02GO12026, DE FC36-99GO10476 and DE FC36-00GO10594. The government has certain rights in this invention.

BACKGROUND OF INVENTION

Structural polysaccharides comprise up to 90% of plant cell walls, and include cellulose and hemicellulose fractions as prominent resources renewable through photosynthesis. The hemicellulose fractions constitute from 22 to 30% of the dry weight of lignocellulosic biomass derived from wood and agricultural residues (Kuhad et al., 1997) and the quest for alternatives to petroleum has led to the search and discovery of microorganisms that can serve as biocatalysts for production of fuels and chemical feedstocks from renewable resources.

The major hemicellulose polymer in hardwoods and crop residues is methylglucuronoxylan (MeGAX$_n$), a linear chain of β-1,4-linked D-xylopyranose residues regularly substituted with α-1,2-linked 4-O-methyl-D-glucuronopyranosyl residues. Variable substitutions on xylose residues may include 2'- and 3'-O-acetyl esters, as well as α-1,2- or α-1,3-linked L-arabinofuranosyl residues (Sunna et al., 1997). Additional substituents include O-feruloyl, and O-p-coumaroyl esters linked to hydroxyl groups on the arabinofuranosyl residues.

The natural processing of methylglucuronoxylans is catalyzed by the combined action of endoxylanases, α-glucuronidases, arabinosidases and esterases (Collins et al., 2005; Preston et al., 2003; Sunna et al, 1997). Xylanolytic bacteria secrete endoxylanases of glycohydrolase families GH5, GH10, and GH11 that catalyze the depolymerization of the xylan backbone with the generation of different products (Biely et al., 2000; Preston et al., 2003). The GH10 endoxylanases generate xylobiose, xylotriose, and the aldotetrauronate β-1,4-linked D-xylotriose substituted at the non reducing terminus with α-1,2-linked 4-O-methyl-D-glucuronate. Bacteria that secrete a GH10 endoxylanase may assimilate and metabolize all of the products derived from the depolymerization of MeGAX$_n$. The utilization of the aldouronate requires the expression of genes encoding transporters, α-glucuronidase, and enzymes that convert xylooligosaccahrides to xylose. The glucuronate metabolism gene cluster in Geobacillus stearothermophilus T-6 includes genes that encode required activities, and has been well studied and defined with respect to structural and regulatory genes (Shulami et al., 1999; Shulami et al., 2007). Similar gene clusters have been found in several other bacteria as well (Nelson et al., 1999; Takami et al., 2000).

The isolation and characterization of an aggressively xylanolytic gram-positive endospore-forming bacterium, designated Paenibacillus sp. strain JDR-2, has been reported (St. John et al., 2006). This strain secretes a multimodular GH10 endoxylanase as a cell-anchored protein that catalyzes the depolymerization of MeGAX$_n$ (St. John et al., 2006). The rapid and complete utilization of MeGAX$_n$ without accumulation of the aldotetrauronate, methylglucuronoxylotriose (MeGAX$_3$) in the medium implicated an efficient system for assimilation and complete metabolism of aldouronates. A structural gene, aguA, has been cloned from genomic DNA of Paenibacillus sp. strain JDR-2 and expressed in E. coli with the formation of a recombinant GH67 α-glucuronidase (AguA) that catalyzes conversion of MeGAX$_3$ to methylglucuronate and xylotriose. This gene is followed by xynA2 encoding an intracellular GH10 endoxylanase catalytic domain (XynA2) that processes the xylotriose product generated by the action of AguA on MeGAX$_3$. (Nong et al., 2005).

Both yeast and bacteria have been developed for the bioconversion of glucose derived from the cellulose fraction, and bacteria have been developed for the bioconversion of pentoses, principally xylose, from the hemicellulose fraction (Dien et al., 2003; Ingram et al., 1999; Kuhad et al., 1997). Pretreatment has relied on a combination of chemical and enzymatic hydrolytic procedures to solubilize the hemicellulose fraction and release fermentable xylose, and to depolymerize the cellulose to fermentable glucose. Pretreatment protocols are still being developed to provide cost-effective production of ethanol and other biobased products from these resources (Lloyd et al., 2005).

BRIEF SUMMARY

The subject invention provides at least one nucleic acid sequence encoding an aldouronate-utilization regulon isolated from Paenibacillus sp. strain JDR-2, a bacterium which efficiently utilizes xylan and metabolizes aldouronates (methylglucuronoxylosaccharides). The subject invention also provides a means for providing a coordinately regulated process in which xylan depolymerization and product assimilation are coupled in Paenibacillus sp. strain JDR-2 to provide a favorable system for the conversion of lignocellulosic biomass to biobased products. Additionally, the nucleic acid sequences encoding the aldouronate-utilization regulon can be used to transform other bacteria to form organisms capable of producing a desired product from lignocellulosic biomass.

BRIEF DESCRIPTION OF THE FIGURES

FIG. 5A: Growth was determined as turbidity (OD$_{600}$) for MeGAX$_n$ (open circles), MeGAX$_1$ (open triangles), and MeGAX$_3$ (open squares); and for MeGAX$_n$ as cell protein (closed circles). FIG. 5B: Utilization of substrates was determined by total carbohydrate assay for MeGAX$_n$ (open circles), MeGAX$_1$ (open triangles), and MeGAX$_3$ (open squares); and determined by uronic acid assay for MeGAX$_n$ (closed circles). Data points are the average values obtained for replicate samples; bars denote the range.

FIG. 9A. MeGAX$_1$ control (peak: 9.06 min); FIG. 9B. MeGAX$_1$ (peak: 9.06 min) cleaved into MeGA (peak: 10.29 min) and xylose (peak: 12.12 min) by AguA for 30 min; FIG. 9C. MeGAX$_3$ (peak: 8.12 min) control; FIG. 9D: MeGAX$_3$ (peak: 8.12 min) cleaved into xylotriose (peak: 8.75 min) and MeGA (peak: 10.29 min) by AguA for 30 min.

BRIEF DESCRIPTION OF THE SEQUENCES

SEQ ID NO:1 and SEQ ID NO:2 are the polynucleotide and polypeptide sequences, respectively, encoding the yesN CheY-like, Ara C type response regulator.

SEQ ID NO:3 and SEQ ID NO:4 are the polynucleotide and polypeptide sequences, respectively, encoding the yesM Histidine kinase-type transduction protein.

SEQ ID NO:5 and SEQ ID NO:6 are the polynucleotide and polypeptide sequences, respectively, encoding the lplA Substrate binding protein.

SEQ ID NO:7 and SEQ ID NO:8 are the polynucleotide and polypeptide sequences, respectively, encoding the lplB Lipoprotein.

SEQ ID NO:9 and SEQ ID NO:10 are the polynucleotide and polypeptide sequences, respectively, encoding the ytcP Permease activity.

SEQ ID NO:11 and SEQ ID NO:12 are the polynucleotide and polypeptide sequences, respectively, encoding the aguA GH67 α-glucuronidase activity.

SEQ ID NO:13 and SEQ ID NO:14 are the polynucleotide and polypeptide sequences, respectively, encoding the xynA2 GH10 xylanase activity.

SEQ ID NO:15 and SEQ ID NO:16 are the polynucleotide and polypeptide sequences, respectively, encoding the xynB GH43 β-xylosidase activity.

SEQ ID NO:17 and SEQ ID NO:18 are the polynucleotide and polypeptide sequences encoding a NADH-dependent flavin oxidoreductase.

SEQ ID NO:19 and SEQ ID NO:20 are the polynucleotide and polypeptide sequences for the xynA1 gene.

Figure 1:
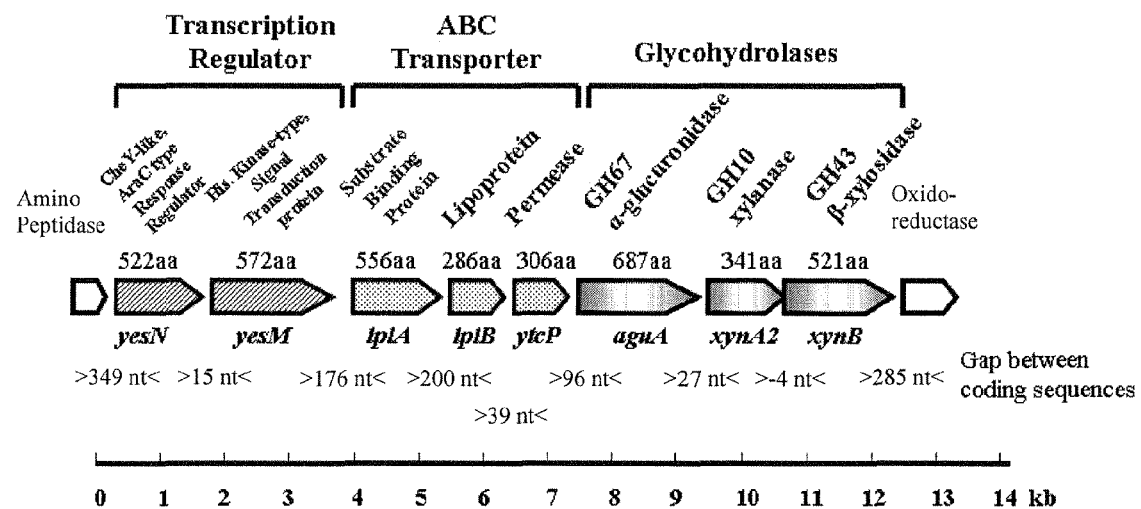
FIG. 1 depicts the genomic organization of aldouronate-utilization operons in Paenibacillus sp. JDR-2. More recent analysis has made changes in the annotation of the polypeptide lengths of lplA (570 aa instead of 556 aa) and lplB (323 aa instead of 286 aa). The intergenic distances between yesM and lplA should be 134 nt and between lplA and lplB should be 89 nt.

SEQ ID NO:21 is a sequence of 15276 base pairs (bps) that includes the genes identified in FIG. 1 and Table 4. This sequence has been deposited with GenBank as EU024644, which is hereby incorporated by reference in its entirety.

SEQ ID NOs:22-49 are primer sequences.

SEQ ID NOs:50-55 are candidate CcpA binding sites.

DETAILED DISCLOSURE

The subject invention pertains to the genetic transformation of known host cells (e.g., Gram positive or Gram negative ethanogenic bacteria) so as to provide these bacteria with the ability to produce ethanol from lignocellulosic biomass or xylan containing substrates. Thus, the subject invention allows the use of recombinant strains of yeast, Gram positive and/or Gram negative bacteria for the production of ethanol from under-utilized sources of biomass, such as hemicellulose (a major portion of wood and inedible plant parts). Thus, in one aspect of the subject invention yeast, Gram negative and/or Gram positive organisms are transformed with one or more of the disclosed nucleic acid sequences encoding the aldouronate-utilization regulon. The organisms that are transformed may, or may not, contain a naturally occurring aldouronate-utilization regulon. In some embodiments, the transformed organism lacks a naturally occurring aldouronate-utilization regulon.

Another aspect of the invention provides for the co-culture of a host cell (e.g., a yeast, Gram positive or Gram negative bacteria) comprising one or more of the nucleic acid sequences encoding the aldouronate-utilization regulon with another organism that produces a desired product. The organism containing one or more of the nucleic acid sequences encoding the aldouronate-utilization regulon is used to breakdown complex lignocellulosic biomass or xylan containing substrates into a form that the bacteria producing a desired product can utilize (e.g., xylose). In certain aspects of the invention, thermotolerant host cells are preferred (e.g., thermotolerant *Bacillus* spp. (e.g., thermotolerant *B. coagulans*).

As defined herein, a "desired product" or "product of interest" can be any product/compound that can be produced by a host cell. Thus, non-limiting examples of a "desired product" or "product of interest" include ethanol, 1-butanol, acetoin, 2,3-butanediol, 1,3-propanediol, succinate, lactate, acetate, malate, or alanine.

To impart to a microorganism the ability to produce one or more of the elements of the aldouronate-utilization regulon disclosed herein, a single nucleic acid comprising all of the elements (e.g., SEQ ID NOs: 1, 3, 5, 7, 9, 11, 13, 15 and 17 [or SEQ ID NO: 21 which encodes the entire regulon]) of the aldouronate-utilization regulon can be provided to a bacterial cell via transformation or any other means (e.g., chromosomal integration). These elements may be used for the direct utilization of aldouronates generated by the chemical and/or enzymatic digestion of the hemicellulose fraction of lignocellulosics. These elements may also be used to construct an expanded cassette to include secreted endoxylanases containing catalytic domains, with and without modular substrate binding domains, for the purpose of depolymerization and direct utilization of fermentable constituents. Constructs may also be generated to include genes encoding enzymes tolerant of acidic conditions (low pH) and high temperatures (greater than 50° C.). Thus, this single nucleic acid can be in the form of a transposon element, genetic construct or a vector, such as a plasmid. Alternatively, individual nucleic acids (e.g., genes) encoding polypeptides of the aldouronate-utilization regulon can be used to transform bacteria. Thus, a single nucleic acid molecule according to the subject invention can contain one or any combination of 2, 3, 4, 5, 6 7, 8 or 9 genes encoding the polypeptides of the aldouronate-utilization regulon. Again, the individual nucleic acids encoding polypeptides of the aldouronate-utilization regulon can be incorporated into a plasmid or other genetic construct which is used to transform a host organism.

As set forth herein, the subject application provides isolated, recombinant, and/or purified polynucleotide sequences comprising:

a) a polynucleotide sequence encoding a polypeptide as set forth in SEQ ID NOs: 2, 4, 6, 8, 10, 12, 14, 16, 18 or 20;

b) a polynucleotide sequence having at least about 20% to 99.99% identity to a polynucleotide sequence encoding a polypeptide as set forth in SEQ ID NOs: 2, 4, 6, 8, 10, 12, 14, 16, 18 or 20, wherein said polynucleotide encodes a polypeptide having at least one of the activities of SEQ ID NOs: as set forth in SEQ ID NOs: 2, 4, 6, 8, 10, 12, 14, 16, 18 or 20;

c) a polynucleotide sequence comprising SEQ ID NO: 1, 3, 5, 7, 9, 11, 13, 15, 17, 19 or 21;

d) a polynucleotide sequence having at least about 20% to 99.99% identity to the polynucleotide sequence of SEQ ID NO: 1, 3, 5, 7, 9, 11, 13, 15, 17, 19 or 21;

e) a polynucleotide that is complementary to the polynucleotides set forth in (a), (b), (c), or (d);

f) a genetic construct comprising a polynucleotide sequence as set forth in (a), (b), (c), (d), or (e);

g) a vector comprising a polynucleotide or genetic construct as set forth in (a), (b), (c), (d), (e), or (f);

h) a host cell comprising a vector as set forth in (g), a genetic construct according to (f) or a polynucleotide as set forth in any of (a)-(e);

i) a polynucleotide that hybridizes under low, intermediate or high stringency with a polynucleotide sequence as set forth in (a), (b), (c), (d) or (e);

j) a probe comprising a polynucleotide according to (a), (b), (c), (d) or (e) and, optionally, a label or marker; or k) a host cell as set forth in (h), wherein said host cell is selected from *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acelophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azoloformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus coagulans, Escherichia freundii, Microbacterium ammoniaphilum, Serratia marcescens, Salmonella typhimurium, Salmonella schottinulleri, Xanthomonas citri, Thermotoga martima, Geobacillus sterothermophilus* and so forth (in certain embodiments, thermotolerant microorganisms, such as a thermotolerant *B. coagulans* strain are preferred).

"Nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules). It should also be understood that the present invention does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, subcloning or chemical synthesis, or combinations of these genetic engineering methods.

A homologous polynucleotide or polypeptide sequence, for the purposes of the present invention, encompasses a sequence having a percentage identity with the polynucleotide or polypeptide sequences, set forth herein, of between at least (or at least about) 20.00% to 99.99% (inclusive). The aforementioned range of percent identity is to be taken as including, and providing written description and support for, any fractional percentage, in intervals of 0.01%, between 20.00% and including 99.99%. These percentages are purely statistical and differences between two nucleic acid sequences can be distributed randomly and over the entire sequence length. For example, homologous sequences can exhibit a percent identity of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent with the sequences of the instant invention. Typically, the percent identity is calculated with reference to the full length, native, and/or naturally occurring polynucleotide (e.g., any one of SEQ ID NOs: 1, 3, 5, 7, 9, 11, 13, 15, 17, 19 or 21). The terms "identical" or percent "identity", in the context of two or more polynucleotide or polypeptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson et al., 1988; Altschul et al., 1990; Thompson et al., 1994; Higgins et al., 1996; Gish et al., 1993). Sequence comparisons are, typically, conducted using default parameters provided by the vendor or using those parameters set forth in the above-identified references, which are hereby incorporated by reference in their entireties.

A "complementary" polynucleotide sequence, as used herein, generally refers to a sequence arising from the hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. A "complementary" polynucleotide sequence may also be referred to as an "antisense" polynucleotide sequence or an "antisense sequence".

Sequence homology and sequence identity can also be determined by hybridization studies under high stringency, intermediate stringency, and/or low stringency. Various degrees of stringency of hybridization can be employed. The more severe the conditions are, the greater the complementarity that is required for duplex formation. Severity of conditions can be controlled by temperature, probe concentration, probe length, ionic strength, time, and the like. Preferably, hybridization is conducted under low, intermediate, or high stringency conditions by techniques well known in the art, as described, for example, in Keller and Manak (1987).

For example, hybridization of immobilized DNA on Southern blots with $^{32}$P-labeled gene-specific probes can be performed by standard methods (Maniatis et al., 1982). In general, hybridization and subsequent washes can be carried out under intermediate to high stringency conditions that allow for detection of target sequences with homology to the exemplified polynucleotide sequence. For double-stranded DNA gene probes, hybridization can be carried out overnight at 20-25° C. below the melting temperature ($T_m$) of the DNA hybrid in 6×SSPE, 5×Denhardt's solution, 0.1% SDS, 0.1 mg/ml denatured DNA. The melting temperature is described by the following formula (Beltz et al., 1983).

$Tm=81.5°$ C.+16.6 Log [Na$^+$]+0.41 (% G+C)−0.61 (% formamide)−600/length of duplex in base pairs.

Washes are typically carried out as follows:
(1) twice at room temperature for 15 minutes in 1×SSPE, 0.1% SDS (low stringency wash);
(2) once at $T_m$−20° C. for 15 minutes in 0.2×SSPE, 0.1% SDS (intermediate stringency wash).

For oligonucleotide probes, hybridization can be carried out overnight at 10-20° C. below the melting temperature ($T_m$) of the hybrid in 6×SSPE, 5×Denhardt's solution, 0.1% SDS, 0.1 mg/ml denatured DNA. $T_m$ for oligonucleotide probes can be determined by the following formula:

$T_m$(° C.)=2(number T/A base pairs)+4(number G/C base pairs) (Suggs et al., 1981).

Washes can be carried out as follows:
(1) twice at room temperature for 15 minutes 1×SSPE, 0.1% SDS (low stringency wash);
2) once at the hybridization temperature for 15 minutes in 1×SSPE, 0.1% SDS (intermediate stringency wash).

In general, salt and/or temperature can be altered to change stringency. With a labeled DNA fragment >70 or so bases in length, the following conditions can be used:

| Low: | 1 or 2X SSPE, room temperature |
| Low: | 1 or 2X SSPE, 42° C. |
| Intermediate: | 0.2X or 1X SSPE, 65° C. |
| High: | 0.1X SSPE, 65° C. |

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in pre-hybridization mixture containing 100 µg/ml denatured salmon sperm DNA and 5–20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al. (1989) and Ausubel et al. (1989) are incorporated herein in their entirety.

Another non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art and as cited in Sambrook et al. (1989) and Ausubel et al. (1989) are incorporated herein in their entirety.

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. (1982); Wei et al. (1983).

The present invention further comprises fragments of the polynucleotide sequences of the instant invention. Representative fragments of the polynucleotide sequences according to the invention will be understood to mean any nucleotide fragment having at least 5 successive nucleotides, preferably at least 12 successive nucleotides, and still more preferably at least 15, 18, or at least 20 successive nucleotides of the sequence from which it is derived. The upper limit for such fragments is the total number of nucleotides found in the full-length sequence encoding a particular polypeptide (e.g., a polypeptide such as that of SEQ ID NO: 2). The term "successive" can be interchanged with the term "consecutive" or the phrase "contiguous span". Thus, in some embodiments, a polynucleotide fragment may be referred to as "a contiguous span of at least X nucleotides, wherein X is any integer value beginning with 5; the upper limit for such fragments is one nucleotide less than the total number of nucleotides found in the full-length sequence encoding a particular polypeptide (e.g., a polypeptide comprising SEQ ID NO: 2).

In some embodiments, the subject invention includes those fragments capable of hybridizing under various conditions of stringency conditions (e.g., high or intermediate or low stringency) with a nucleotide sequence according to the invention; fragments that hybridize with a nucleotide sequence of the subject invention can be, optionally, labeled as set forth below.

The subject invention provides, in one embodiment, methods for the identification of the presence of nucleic acids according to the subject invention in transformed host cells. In these varied embodiments, the invention provides for the detection of nucleic acids in a sample (obtained from a cell culture) comprising contacting a sample with a nucleic acid (polynucleotide) of the subject invention (such as an RNA, mRNA, DNA, cDNA, or other nucleic acid). In a preferred embodiment, the polynucleotide is a probe that is, optionally, labeled and used in the detection system. Many methods for detection of nucleic acids exist and any suitable method for detection is encompassed by the instant invention. Typical assay formats utilizing nucleic acid hybridization includes, and are not limited to, 1) nuclear run-on assay, 2) slot blot assay, 3) northern blot assay (Alwine et al., 1977, 4) magnetic particle separation, 5) nucleic acid or DNA chips, 6) reverse Northern blot assay, 7) dot blot assay, 8) in situ hybridization, 9) RNase protection assay (Melton et al, 1984) and as described in the 1998 catalog of Ambion, Inc., Austin, Tex., 10) ligase chain reaction, 11) polymerase chain reaction (PCR), 12) reverse transcriptase (RT)-PCR (Berchtold, 1989), 13) differential display RT-PCR (DDRT-PCR) or other suitable combinations of techniques and assays. Labels suitable for use in these detection methodologies include, and are not limited to 1) radioactive labels, 2) enzyme labels, 3) chemiluminescent labels, 4) fluorescent labels, 5) magnetic labels, or other suitable labels. These methodologies and labels are well known in the art and widely available to the skilled artisan. Likewise, methods of incorporating labels into the nucleic acids are also well known to the skilled artisan.

Thus, the subject invention also provides detection probes (e.g., fragments of the disclosed polynucleotide sequences) for hybridization with a target sequence or the amplicon generated from the target sequence. Such a detection probe will comprise a contiguous/consecutive span of at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleotides of SEQ ID NO: 1, 3, 5, 7, 9, 11, 13, 15, 17, 19 or 21. Labeled probes or primers are labeled with a radioactive compound or with another type of label as set forth above (e.g., 1) radioactive labels, 2) enzyme labels, 3) chemiluminescent labels, 4) fluorescent labels, or 5) magnetic labels). Alternatively, non-labeled nucleotide sequences may be used directly as probes or primers; however, the sequences are generally labeled with a radioactive element ($^{32}P$, $^{35}S$, $^{3}H$, $^{125}I$) or with a molecule such as biotin, acetylaminofluorene, digoxigenin, 5-bromo-deoxyuridine, or fluorescein to provide probes that can be used in numerous applications.

Polynucleotides of the subject invention can also be used for the qualitative and quantitative analysis of gene expression using arrays or polynucleotides that are attached to a solid support. As used herein, the term array means a one-, two-, or multi-dimensional arrangement of full length polynucleotides or polynucleotides of sufficient length to permit specific detection of gene expression. Preferably, the fragments are at least 15 nucleotides in length. More preferably, the fragments are at least 100 nucleotides in length. More preferably, the fragments are more than 100 nucleotides in length. In some embodiments the fragments may be more than 500 nucleotides in length.

For example, quantitative analysis of gene expression may be performed with full-length polynucleotides of the subject invention, or fragments thereof, in a complementary DNA microarray as described by Schena et al. (1995, 1996a). Polynucleotides, or fragments thereof, are amplified by PCR and arrayed onto silylated microscope slides. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

mRNA is isolated from a biological sample and probes are prepared by a single round of reverse transcription. Probes are hybridized to 1 $cm^2$ microarrays under a 14×14 mm glass coverslip for 6-12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of the polynucleotides present in a biological sample can also be performed in complementary DNA arrays as described by Pietu et al. (1996). The polynucleotides of the invention, or fragments thereof, are PCR amplified and spotted on membranes. Then, mRNAs originating from biological samples derived from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, the polynucleotide sequences related to the invention may also be used in analytical systems, such as DNA chips. DNA chips and their uses are well known in the art (see for example, U.S. Pat. Nos. 5,561,071; 5,753,439; 6,214,545; Schena 1996b; Bianchi et al., 1997; each of which is hereby incorporated by reference in their entireties) and/or are provided by commercial vendors such as Affymetrix, Inc. (Santa Clara, Calif.). In addition, the nucleic acid sequences of the subject invention can be used as molecular weight markers in nucleic acid analysis procedures.

The subject invention also provides genetic constructs comprising: a) a polynucleotide sequence encoding a polypeptide comprising SEQ ID NO: 2, 4, 6, 8, 10, 12, 14, 16, 18 or 20, or any fragment thereof; b) a polynucleotide sequence having at least about 20% to 99.99% identity to a polynucleotide sequence encoding a polypeptide comprising SEQ ID NO: 2, 4, 6, 8, 10, 12, 14, 16, 18 or 20, or any fragment thereof, wherein said polynucleotide encodes a polypeptide having at least one of the activities or a polypeptide comprising SEQ ID NO: 2, 4, 6, 8, 10, 12, 14, 16, 18 or 20; c) a polynucleotide sequence encoding a fragment of a polypeptide comprising SEQ ID NO: 2, 4, 6, 8, 10, 12, 14, 16, 18 or 20, wherein said fragment has at least one of the activities of the polypeptide of SEQ ID NO: 2, 4, 6, 8, 10, 12, 14, 16, 18 or 20; d) a polynucleotide sequence comprising SEQ ID NO: 1, 3, 5, 7, 9, 11, 13, 15, 17, 19 or 21; e) a polynucleotide sequence having at least about 20% to 99.99% identity to the polynucleotide sequence of SEQ ID NO: 1, 3, 5, 7, 9, 11, 13, 15, 17, 19 or 21) a polynucleotide sequence encoding variant (e.g., a variant polypeptide) of the polypeptide of SEQ ID NO: 2, 4, 6, 8, 10, 12, 14, 16, 18 or 20, wherein said variant has at least one of the activities associated with the polypeptide from which it was derived; f) a polynucleotide sequence encoding a fragment of a variant polypeptide as set forth in (e); or g) a polynucleotide that is complementary to the polynucleotides set forth in (a), (b), (c), (d), (e) or (f). Genetic constructs of the subject invention can also contain additional regulatory elements such as promoters and enhancers and, optionally, selectable markers.

Also within the scope of the subject instant invention are vectors or expression cassettes containing genetic constructs as set forth herein or polynucleotides encoding the polypeptides, set forth supra, operably linked to regulatory elements. The vectors and expression cassettes may contain additional transcriptional control sequences as well. The vectors and expression cassettes may further comprise selectable markers. The expression cassette may contain at least one additional gene, operably linked to control elements, to be co-transformed into the organism. Alternatively, the additional gene(s) and control element(s) can be provided on multiple expression cassettes. Such expression cassettes are provided with a plurality of restriction sites for insertion of the sequences of the invention to be under the transcriptional regulation of the regulatory regions. The expression cassette(s) may additionally contain selectable marker genes operably linked to control elements.

The expression cassette will include in the 5'-3' direction of transcription, a transcriptional and translational initiation region, a DNA sequence of the invention, and a transcriptional and translational termination regions. The transcriptional initiation region, the promoter, may be native or analogous, or foreign or heterologous, to the host cell. By "foreign" is intended that the transcriptional initiation region is not found in the organism into which the transcriptional initiation region is introduced.

The subject invention also provides for the expression of a polypeptide, peptide, fragment, or variant encoded by a polynucleotide sequence disclosed herein comprising the culture of a host cell transformed with a polynucleotide of the subject invention under conditions that allow for the expression of the polypeptide and, optionally, recovering the expressed polypeptide.

As discussed above, the subject application also provides host cells transformed by at least one nucleic acid or vector according to the invention. These cells may be obtained by introducing into host cells a nucleotide sequence inserted into a vector as defined above, and then culturing the said cells under conditions allowing the replication and/or the expression of the polynucleotide sequences of the subject invention.

The host cell may be chosen from eukaryotic or prokaryotic systems, such as for example bacterial cells, (Gram negative or Gram positive), yeast cells (for example, *Saccharomyces cereviseae* or *Pichia pastoris*), animal cells (such as Chinese hamster ovary (CHO) cells), plant cells, and/or insect cells using baculovirus vectors. In some embodiments, the host cells for expression of the polypeptides include, and are not limited to, those taught in U.S. Pat. Nos. 6,319,691, 6,277, 375, 5,643,570, or 5,565,335, each of which is incorporated by reference in its entirety, including all references cited within each respective patent.

Another aspect of the invention provides:
a) one or more:
  1) isolated, purified, and/or recombinant polypeptides comprising SEQ ID NO: 2, 4, 6, 8, 10, 12, 14, 16, 18 or 20;
  2) variant polypeptides having at least about 20% to 99.99% identity, preferably at least 60 to 99.99% identity to the polypeptide of SEQ ID NO: 2, 4, 6, 8, 10, 12, 14, 16, 18 or 20 and which has at least one of the activities associated with the polypeptide of SEQ ID NO: 2, 4, 6, 8, 10, 12, 14, 16, 18 or 20;
  3) a fragment of the polypeptide of SEQ ID NO: 2, 4, 6, 8, 10, 12, 14, 16, 18 or 20, or a variant polypeptide, wherein said polypeptide fragment or fragment of said variant polypeptide has substantially the same activity as the polypeptide of SEQ ID NO: 2, 4, 6, 8, 10, 12, 14, 16, 18 or 20; or
  4) a polypeptide according to embodiments a(1), a(2) or a(3) that further comprises a heterologous polypeptide sequence;
b) a composition comprising a carrier and a polypeptide as set forth in a(1), a(2), a(3) or a(4), optionally wherein said carrier is an adjuvant or a pharmaceutically acceptable excipient; or
c) antibodies that specifically bind to a polypeptide comprising SEQ ID NO: 2, 4, 6, 8, 10, 12, 14, 16, 18 or 20, variants thereof or fragments thereof.

In the context of the instant invention, the terms "oligopeptide", "polypeptide", "peptide" and "protein" can be used interchangeably; however, it should be understood that the invention does not relate to the polypeptides in natural form, that is to say that they are not in their natural environment but that the polypeptides may have been isolated or obtained by purification from natural sources or obtained from host cells prepared by genetic manipulation (e.g., the polypeptides, or fragments thereof, are recombinantly produced by host cells, or by chemical synthesis). Additionally, the terms "amino acid(s)" and "residue(s)" can be used interchangeably.

Polypeptide fragments of the subject invention can be any integer in length from at least 3, preferably 4, and more preferably 5 consecutive amino acids to 1 amino acid less than a full length polypeptide of SEQ ID NO: 2, 4, 6, 8, 10, 12, 14, 16, 18 or 20.

Fragments, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Such polypeptide fragments may be equally well prepared by chemical synthesis or using hosts transformed with an expression vector according to the invention. The transformed host cells contain a nucleic acid, allowing the expression of these fragments, under the control of appropriate elements for regulation and/or expression of the polypeptide fragments.

In certain preferred embodiments, fragments of the polypeptides disclosed herein retain at least one property or activity of the full-length polypeptide from which the fragments are derived. Thus, fragments of the polypeptide of SEQ ID NOs: SEQ ID NO: 2, 4, 6, 8, 10, 12, 14, 16, 18 or 20 have one or more of the following properties or activities set forth in Table 4 or any of the activities described within the Example section of this application (e.g., see Results).

A "variant polypeptide" (or polypeptide variant) is to be understood to designate polypeptides exhibiting, in relation to the natural polypeptide, certain modifications. These modifications can include a deletion, addition, or substitution of at least one amino acid, a truncation, an extension, a chimeric fusion, a mutation, or polypeptides exhibiting post-translational modifications. Among these homologous variant polypeptides, are those comprising amino acid sequences exhibiting between at least (or at least about) 20.00% to 99.99% (inclusive) identity to the full length, native, or naturally occurring polypeptide are another aspect of the invention. The aforementioned range of percent identity is to be taken as including, and providing written description and support for, any fractional percentage, in intervals of 0.01%, between 20.00% and, up to, including 99.99%. These percentages are purely statistical and differences between two polypeptide sequences can be distributed randomly and over the entire sequence length. Thus, variant polypeptides can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polypeptide sequences of the instant invention. In a preferred embodiment, a variant or modified polypeptide exhibits at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity to any one of SEQ ID NOs: 2, 4, 6, 8, 10, 12, 14, 16, 18 or 20. Typically, the percent identity is calculated with reference to the full-length, native, and/or naturally occurring polypeptide (e.g., those polypeptides set forth in SEQ ID NO: 2, 4, 6, 8, 10, 12, 14, 16, 18 or 20). In all instances, variant polypeptides retain at least one of the activities associated with the polypeptide set forth in SEQ ID NO: 2, 4, 6, 8, 10, 12, 14, 16, 18 or 20 from which it was derived.

Variant polypeptides can also comprise one or more heterologous polypeptide sequences (e.g., tags that facilitate purification of the polypeptides of the invention (see, for example, U.S. Pat. No. 6,342,362, hereby incorporated by reference in its entirety; Altendorf et al., (1999-WWW, 2000); Baneyx, (1999); Eihauer et al., (2001); Jones et al. (1995); Margolin (2000); Puig et al., (2001); Sassenfeld (1990); Sheibani (1999); Skerra et al., (1999); Smith (1998); Smyth et al., (2000); Unger (1997), each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or InVitrogen (San Diego, Calif.).

Figure 2:
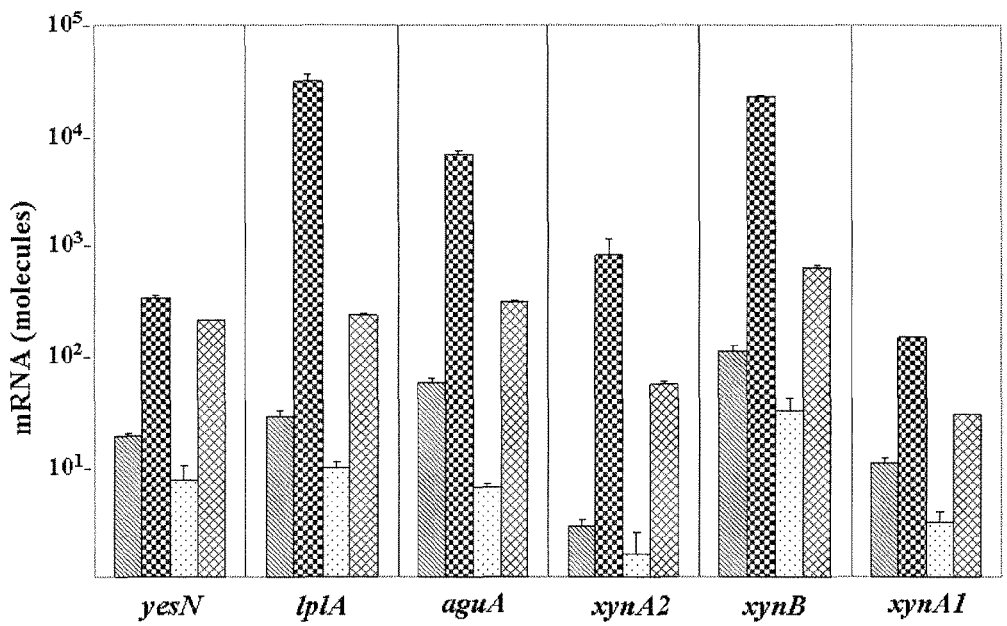
FIG. 2 illustrates aldouronate-utilization gene expression in Paenibacillus sp. JDR-2 grown under different nutrient conditions. A colony of Paenibacillus sp. JDR-2 was dispersed in 420 μl Zucker-Hankin (Zucker et al., 1970) salts medium, and 100 μl of this suspension was added to each of four 8-ml culture medium in 250 ml baffled flasks containing 1× Zucker-Hankin, 0.5% yeast extract and either 1) no additional substrate, back slash; 2) 0.5% oat spelt xylan, checkered; 3) 0.5% glucose, stippled; or 4) 0.5% xylose, crosshatched. The cultures were incubated at 30° C. at 225 rpm for 9 h to O.D.$_{600}$=0.6. Cells were harvested and RNA was prepared from each cell pellet. RNA (100 ng) was added to each 16 μl real-time RT-PCR reaction. At the end of the reaction, threshold cycle levels were converted to mRNA abundance by predetermined standardization of RT-PCR threshold cycles using genomic DNA concentration as standard.

The subject invention also concerns antibodies that bind to polypeptides of the invention. Antibodies that are immunospecific for the polypeptides as set forth herein are specifically contemplated. In various embodiments, antibodies that do not cross-react with other proteins that are substantially related to those disclosed herein (see for example, the polypeptides disclosed in FIG. 2). The antibodies of the subject invention can be prepared using standard materials and methods known in the art (see, for example, *Monoclonal Antibodies: Principles and Practice*, 1983; *Monoclonal Hybridoma Antibodies: Techniques and Applications*, 1982; *Selected Methods in Cellular Immunology*, 1980; *Immunological Methods, Vol. II*, 1981; *Practical Immunology*, and Kohler et al., 1975). These antibodies can further comprise one or more additional components, such as a solid support, a carrier or pharmaceutically acceptable excipient, or a label.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity, particularly neutralizing activity. "Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multi-specific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975), or may be made by recombinant DNA methods (see, e.g., U.S. Pat. No. 4,816,567). The "monoclonal antibodies" may also be isolated from phage antibody libraries using the techniques described in Clackson et al. (1991) and Marks et al. (1991), for example.

The monoclonal antibodies described herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., 1984). Also included are humanized antibodies, such as those taught in U.S. Pat. No. 6,407,213 or 6,417,337 which are hereby incorporated by reference in their entirety.

"Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies (1994) Vol. 113:269-315, Rosenburg and Moore eds. Springer-Verlag, New York.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Finally, the terms "comprising", "consisting of" and "consisting essentially of" are defined according to their standard meaning. The terms may be substituted for one another throughout the instant application in order to attach the specific meaning associated with each term. The phrases "isolated" or "biologically pure" refer to material that is substantially or essentially free from components which normally accompany the material as it is found in its native state. Thus, isolated peptides in accordance with the invention preferably do not contain materials normally associated with the peptides in their in situ environment.

Materials and Methods

Preparation of a cosmid library of *Paenibacillus* sp. strain JDR-2. Culture media (50 ml) were inoculated with 1/250 volume of a starter culture of *Paenibacillus* sp. strain JDR-2 (St. John et al., 2006). The culture was grown at 30° C. with vigorous shaking. After reaching mid-log phase ($OD_{600}$=0.7, 1 $OD_{600}$=$10^9$ cells/ml), cells were collected by centrifugation, resuspended in buffer A (50 mM Tris-HCl, pH 8.0, 1.0 M NaCl), pelleted by centrifugation and resuspended in buffer A again at $4 \times 10^9$ cells/ml. An equal volume of 2% low melt agarose was added to the cell suspension and the cell/agarose mix was poured into 800 µl plug molds. Plugs were further processed according to (Bell et al., 2002).

Partial digestion of genomic DNA. To determine the optimal amount of enzyme to use for digestion, 360 mg of plugs were equilibrated two times in 50 ml TBE (90 mM Trisborate, 2 mM EDTA, pH 8.0) for 15 min, rinsed with 15 ml 0.1% triton X-100, chopped into a slurry and distributed into six 1.5 ml centrifuge tubes. A brief centrifugation (12,000 g, 30 seconds) packed the agarose slurry and the supernates were removed by aspiration. To each tube containing approximately 60 µl of packed plugs were added 10 µl 40 mM spermidine, 10 µl 10× Hind III reaction buffer, and 1 µl bovine serum albumin (10 mg/ml). Water was added to adjust the final volume to 100 µl. The mixtures were equilibrated on ice for 30 min, varying amounts (0.05-0.7 units) of Hind III added to each tube, equilibrated further for 15 min and finally incubated at 37° C. for 30 min to allow restriction digestion. The reactions were immediately stopped by adding 11 µl 0.5 M EDTA, pH 8.0.

Field inversion gel electrophoresis. Slurries of agarose gel plugs were loaded into the wells of a 1% agarose (Bio-Rad) gel in 0.5×TBE or 1×TAE buffer (40 mM Tris-HCl, 20 mM acetic acid, 1 mM EDTA, pH 8.3). Electrophoresis was carried out using the FIGE MAPPER apparatus (Bio-Rad) set at program 8 which separated DNA fragments in the 25-150 kb range. Initial current was 47-50 mA and the run lasted 20 h. At completion, 0.5 g of an agarose gel piece containing Hind III digested DNA ranging in size 20-48 kb was cut out and treated with 6 units of Gelase (Epicentre) at 45° C. The released DNA was ready to be ligated to the cosmid vector.

Construction of cosmid library. Size-selected Hind III-digested genomic DNA fragments were ligated to the Hind III-digested and dephosphorylated cosmid vector pCC1 (Epicenter). Ligation products were packaged into lambda phage packaging extracts (Epicenter) and electroporated into *E. coli* EPI300 (Epicenter) as per protocol provided. Transformed *E. coli* were plated onto LB/chloramphenicol plates (LB broth (Bertani, 1951), in 1.5% bactoagar containing chlamphenicol at 12.5 µg/ml) and the colonies were picked and stored individually in wells of 9×12 microtiter plates supplemented with LB/chloramphenicol media.

Screening of cosmid library for aldouronate-utilization genes. Pooled cultures from 300 transformants were screened for the presence of the aguA gene by PCR using the primers PF54 and PR569 (Table 1). Cosmid DNA preparations from positive clones were sequenced.

Preparation of mRNA. Typically, 8 ml media in 125 ml flasks were each inoculated with a fresh colony of *Paenibacillus* sp. strain JDR-2 and incubated at 30° C. with vigorous shaking at 240 rpm. Cells were collected by centrifugation when growth reached $OD_{600\ nm}$=0.6 and RNA was isolated as per Cheung et al. (1994). To remove residual genomic DNA in the resultant RNA fraction, DNase (Promega M610A) was added at 20 U/ml and digested at 37° C. for 45 min. The DNase was then inactivated by mixing with five volumes of GTC (4 M guanidine thiocyanate, 25 mM sodium acetate, pH 7.0, 0.1 M β-mercaptoethanol and 0.5% sarkosyl). One volume of 1.0 M sodium acetate, pH 4.4, 6 volumes of water-saturated phenol and one volume of chloroform were added and mixed. The mixtures were centrifuged to separate phases, the aqueous phases were transferred to separate tubes and RNA fractions were precipitated following addition of equal volumes of isopropanol. The RNA precipitates were further rinsed with 75% ethanol and dissolved in 100 µl of water. The DNase treatment was repeated until there were no significant traces of genomic DNA-directed PCR products in the subsequent RT-PCR reactions.

RT-PCR. Real-time reverse transcription-PCR was performed in 16 µl reactions each containing 100-200 ng of RNA, 3.2 µl of 0.25 µM primer pair mixtures and 8 µl of 2× iScript SYBR mix (Bio-Rad iScript). A typical reaction consisted of the following steps: 1) incubation with reverse transcriptase for 10 minutes at 58° C., 2) melting for 3 minutes at 95° C., 3) 45 cycles of 10 seconds at 95° C., 20 seconds at 58° C. and 20 seconds at 72° C., and 4) one cycle of melt curve determination. The reactions were conducted in the Bio-Rad iCycler iQ Real-Time Detection System. Primer pairs used for RNA transcript detection were rre178f and rre459r for yesN, sbp1081f and sbp1361r for yesM, aguA1069f and aguA1354r for aguA, xy1247f and xy1623r for xynA2, bex948f and bex1291r for xynB and xynA1-2237f and xynA1-2503r for xynA1. Primer pairs for flanking genes were amp10f and amp204r for the aminopeptidase gene and oxr535f and oxr774r for the oxidoreductase gene. The primer pair used for probing the read-through transcript from ytcP to aguA were perm-aguA791f and perm-aguA81r (Table 1). 15,276 bp of cosmid VC2 was sequenced and submitted to GenBank (accession number: 926135).

Results

Cosmid library analysis. The cosmid library was screened by PCR with degenerate primers PF54 and PR569. Two clones, VC1 and VC2, each yielded aguA-specific PCR generated fragments as confirmed by nucleotide sequencing, and therefore contained the gene encoding α-glucuronidase. VC1 had a 28 kb insert while VC2 had a 35 kb insert. Analyses by restriction digestion showed VC1 and VC2 shared a majority of fragments, indicating that they were from the same genomic region.

Sequence organization of the aldouronate gene cluster in cosmid VC2. VC2 yielded the 486 bp aguA-specific product by PCR screening with primers PF54 and PR569. These primers were established as specific for the aguA gene cloned and sequenced from genomic DNA derived from *Paenibacillus* sp. JDR-2 (Nong et al., 2005). Cosmid VC2 insert DNA was subcloned into pUC19 and 15 kb of the DNA was sequenced. The organization of the genetic content of this 15 kb segment is shown in FIG. 1.

Genes in this segment were identified by BLAST search and defined by identification of open reading frames. Central in this region is an aguA gene encoding a 687 amino acid GH67 α-glucuronidase. This aguA gene was followed by a xynA2 gene encoding a 341 amino acid protein with a GH10 endoxylanase catalytic domain. Following the xynA2 gene was a xynB gene encoding a 521 amino acid protein, classified as β-xylosidase/arabinofuranosidase in the GH43 family. These three genes constituted a triad of structural genes expected to encode enzymes for the processing of the product generated by the anchored multimodular endoxylanase, XynA1, to xylose following assimilation by the cell.

Immediately 5' to this triad were three genes that are presumed to encode proteins that comprise an ABC transporter complex. The expected translated products from this triad include a substrate binding protein, 570 amino acids; a lipoprotein, 323 amino acids; and a permease protein, 306 amino acids. Immediately 5' to the ABC transporter triad were genes capable of encoding a transcription regulation element made up of two proteins—a receiver protein of an AraC-type response regulator of 522 amino acids, and a histidine kinase protein of 572 amino acids. An amino peptidase gene was located 349 bp upstream of the transcription regulation unit, while 285 bp downstream of the xynB gene was an NADH-dependent flavin oxidoreductase gene.

Translation start sites of these genes were indicated by the presence of putative ribosome binding sites (canonical sequence—GGAGGG, (McLaughlin et al., 1981)) located 5 to 15 nucleotides 5' to the translation start sites ATG. These predicted protein products were compared with the archived sequences in GenBank. Genes encoding characterized proteins in the protein databases showing greatest homologies are summarized in Table 2. The average GC content of DNA (approximately 33 kb) of *Paenibacillus* sp. JDR-2 sequenced so far is 52%.

Figure 3:
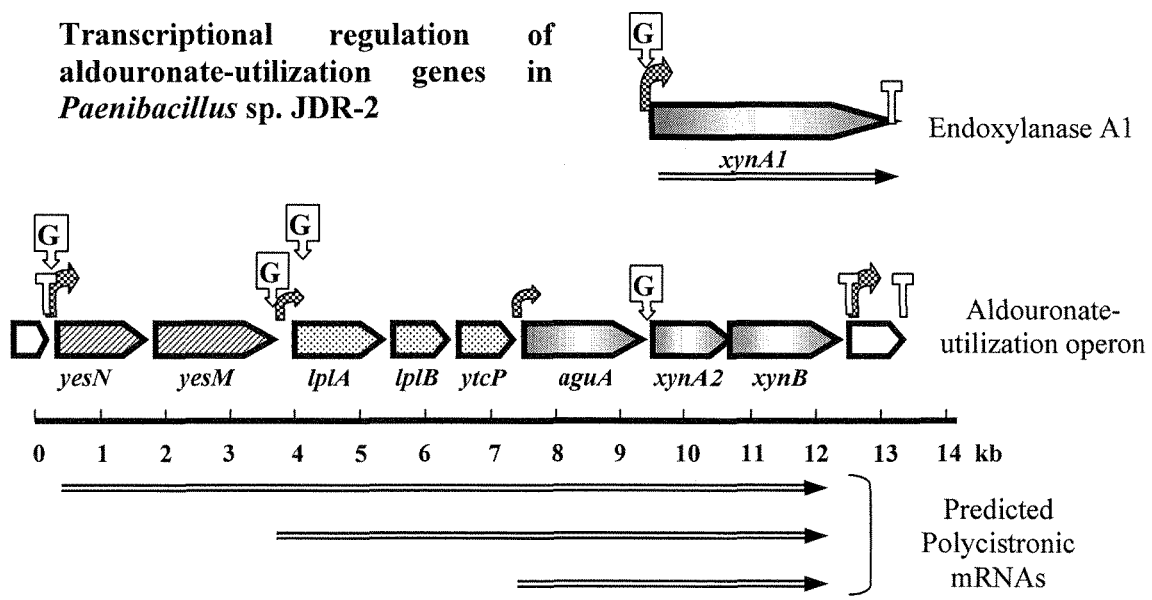
FIG. 3 shows the transcription regulation and gene expression of the aldouronate-utilization gene cluster.

Identification of transcriptional regulation elements in genes associated with utilization of methylglucuronoxylan. The BPROM program (Softberry, see Worldwide Website: softberry.com) was used to locate bacterial promoters and the high scoring transcription start sites were located at the 5'termini of genes potentially encoding YesN, the receiver protein of the response regulator, UgpB, the substrate binding protein of the ABC transporter and AguA, the α-glucuronidase protein of the glycohydrolase triad in the aldouronate-gene cluster. The promoter 5' to YesN was identified as having the greatest potential of the cluster. The FindTerm program (Softberry, see Worldwide Website: softberry.com) was used to locate the rho-independent transcription stop sites. The transcription termination site upstream of yesN was located at 14 bp after the termination codon of the preceding amino peptidase gene and consisted of a 14/20 bp stem-9 bp loop followed by a 7/8 AT stretch, and punctuated the beginning of the aldouronate-utilization gene cluster. The site found downstream from xynB, consisting of a 13/14 bp stem-7 bp loop followed by a 8/9 AT stretch, was located at 16 bp after the termination codon for XynB, and punctuated the end of the aldouronate-utilization gene cluster. The same analyses applied to xynA1 (St. John et al., 2006) identified as well a potential promoter immediately upstream and a stop site downstream from xynA1, located 1 bp after the termination codon and consisted of a 18/23 bp stem-4 bp loop followed by a 4/7 AT stretch. The positions for different promoters and termination sites are presented in FIG. 3.

Transcriptional regulation genes. The yesN and yesM genes together made up a two component transcription regulation unit. Sequence homology analysis by CDD Search (See Worldwide Website: ncbi.nlm.nih.gov/Structure/cdd) of yesN indicated it coded for a response regulator protein containing a CheY-like receiver domain at the initial 121 amino acids at the amino terminus with $Asp^{55}$ as the phosphorylated residue and an AraC-type DNA-binding domain spanning residue 432 to 515 at the carboxyl terminus. We have designated this yesN as homologous to the yesN gene of the gram-positive prototype organism, *Bacillus subtilis* subsp. *subtilus* str. 168. YesM on the other hand contained a HAMP (histidine kinase/adenyl cyclase/metal-binding proteins/phosphatases) domain at residues 275-344, a histidine kinase domain at residues 367-450 with $His^{378}$ as the phosphorylated residue, and an ATPase domain at residues 461-558. Again we designated this yesM for the same reason above. Analysis of this two component unit YesN-YesM by CDD Search identified loci 2109 and 2110 in *Bacillus halodurans* C-125 to be most similar in amino acid content (42% (221/524) and 45% (261/580) identity respectively) and the above described domain architecture. Another similar loci pair identified was *Clostridium cellulolyticum* H10 Draft 2754 and 2755.

ABC-type transporter. The genes encoding the ABC-type transporter are found in the operon as a cassette of three open reading frames (orf). The first orf in this cassette, lplA, encodes a protein homologous to the substrate binding periplasmic component, UgpB, and identified by CDD Search to be at residues 52-398. The second coding sequence, lplB, codes for the transmembrane permease component, LplB, which spans the entire 323 residue length and contains the sequence motif $EAA-X_3-G-X_9-I-X-LP$ (residues 216-235), located in a cytoplasmic loop at a distance of ~100 residues from the C-terminus (Schneider 2001). The third coding sequence, ytcP, encodes a protein with another permease component, spanning residues 16-305. Sequence homology analyses showed this ABC transporter to be most similar to *Bacillus halodurans* C-125 loci 2111-2113 (49% (272/555), 73% (210/287) and 65% (193/293) amino acid identity respectively). Another similar ABC transporter identified was in *Clostridium cellulolyticum* H10 Draft, loci 2757-2759.

Aldouronate processing functions. An aguA gene was identified encoding a GH67 α-glucuronidase with a calculated molecular weight of 77,876 Da and a pI of 5.4. This was the same aguA gene cloned and sequenced from genomic DNA, and shown to encode a functional α-glucuronidase when expressed in *E. coli* (Preston et al., 2003). Identities derived from GenBank entries were: 63% to *Aeromonas punctata*, 62% to *Geobacillus stearothermophilus* T-6, 61% to *Bacillus halodurans* C-125, and 57% to *Clostridium cellulolyticum* H10. This protein is highly conserved with respect to catalytic sites. Based upon alignment with the two bacterial GH67 α-glucuronidases of *G. stearothermophilus* T-6 and *Cellvibrio japonicus* for which catalytic mechanisms have been elucidated (Golan et al., 2004; Nagy et al., 2003), glutamate and aspartate residues that participate in the acid/base catalyzed reactions can be discerned. In AguA from *Paenibacillus* sp. JDR-2 $Glu^{401}$ and $Asp^{373}$ are homologs of residues $Glu^{392}$ and $Asp^{364}$ in *G. stearothermophilus* T-6 and $Glu^{393}$ and $Asp^{365}$ in *C. japonicus*, which together with a water molecule constitute the catalytic general base. Similarly, $Glu^{294}$ in *Paenibacillus* sp. JDR-2 probably corresponds to $Glu^{285}$ in *G. stearothermophilus* T-6 and $Glu^{292}$ in *C. japonicus* as the catalytic general acid. Catalysis results in the hydrolysis of the α-1,2-glycosidic bond between the 4-O-methylglucuronic acid residue and the xylose residue in the aldo-oligouronate substrate by an inverting mechanism.

A xynA2 gene, encoding the catalytic domain for a GH10 endoxylanase without a signal sequence, (determined by SignalP (Bendtsen et al., 2004)), follows aguA. It has a calculated molecular weight of 39,457 Da and a calculated pI of 5.3, and showed 60-61% identity to GH10 xylanase catalytic domains presumed to function as an intracellular enzyme in other bacteria, e.g., *Geobacillus stearothermophilus* T-6 and *Thermotoga maritima* MSB8.

The last gene in this triad and the last gene in this aldouronate-utilization cluster, xynB, encodes a protein of 521 amino acids with an internal family GH43 β-xylosidase, α-arabinofuranosidase defined within residues 11-288. It did not have a signal peptide, had a calculated molecular weight of 57,783 Da and a calculated pI of 4.9. A gap of 285 non-coding bases was found between this last gene and the next, encoding a putative NADH-dependent flavin oxidoreductase. This xylosidase contained a 40% identity to that found in *Bacillus clausii* KSM-K16 and 40% with that found in *Geobacillus thermoleovorans*.

Effects of xylan, glucose and xylose on the relative expression levels of aldouronate-utilization genes. Real-time RT-PCR analysis of the amount of mRNA produced under these growth conditions (FIG. 2) suggested a concerted effect of induction and repression of genes in this cluster, as well as the xynA1 encoding the secreted multimodular GH10 endoxylanase. When growing in only 0.5% yeast extract, all six genes (yesN, lplA, aguA, xynA2, xynB and xynA1) were expressed with aguA and xynB mRNAs slightly more abundant. With these mRNA levels at 0.5% yeast extract considered as points of reference, we found that when 0.5% xylan was added to the yeast extract-containing media, gene expressions of the six were dramatically enhanced, from 18-fold, in the case of the response regulator yesN, to more than 200-fold, in the case of the substrate binding protein, lplA and the β-xylosidase, xynB. Interestingly, when glucose was added to supplement yeast in the media instead of xylan, the relative mRNA molecule pools of the six monitored genes were all variously reduced to about two-thirds (67%, xynA2) and to as much as one-tenth (10% aguA) of basal level. Xylose, on the other hand, slightly induced expression resulting in a 2.7-fold increase (xynA1) to 19-fold increase (xynA2) over basal level. In addition, by performing real-time RT-PCR with the primer pair perm-aguA791f and perm-aguA81r, read-through transcripts from ytcP to aguA were also identified.

In separate experiments, relative expression analyses of the 5' gene (encoding putative aminopeptidase) and the 3' gene (encoding putative oxidoreductase) that flank this 8 orfs comprising the aldouronate-utilization gene cluster showed modest variations in response fluctuating from a 3-fold increase to a 3-fold decrease of growth on different carbon sources compared to the basal level with yeast-extract alone.

Glucose repression and CcpA binding sites. In the real-time RT-PCR analyses, expressions of aldouronate-utilization genes were reduced up to 10-fold for genes within the cluster and more than 3-fold for xynA1 outside this cluster when glucose was added to the culture media containing yeast extract. Glucose catabolite repression in *G. stearothermophilus* (Cheung et al., 1994) led to the identification of a 14-base canonical sequence within or immediately preceding genes responsive to such transcription repression. With visual inspection of *Paenibacillus* sp. JDR-2 sequences and analysis with the Prokaryotic Promoter Prediction program, at least five such sequences were detected—a sequence 5' to the response regulator yesN, a second 5' to lplA, a third about 100 bp 3' from the translation start site of lplA, a fourth 5' to xynA2 and a fifth 5' to xynA1—the endoxylanase gene located distal to this cluster (Table 3).

Gene organization and regulation of gene expression. Based upon similarities to homologs defined in other bacteria, the ABC transporter located 5' to the aguA gene are most likely concerned with the import of oligoaldouronate substrate for intracellular degradation. Conners et al. (2005) in a recent study of the ABC transporters in *Thermotoga maritima* concluded that ABC transporters for carbohydrate uptake are probably controlled by local regulators responsive to the transport substrate or a key metabolic degradation product. Shulami et al. (2007) reported that the two component response regulator and ABC transporter found upstream of the glycohydrolases (GH67, GH52) in *Geobacillus stearothermophilus* T-6 regulated the expression of this cluster. The organization of the genes in *Paenibacillus* sp. JDR-2 encoding putative transcriptional regulators, transporters, and glycohydrolases, as well as their coordinate regulation, is consistent with these interpretations. The identification of cre motifs within selected genes within each triad further defines the basis for this regulation.

Data from real-time RT-PCR indicated the genes within the aldouronate-utilization cluster in *Paenibacillus* sp. JDR-2 were regulated as a unit by the same transcription signals and were differentially expressed compared to the flanking genes encoding amino peptidase and oxidoreductase. The coordinate expression of the aldouronate-utilization gene cluster along with the expression of the xynA1 gene encoding the multimodular and cell anchored GH10 endoxylanase supports the case made earlier for the coupling of the depolymerization of methylglucuronoxylan with assimilation and processing of the product, $MeGAX_3$ (St. John et al., 2006). The aldouronate-utilization gene cluster, itself comprised of three potential operons coordinately responding to induction or repression (FIG. 3), may thus be considered a regulon. The coordinate response of these genes with xynA1 expands the scope of this regulon to the function of methylglucuronoxylan or xylan-utilization. Further definition of these processes awaits development of transformation systems in *Paenibacillus* sp. JDR-2, or the expression of these systems in *Bacillus* spp. amenable to transformation.

Figure 4:
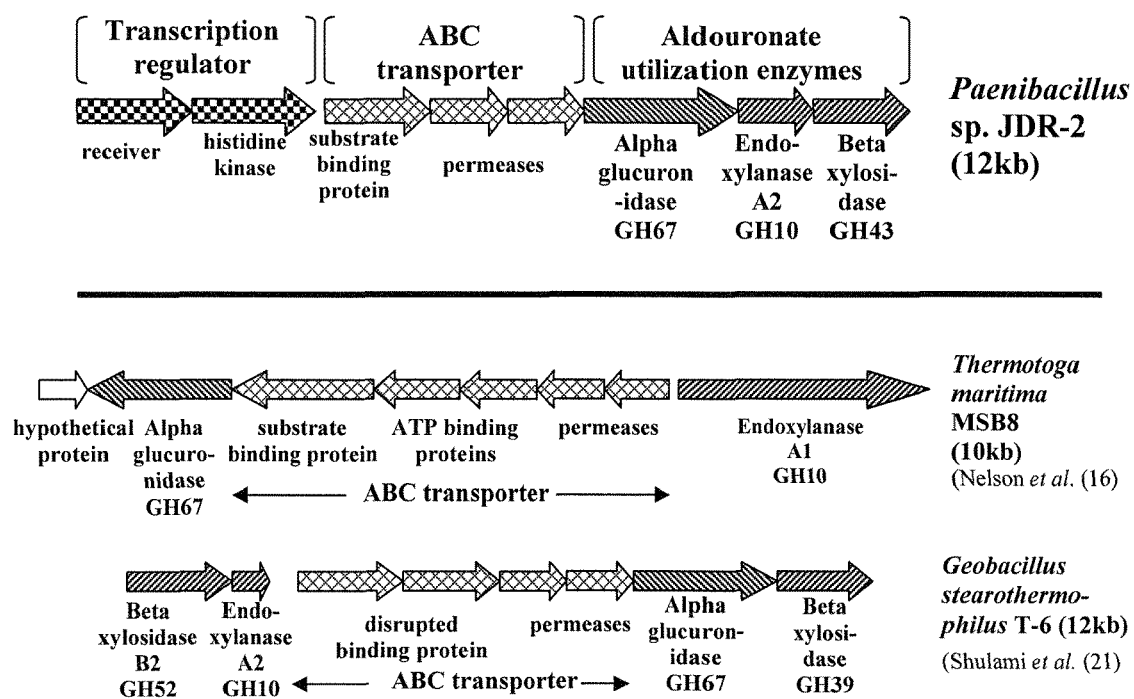
FIG. 4 relates to a comparison of aldouronate-utilization gene organizations in bacteria in which evidence supports relationships of gene function to substrate utilization.
Figure 5A:
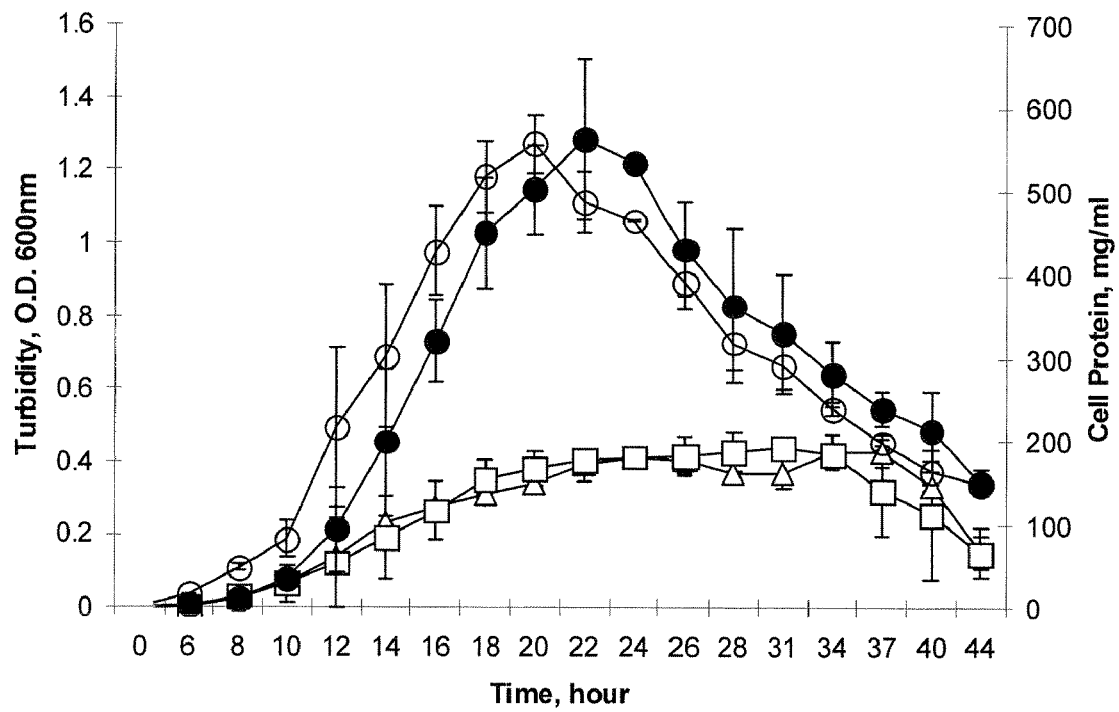
FIGS. 5A and 5B. Growth and substrate utilization of *Paenibacillus* sp. JDR-2 on Zucker-Hankin minimal medium supplemented 0.01% yeast extract and either MeGAX$_n$, MeGAX$_3$, or MeGAX$_1$.
Figure 5B:
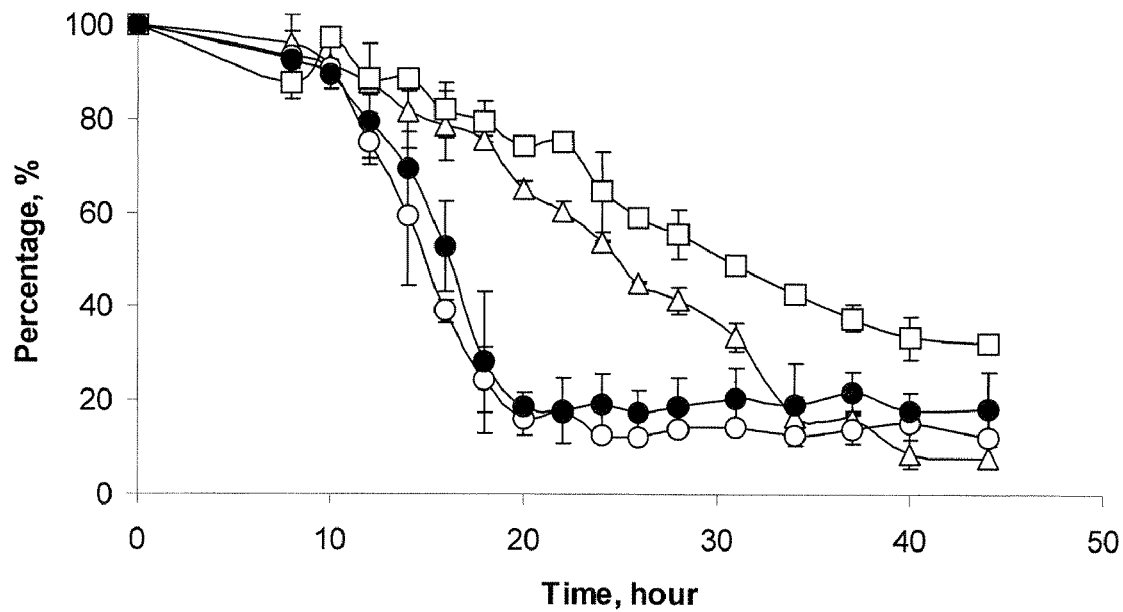
Figure 6:
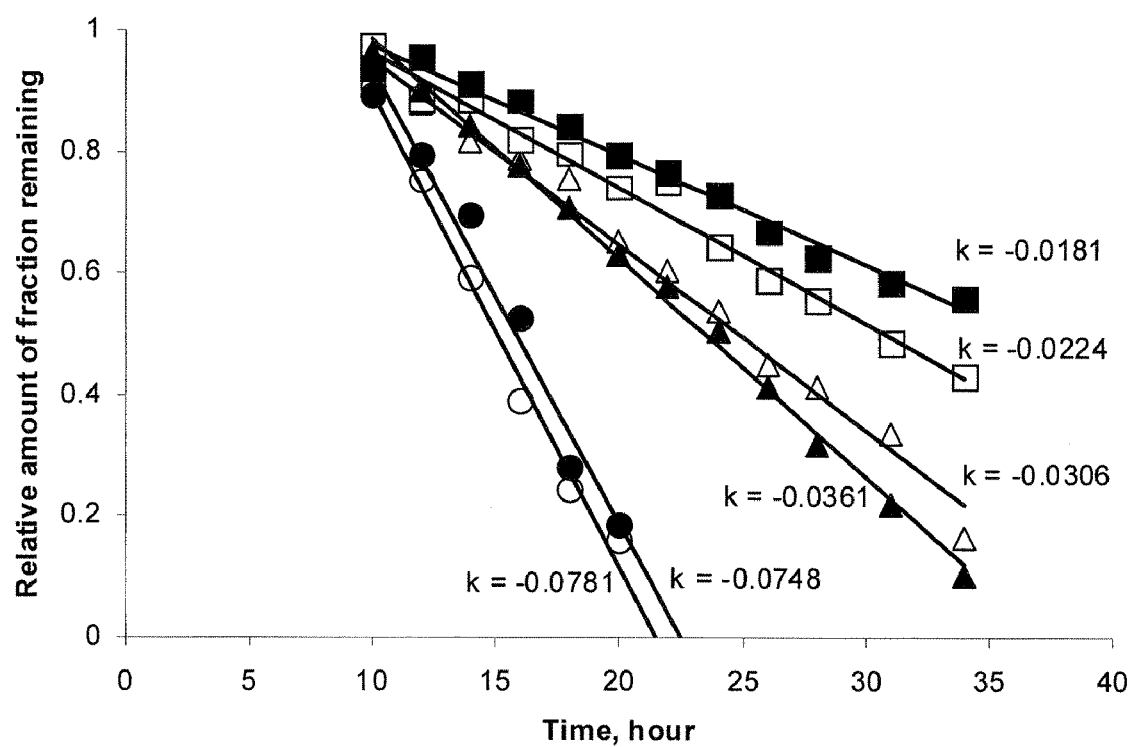
FIG. 6. Comparison of substrate utilization rates during the most rapid growth phase (10 to 20 h) of *Paenibacillus* sp. JDR-2 on Zucker-Hankin minimal medium supplemented 0.01% yeast extract and either MeGAX$_n$, MeGAX$_3$, or MeGAX$_1$. Utilization of substrates was determined by total carbohydrate assay: MeGAX$_n$ (open circles), MeGAX$_1$ (open triangles), and MeGAX$_3$ (open squares); and by total uronic acid assay: MeGAX$_n$ (closed circles), MeGAX$_n$ (closed triangles), and MeGAX$_3$ (closed squares). Curves were generated for best fit as described in the Methods section. Relative rates of utilization, noted as k values for the slopes, were −0.0781 and −0.0748 for MeGAX$_n$; −0.0306 and −0.0361 for MeGAX$_1$; −0.0224 and −0.0181 for MeGAX$_3$. $R^2$ values ranged from 0.975 to 0.997.

Comparative genomic organizations of aldouronate-utilization clusters. The organization of the aldouronate-utilization gene clusters in bacteria that have been studied for this function is presented in FIG. 4. While there are parallels as noted above, there are also salient differences. There were no nucleotide-binding domains identified in this *Paenibacillus* sp. ABC transporter cassette. Neither were genes encoding ATP-binding proteins detected in the four open reading frames (orfs) that precede the aguA gene in *Geobacillus stearothermophilus* T-6, where the first two orfs were identified as an interrupted substrate binding protein and the last two orfs were identified as permeases (Shulami et al., 1999). It has been noted in different gram-positive bacteria that a single ATPase may serve more than one set of substrate-binding and membrane-associated proteins that comprise typical ABC transporter systems (Quentin et al., 1999; Schneider, 2001). In the case of *Thermologa maritima* MSB8 (Nelson et al., 1999) where five orfs were located adjacent to aguA, two orfs were identified as genes encoding ATP-binding proteins, and located between genes encoding a substrate binding protein and two permeases.

Another feature distinguishing each of these aldouronate-utilization clusters is the relationship to the secreted GH10 endoxylanase, as well the structural properties of the GH10 endoxylanase itself. Both *Paenibacillus* sp. JDR-2 and *Thermotoga maritima* MSB8 secrete large multimodular enzymes that include family 22 carbohydrate binding modules (CBM) as well as the GH10 catalytic domain that is distinctive for its generation of the aldotetrauronate MeGAX$_3$. The *Paenibacillus* sp. JDR-2 secretes a 1467 amino acid endoxylanase comprised of three family 22 CBMs followed by a GH10 catalytic domain followed by a single family 9 CBM and triplicate surface layer homology domains (SLH) on the C-terminus. This enzyme is cell bound, presumably anchored by the C-terminal SLH modules, and the MeGAX$_3$ and xylooligosaccharides are rapidly assimilated as they are released during depolymerization of methylglucuronoxylan (St. John et al., 2006). The xynA1 gene encoding this enzyme is located distal from the aldouronate-utilization gene cluster, as it is not found in cosmids containing 35 kb inserts that include the 14 kb aldouronate-utilization cluster it self. *Thermotoga maritima* secretes a multimodular 1059 amino acid GH10 endoxylanase that contains two family CBMs followed by a GH10 catalytic domain but lacks SLH domains, and has not been shown to be cell-associated. The xynA1 gene encoding this enzyme is found adjacent to the permease gene for the ABC transporter, and its transcription is in a direction opposite for the genes encoding ABC transporter proteins and AguA. *Geobacillus sterothermophilus* T6 secretes a 407 amino acid GH10 endoxylanase comprised of a catalytic domain and a 28 amino acid signal peptide, lacking modules to associate with glucan or xylan polymers, or to anchor the enzyme to the cell surface. The xynA1 gene encoding this enzyme is located near the aldouronate-utilization cluster, separated by ten genes most of which encode enzymes involved in glucuronate metabolism (Shulami et al., 1991). Evidence for coordinate expression of aldouronate-utilization genes has been demonstrated, but not for the expression of the xynA1 gene that encodes the secreted GH10 endoxylanase.

Development of bacteria for bioconversion of methylglucuronoxylan. The rapid and complete utilization of methylglucuronoxylan, along with the synchronized induction and repression of the genes comprising the xylan-utilization regulon supports further development of *Paenibacillus* sp. JDR-2 for the direct conversion of methylglucuronoxylan to bio-based products. Growth under conditions of oxygen limitation allow formation of minor amounts of acetate, lactate, succinate and ethanol.

The compact configuration of the aldouronate-utilization gene cluster from *Paenibacillus* sp. JDR-2 and its coordinate control recommend it as a cassette for transformation of other gram-positive bacteria that have been or may be developed for efficient fermentation of xylose. Additional transformation with the xynA1 gene encoding the multimodular GH10 endoxylanase may provide the products for assimilation and subsequent metabolism. The presence of carbohydrate binding modules for interaction with cellulosic polysaccharides and surface layer homology domains that anchor the catalytic domain and associated substrate to the surface of the cell generate products that are in turn rapidly assimilated into the cell. The collective properties that allow extracellular depolymerization, assimilation and metabolism are presumably the basis for the aggressive xylanolytic activity of *Paenibacillus* sp. JDR-2. Through genetic engineering, gram-positive bacterial biocatalysts may then be developed for the digestion and vectoral conversion of the hemicellulose fraction of cellulosic resources to renewable fuels and chemicals.

Example 2

Materials and Methods

Cultivation of *Paenibacillus* sp. Strain JDR-2 and Substrate Utilization.

*Paenibacillus* sp. strain JDR-2 was isolated and identified in this laboratory as previously described (St. John et al., 2006). Viable cultures were stored in 30% (v/v) glycerol at −70° C. and resuscitated in Zucker-Hankin medium (Zucker et al., 1970) supplemented with 0.5% oat-spelt xylan, 0.01% yeast extract as needed. A stock culture has been deposited with the *Bacillus* Genetic Stock Center (See Worldwide Website: bgsc.org) under accession number 35A1. Resuscitated cultures were maintained at 30° C. for 2 to 3 weeks with daily transfers in liquid cultures of Zucker-Hankin medium supplemented with 0.5% oat-spelt xylan.

To establish the growth curve, a single colony of *Paenibacillus* sp. JDR-2 was inoculated in Zucker-Hankin medium supplemented with 0.2% of yeast extract, and then, the cells were grown to early exponential phase at 30° C. with shaking on a G-2 gyrotary shaker (New Brunswick Scientific) at 200 rpm. The culture was used to inoculate, as 5% of final volume, fresh Zucker-Hankin medium supplemented with different carbon sources (0.2% of sweetgum xylan, MeGAX$_1$ or MeGAX$_3$) and 0.01% of yeast extract in replicate. Samples (150 µl) were removed to measure the growth as turbidity (OD$_{600}$). Following centrifugation of the samples, cell pellets were collected for protein assay and the supernatants were transferred to fresh 0.5-ml centrifuge tubes for total carbohydrate assay, uronic acid assay and TLC analysis. Best fit linear curves were defined with Excel for maximum rates of utilization of substrates.

Preparation of Aldouronates.

MeGAX$_n$ was prepared from sweetgum (*Liquidamber styrachiflua*) sawdust and structurally defined by $^{13}$C-NMR. MeGAX$_3$ (4-O-methyl-D-glucuronate α-1,2-linked to the reducing terminal xylose of β-1,4-xylotrioside) was obtained as a major aldouronate following the depolymerization of MeGAX$_n$ with the GH10 xylanase XynA$_1$ catalytic domain from *Paenibacillus* sp. strain JDR-2 in 0.1 M potassium phosphate (pH 6.5) at 45° C. Following filtration through a YM-3 membrane (Amicon) and concentration of the reaction mixture by flash evaporation at 50° C., oligomers were resolved on a 2.5 cm by 150 cm P-2 column (Bio-Rad) using 0.05 M formic acid as the eluent. Pooled fractions comprising the MeGAX$_3$ peak were lyophilized, dissolved in 0.22 µm filtered distilled water, analyzed for composition as above and authenticated by thin layer chromatography on silica gel 60 plates as described below. MeGAX$_4$ (4-O-methyl-D-glucuronate α-1,2-linked to the xylose residue penultimate to the reducing terminal xylose of β-1,4-xylotetraoside) was prepared as a limit product following incubation of pure GH11 endoxylanase from *Trichoderma longibrachiatum* (Hampton Research, Laguna Niguel, Calif. 92677) in 0.05 M sodium acetate (pH 5.5) at 30° C. and purified as for MeGAX$_3$. This preparation also included a small amount of MeGAX$_5$. Purified MeGAX$_1$ and MeGAX$_2$ were obtained as aldouronate products of the hydrolysis of MeGAX$_n$ with 0.5% H$_2$SO$_4$ at 120° C. for 60 min. Upon cooling to room temperature, the hydrolysate was neutralized with BaCO$_3$ to a pH of approximately 3.5, cooled at −20° C. for 30 minutes, and filtered through a GF-C filter. Acidic oligomers were bound to AG2-X8 resin (Bio-Rad) in the acetate form by placing on a gyrotory shaker for 1 hour. The slurry was poured into a 2.5 cm by 20 cm glass column and rinsed with distilled water until no reaction to the total carbohydrate assay was observed in the eluate. Bound oligomers were bulk eluted by displacement with 20% acetic acid, concentrated by flash evaporation, subjected to P-2 column chromatography and analyzed as above.

Determination of Growth and Substrate Utilization

Culture growth was followed by turbidity determined as optical density at 600 nm (OD$_{600}$), measured in a 1.00 cm cuvette on a Beckman DU500 series spectrophotometer. When necessary, cultures were diluted to provide OD$_{600}$ readings between 0.2 and 0.8 which were then corrected for dilution to provide data for growth curves. For biomass determination, cells were collected by centrifugation and assayed for total protein. Cell pellets were resuspended in 200 µl of 1 N NaOH and incubated in a water bath at 85° C. for 10 min. Samples were cooled to room temperature, neutralized with an equal normal of 1 N HCl, and assayed for total protein following the procedures of BCA™ Protein Assay Kit (Pierce chemical Co., Rockford, Ill. 61105) using bovine serum albumin as a standard.

Utilization of substrates was determined by the disappearance of total carbohydrate in medium samples using the phenol sulfuric acid method with xylose as a standard (Dubois et al., 1956). The utilization of aldouronates was separately determined by quantifying uronic acid concentrations in a colorimetric assay using glucuronic acid as a standard (Bluemenkrantz et al., 1973). To determine the consumption of different carbon substrates (MeGAX$_1$, MeGAX$_3$, MeGAX$_n$), the supernates (containing 100 nmoles of xylose equivalent determined as total carbohydrate) of media samples taken at different times were loaded on a TLC plate (Silica gel 60, 0.25 mm thickness, EM Laboratories, Inc.). The plate was developed in with chloroform/acetate acid/water (6:7:1, v/v) using 2×4 h double ascension (Zhou et al., 2001). Plates were air-dried for 10 min and sprayed with 6.5 mM N-(1-naphthyl)-ethylenediamine dihydrochloride in methanol containing 3% (v/v) of sulfuric acid (Bounias 1980). The stained plate was baked in an oven at 90° C. for 10 min for visualization.

Cloning and Sequencing.

The identification of relevant genes started with the application of PCR to detect, clone and sequence a gene (aguA) encoding a GH 67 α-glucuronidase. Degenerate primers (F750-GCATTAATGCAATTTCAATTAATAAYGT-NAAYGT (SEQ ID NO:22), R1201-CAGATGTTTTTGT-TGGCCTGTRTAYTCYTGNGT (SEQ ID NO:23)) of aguA gene were designed. Using the genomic library of *Paenibacillus* sp. JDR-2 as template, a PCR reaction was run under the touchdown protocol: 1 cycle of 60 seconds at 98° C.; 21 cycles of 20 seconds at 95° C., 30 seconds per cycle starting at 60° C., decreasing setpoint temperature after cycle 2 by 0.5° C. per cycle, and extension for 40 seconds at 72° C.; 20 cycles of 20 seconds at 95° C., 30 seconds at 50° C. and extension for 40 seconds at 72° C.; and an additional extension for 10 minutes at 72° C. PCR products were identified following electrophoresis in 1.5% of agarose gel slabs. The predominant band of the predicted size was detected by ethidium bromide staining and excised from gel for cloning into pCR2.1-TOPO vector. Following transformation into *E. coli* TOP10 and growth on LB agar containing 100 µg·ml$^{-1}$ of ampicillin. Colonies were selected for sequencing. The sequences obtained were used to design sequence-specific primers (F54-CGAGAGACATTCCTTATTACGGAGA (SEQ ID NO:24), R569-CATCTGGTTGGTATGCTC-CATCG (SEQ ID NO:25)) that were applied to screen the genomic library for determination aguA and contiguous gene sequences in the genome.

Expression Constructs of aguA and xynA2 Genes.

Specific primers with the addition of restriction enzyme sites of the aguA gene (F-GGCCATGGGAGACAACG-GATACGC (SEQ ID NO:26), R-CACCTCGAGTGAATC-GATTTGCCCCGC (SEQ ID NO:27)) and xynA2 (F-CG-GACATGTCATATACTTCGGAGTTGCC (SEQ ID NO:28), R-CACCTCGAGTGAATCGATTTGCCCCGC (SEQ ID NO:29)) were designed for PCR amplification. The PCR products of 3,119 bp fragment including aguA and xynA2 genes and 1,037 bp fragment of xynA2 gene were produced by PCR using the enzyme blend of ProofStart and Taq DNA polymerase (Qiagen) under the conditions: 1 cycle of 2 minutes at 98° C.; 5 cycles of 10 seconds at 95° C., 60 seconds at 55° and extension for 4 minutes at 68° C.; 30 cycles of 10 seconds at 95° C., 4 minutes at 68° C.; and an additional extension for 10 minutes at 72° C. The PCR products purified from agarose gel were double-digested with NcoI plus XhoI or BspLU 11I plus XhoI to produce the 3,119 bp and 1,026 bp fragments, and cloned into vector pET-32 digested with NcoI and XhoI.

In Vitro Protein Expression and Purification.

Constructs of aguA and xynA2 genes cloned into vector pET-32 were transformed into host *E. coli* Rosetta (DE3) containing pRare plasmid. Transformants were selected on LB plates containing 100 µg·ml$^{-1}$ of ampicillin and 34 µg·ml$^{-1}$ of chloramphenicol. Single colonies were inoculated into 100 ml of LB medium containing ampicillin and chloramphenicol and incubated overnight. The cells of an overnight culture were centrifuged and resuspended in 250 ml of fresh LB containing 200 µg·ml$^{-1}$ of ampicillin and 34 µg·ml$^{-1}$ of chloramphenicol for over-expression under the induction with 0.2 mM and 0.5 mM of IPTG for aguA and xynA2 genes at 23° C. for 2 h. The cells were harvested, suspended in 10 ml of His.Tag binding buffer without NaCl, and disrupted with 2 passages through a French Pressure Cell (SLM Instruments Inc.) at a differential pressure of 20,000 psi. This treatment was followed by sonication on ice for 2 min at power level 7 using a model W-185E Sonifier Cell Disruptor (Ultrasonics, Inc., NY). Cell lysates were purified on His.Tag columns (HiTrap Chelating HP, GE Healthcare Bio-Sciences Corp, Piscataway, N.J. 08855), binding in the Binding buffer (500 mM NaCl in 20 mM sodium phosphate buffer, pH 7.4) and eluting with the elution buffer (500 mM imidazole in the binding buffer) as described in the protocol provided by the company. The eluate from the His.Tag column was desalted on a PD-10 column (GE Healthcare Bio-Sciences Corp), and the protein was eluted with 50 mM NaOAc (pH6.0).

Determination of Activities and Substrate Specificities of AguA and XynA2

Recombinant AguA was assayed for enzyme activity at 37° C. in 50 mM NaOAc (pH6.0) buffer by determination of reducing termini on methylglucuronate residues released from aldouronates (Milner et al., 1967). Recombinant XynA2 activity was determined at 30° C. in the same buffer by the standard Nelson assay of reducing termini released from xylooligosaccharides (Nelson, 1944). One unit of enzyme activity is defined as the amount that releases 1 µmol reducing termini per min at the designated temperature. Protein concentrations were determined by the BCA assay kit using a bovine serum albumin standard as described above. Activities were also determined by quantification of substrates by HPLC. MeGAX$_1$ or MeGAX$_3$ was incubated as 88 nmol in a volume of 50 µl with enzyme (1 µg) in 50 mM sodium acetate (pH 6.0) for 30 min at 37° C. After heating in a boiling water bath for 10 min to stop the reaction, products were resolved on an Aminex HPX-87H (Bio-Rad) column eluted with 0.01 N H$_2$SO$_4$ and detected by differential refractometry.

Relative preferences and specificities of AguA for MeGAX$_1$, MeGAX$_2$, MeGAX$_3$ and MeGAX$_4$ as substrates were determined upon incubation of purified enzyme (1 µg/µl of protein) with 10 mM of substrate in 100 µl of reaction buffer (50 mM of sodium acetate, pH 6.0) at 30° C. for approximately 16 h. The digested products (20 µl of a complete digestion, 20 nmol equivalents of product) were spotted on a TLC plate (Silica gel 60, EM Laboratories, Inc.), along with 20 nmol of xylooligosaccharide (X$_1$, X$_2$, X$_3$ and X$_4$) and aldouronate (MeGAX$_1$, MeGAX$_2$, MeGAX$_3$ and MeGAX$_4$) standards. The plate was developed, stained and visualized as described above for analysis of media samples.

To determine the respective roles of AguA and XynA2 in processing aldouronates, the activities of XynA2 and AguA were evaluated individually and together with xylooligosaccharides (X$_2$, X$_3$ and X$_4$) and aldouronates (MeGAX$_2$, MeGAX$_3$ and MeGAX$_4$) as substrates. The purified enzyme(s) XynA2 (1.9 µg) or AguA (4.0 µg) with XynA2 (1.9 µg) were incubated in 50 µL of reaction buffer (50 mM of sodium acetate, pH 6.0) at 30° C. for 16 h and the reaction components were resolved by TLC and detected following the above procedures.

Optimal Temperature and pH for the Activities of α-glucuronidase (AguA) and XynA2.

To determine the optimal temperature, the purified AguA (6.0 µg) was incubated with 10 mM of MeGAX$_1$ in 200 µl of reaction in 50 mM of sodium acetate buffer (pH 6.0) for 30 min at different temperatures, 30° C., 40° C., 50° C., 60° C. and 70° C. Reactions assayed in triplicate for AguA activity by determination of uronic acid reducing termini (Milner et al., 1967), using D-glucuronic acid as a standard. To determine the optimal pH, the reactions were run in different buffers of pH 4.0 to 7.0 (50 mM, NaOAc buffer) and pH 7.1 to 8.5 (50 mM, Tris-HCl buffer) for 30 min at 37° C., and assayed as above.

To determine the optimal temperature of XynA2, the purified enzyme (10.0 µg) was incubated with 100.0 µg of xylotriose in 500 µl of reaction in 50 mM of sodium acetate buffer (pH 6.0) for 4 h at different temperature from 25° C. to 80° C. The digestion reaction was run in triplicate for colorimetric assay of XynA2 activity to assay the generation of new reducing termini as a measure of glycosidic bond cleavage, using D-xylose as a standard (Nelson, 1944). To determine the optimal pH, the reactions were run in different buffers of pH 5.0 to 6.5 (50 mM, NaOAc buffer) and pH 7.1 to 8.5 (100 mM, potassium phosphate buffer) for 4 h at 30° C.

Results

Growth and Consumption of Carbohydrate Substrates

Figure 9A:
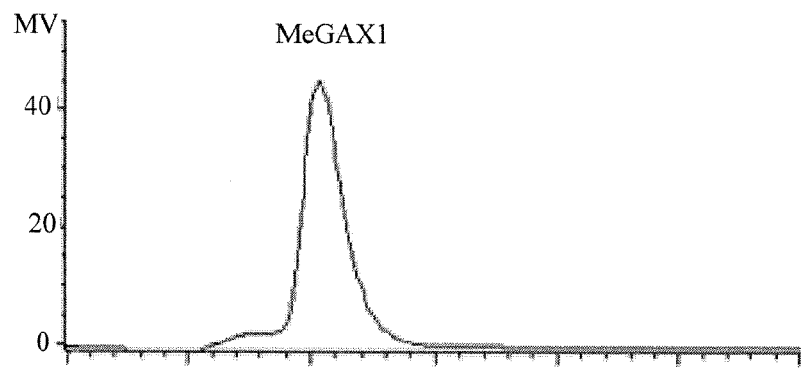
FIGS. 9A-9D. HPLC analysis of deglycosylation of aldouronates by recombinant AguA. Pure AguA (1 µg) was incubated with aldouronates in assay buffer (pH 6.0) at 30° C. for 30 min. The reaction components were resolved on a BioRad Aminex HPX 87H column eluted with 0.01 N H$_2$SO$_4$ and detected by differential refractometry. X-axis values indicate the elution time in minutes; Y-axis values indicate amounts determined by differential refractometry detected as millivolts.
Figure 9B:
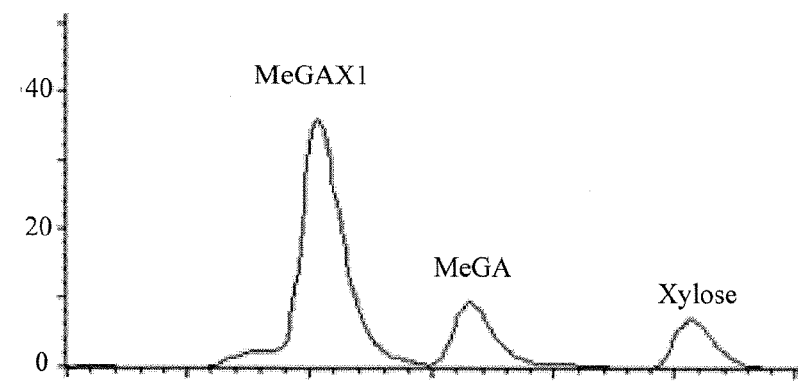
Figure 9C:
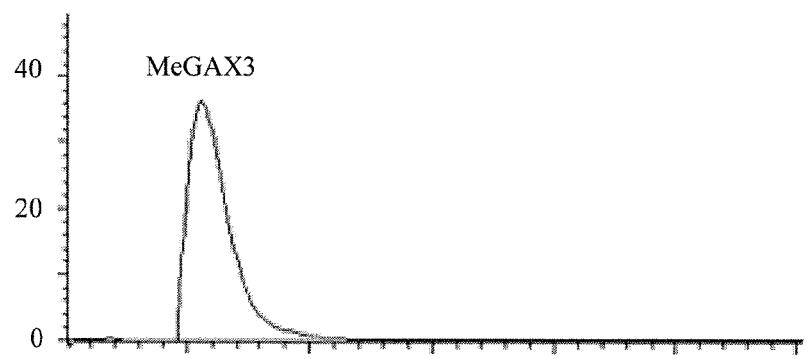
Figure 9D:
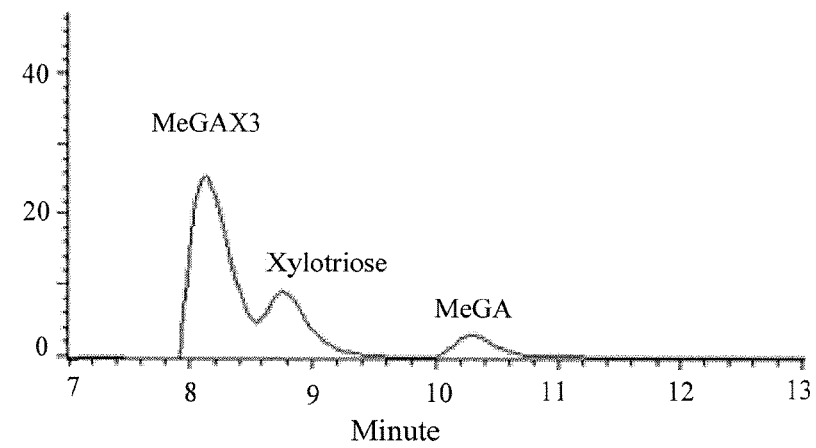

The *Paenibacillus* sp strain JDR-2 strain showed markedly different growth rates (FIG. 9A) with the polysaccharide compared to the aldouronates MeGAX$_1$ (generated by acid hydrolysis) or MeGAX$_3$ (generated by GH10 xylanase catalyzed hydrolysis). The rapid growth on MeGAX$_n$ between 8 to 20 h determined by OD$_{600}$ was followed by a rapid decline phase that indicated cell lysis, possibly associated with sporulation. A similar pattern with a slight temporal shift was observed for growth based upon the determination of total cell protein. The growth in media supplemented with MeGAX$_1$ and MeGAX$_3$ increased slowly and steadily from 8 to 34 h with a lower growth rate compared to growth on MeGAX$_n$, with growth patterns determined by total cell protein similar to those determined by OD$_{600}$ (data not shown). The utilization of substrates, determined by total carbohydrate or uronic acid, mirrored the growth curves for each substrate (FIG. 9B), indicating growth was quantitatively correlated with the consumption of each substrate.

Figure 10:
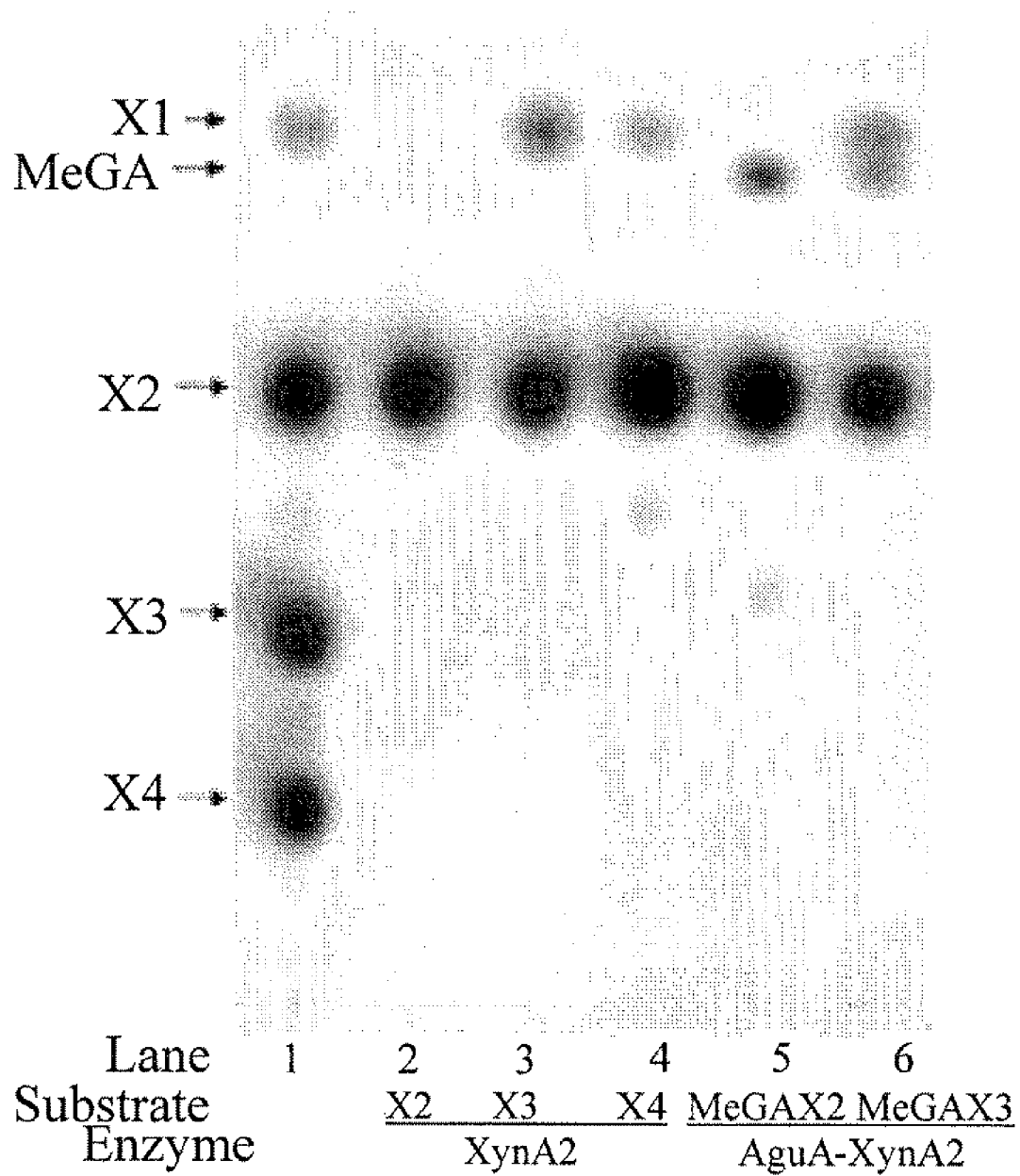
FIG. 10. TLC analysis of deglycosylation of xylosides by XynA2, and aldouronates by AguA with XynA2. Pure AguA and XynA2, (4.0 µg vs 1.9 µg), was incubated in assay buffer (pH 6.0) at 30° C. for 16 h and the reaction components were resolved by TLC and detected as descried in Materials and Methods. Lane 1: standards of X$_{1-4}$, 10 nmoles/each; Lane 2-4: xylobiose, xylotriose and xyloteterose incubated with XynA2; Lane 5-6: MeGAX$_2$ and MeGAX$_3$ cleaved by XynA2+AguA.

The regions of growth curves showing the highest rate of growth and substrate utilization were selected to compare the rates of utilization of the polysaccharide, MeGAX$_n$, with MeGAX$_1$ and MeGAX$_3$. The relationships between substrate utilization and time over this time frame provided a quantitative basis for this comparison as determined for the disappearance of total carbohydrate and uronic acid (FIG. 10), and similar rates of utilization were found for a given substrate using both assays. The slopes of the best fit curves relating substrate utilization to time were −0.0765 for MeGAX$_n$, −0.0334 for MeGAX$_1$, and −0.0203 for MeGAX$_3$. The respective rates of utilization of MeGAX$_n$, MeGAX$_1$, and MeGAX$_3$ were 149.8, 59.4 and 54.3 µg xylose equivalent·ml$^{-1}$·h$^{-1}$, and the respective growth rates determined for MeGAX$_n$, MeGAX$_1$, and MeGAX$_3$ sole carbon sources were 62.7, 4.3 and 4.8 µg cell protein·ml$^{-1}$·h$^{-1}$. While both aldouronates generated by enzyme mediated (MeGAX$_3$) or acid (MeGAX$_1$) served as effective carbon sources, the rate of growth on MeGAX$_n$ identified the marked preference for the polysaccharide.

Figure 7:
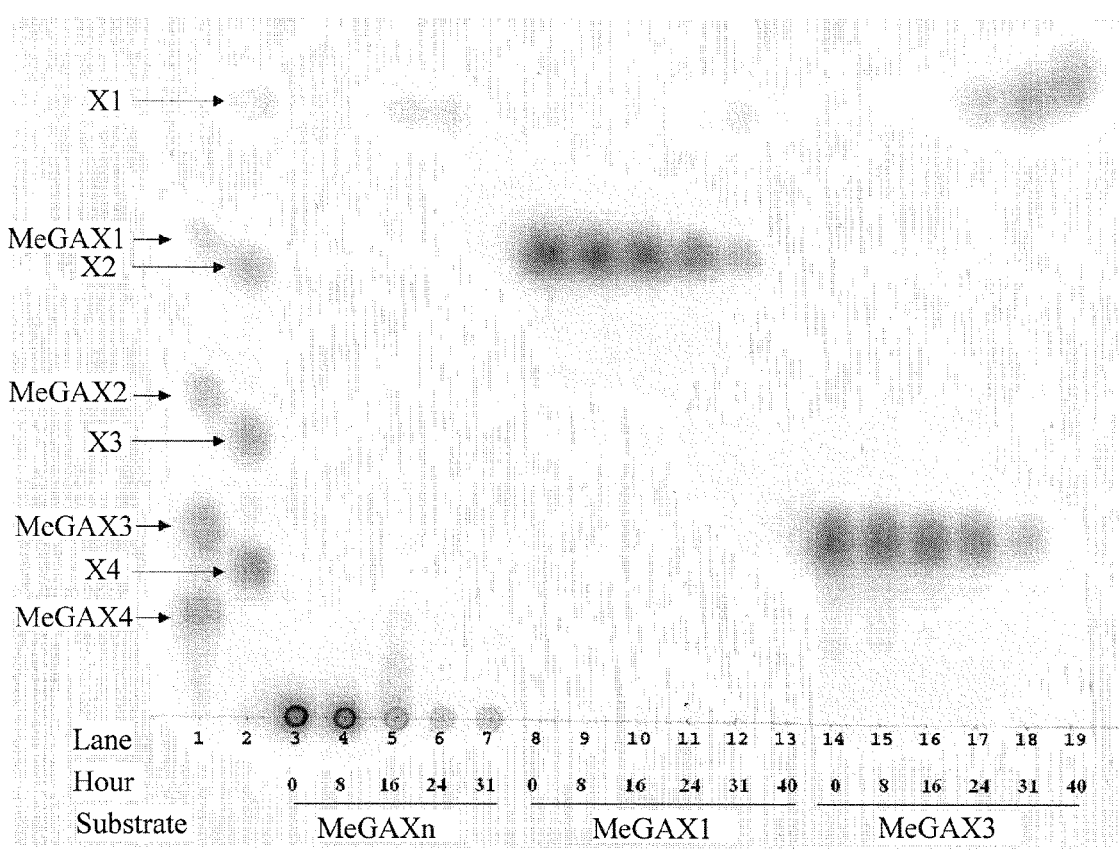
FIG. 7. Utilization of MeGAX$_1$, MeGAX$_3$ and sweetgum MeGAX$_n$ and product accumulation by *Paenibacillus* sp. JDR-2. Lane 1: standards of aldouronate, 10 nmoles each; Lane 2: standards of xylose and xylosides, 10 nmoles each; Lanes 3-19: supernates taken at 0, 8, 16, 24, and 32 h for cultures grown on MeGAX$_1$ (Lanes 3-7); taken at 0, 8, 16, 24, 32, and 40 h for cultures grown on MeGAX$_1$ (Lanes 8-13); MeGAX$_3$ (Lanes 14-19). Samples of supernates were spotted at indicated times that contained 100 nmol of xylose equivalents at 0 time. TLC plates were developed and samples detected as described in the Methods section.

TLC analysis of medium samples (FIG. 7) showed that MeGAX$_n$ was depolymerized and consumed within 31 hours with little of no accumulation of intermediate products. MeGAX$_1$ and MeGAX$_3$ as individual substrates for growth were completely utilized by 40 h without the appearance of intermediates prior to their assimilation.

Gene Cloning and Sequence Analysis

Genes cloned from PCR products generated from genomic DNA were identified by BLAST search and defined by identification of open reading frames. Based upon homolog comparisons, an aguA gene was identified encoding a 687 amino acid GH67 α-glucuronidase with a calculated molecular weight of 77,876 Da and a calculated pI of 5.4. Amino acid sequence identities with AguA homologs derived from GenBank entries were: 63% to *Aeromonas punctata*, 62% to *Geobacillus stearothermophilus* T-6, 61% to *Bacillus halodurans* C-125, and 57% to *Clostridium cellulolyticum* H10. This aguA gene was followed by a xynA2 gene encoding a 341 amino acid catalytic domain for a GH10 endoxylanase without a signal peptide sequence detectable with SignalP program. This XynA2 has a calculated molecular weight of 39,457 Da and a calculated pI of 5.3, and showed 60-61% amino acid sequence identity to GH10 xylanase catalytic domains presumed to function as an intracellular enzyme in other bacteria, e.g. *Geobacillus stearothermophilus* T-6 and *Thermotoga maritima* MSB8.

In Vitro Expression and Properties of AguA and XynA2

The expression of recombinant aguA and xynA2 in *E. coli* was evaluated by SDS-PAGE analysis of insoluble (cell pellets) and soluble (supernates) following French Pressure Cell lysis, sonication and centrifugation. Based upon stained gel patterns (data not shown), expression of aguA identified a predominant protein of 94.8 kDa with 20% in the cell pellet and 80% in the supernate. The expression of xynA2 and similar analysis identified predominant protein of 55.7 kDa with 20% in the pellet and 80% in the supernate. Following purification of soluble fractions on His-Tag resins and desalting on PD-10 columns, the yields of AguA and XynA2 were 24.9 mg·liter$^{-1}$ and 10.4 mg·liter$^{-1}$, respectively.

With MeGAX$_1$ as substrate, AguA activity at 37° C. was 4.69, 5.54, 5.11, 5.10, 3.55, 1.77, and 0.052 U·mg$^{-1}$ protein at pH 5.0, 5.5, 6.0, 6.5, 7.1, 7.5, and 8.0, respectively. At pH 6.0, AguA activity was 3.62, 4.82, 2.62, 0.60, and 0.34 U·mg$^{-1}$ protein at temperatures 30, 40, 50, 60, and 70° C., respectively. With xylotriose as substrate, XynA2 activity at 30° C. was 0.10, 0.13, 0.14, 0.13, 0.12, 0.12, and 0.11 U·mg$^{-1}$ protein at pH 5.0, 5.5, 6.0, 6.5, 7.0, 7.5 and 8.0 respectively. At pH 6.0, xynA2 activity was 0.13, 0.14, 0.134, 0.104, 0.084, 0.064, 0.061, 0.059, and 0.059 U·mg$^{-1}$ protein at temperatures 25, 30, 35, 40, 45, 50, 60, 70, and 80° C., respectively. AguA maintained 85% and XynA2 maintained 71% of their respective optimal activities at pH 5.0, and both showed significant activity at 50° C. (AguA, 54%; XynA2, 46%), supporting their application as moderately acid-tolerant and thermotolerant catalysts.

Products Generated by the Action of AguA and XynA2

Using the colorimetric assay, the specific activities of AguA released 4-O-methyl-D-glucuronate from aldobiouronate (MeGAX$_1$) and aldotetrauronate (MeGAX$_3$) at a concentration of 2 mM substrate were determined at pH 6.0, 37° C., to be 1.0 and 2.8 U·mg$^{-1}$ protein, respectively.

Figure 8:
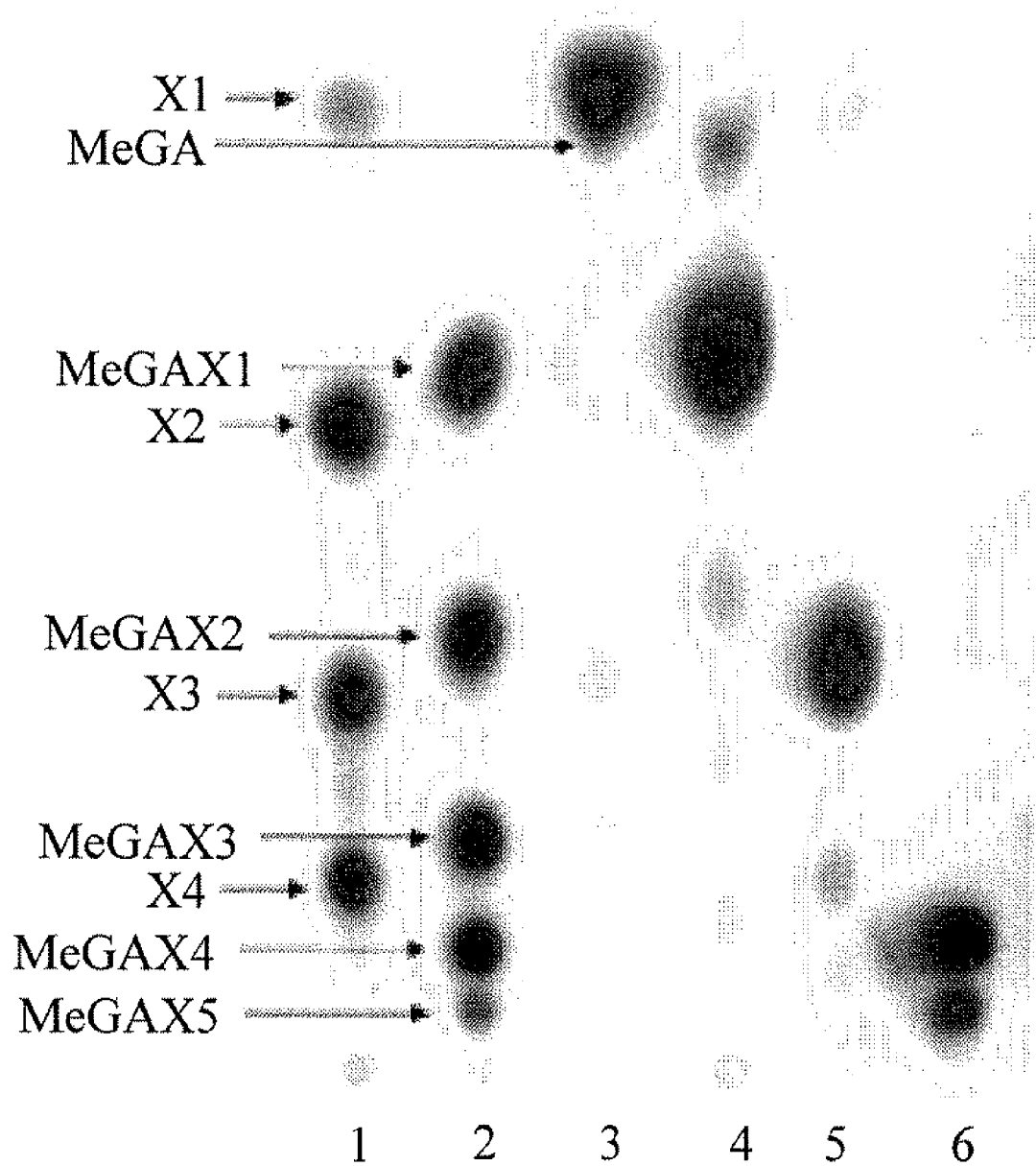
FIG. 8. TLC analysis of deglycosylation of aldouronic acids by recombinant AguA. Pure AguA (1 µg) was incubated in assay buffer (pH 6.0) at 30° C. for 16 h and the reaction components were resolved by TLC and detected as descried in Materials and Methods. Lane 1: standards of X$_{1-4}$, 20 nmoles each; Lane 2: standards of MeGAX$_{1-5}$, 20 mmoles each; Lanes 3-6: AguA incubated with MeGAX$_1$, MeGAX$_2$, MeGAX$_3$, and MeGAX$_4$, respectively.

With TLC analysis (FIG. 8), the activity of AguA on different aldouronates (MeGAX$_{1-4}$) showed that AguA cleaved MeGAX$_{1-3}$ to MeGA, and xylose, xylobiose and xylotriose, respectively. The MeGA displayed a mobility slightly less than xylose and was not resolved from xylose in the products generated from MeGAX$_1$. The mobilities of xylose, xylobiose, and xylotriose as standards (Lane 1) were slightly less than found for the saccharides generated by the action of AguA on MeGAX$_1$, MeGAX$_2$, and MeGAX$_3$ (Lanes 3, 4, 5), possibly affected by the components of the assay reaction. AguA exhibited no activity on MeGAX$_4$ or MeGAX$_5$ generated by a GH11 endoxylanase from *Trichoderma longibrachiatum*. HPLC analysis of reaction mixtures containing either MeGAX$_1$ or MeGAX$_3$ as substrates quantitatively confirmed the activity of AguA on both of these aldouronates (FIG. 9). AguA cleaved MeGAX$_1$ (FIG. 9B) to generate stoichiometric quantities of MeGA (peak: 10.29 min) and xylose (peak: 12.12 min). AguA cleaved MeGAX$_3$ (FIG. 9D) into xylotriose (peak: 8.75 min) and MeGA (peak: 10.29 min).

XynA2 is an endoxylanase classified as a member of glycohydrolase family GH10 lacking a secretion signal sequence that is active with methylglucuronoxylan as substrate (data not shown). Using xylobiose, xylotriose and xylotetraose as substrates, the TLC results (FIG. 10) showed that XynA2 cleaved xylotriose and xylotetraose to form xylose and xylobiose as limit products. With xylotriose as substrate and HPLC analysis of products, XynA2 catalyzed the formation of xylobiose equivalent to 67% and xylose equivalent to 33% of total amount of products (and equivalent to the starting amount of xylotriose) indicating that one molecule of xylotriose produced one xylose and one xylobiose. With xylotetraose as substrate, XynA2 catalyzed the formation of xylobiose equivalent to 83% of total amount of products, and xylose equivalent to 17%. Based on these results, XynA2 was able to cleave xylotetraose to form xylobiose or xylotriose and xylose, and then cleave the xylotriose to form xylobiose and xylose. With either substrate, xylobiose was a limit product requiring further processing for metabolism. The combined activities of AguA and XynA2 showed formation of MeGA and xylobiose from MeGAX$_2$ and MeGA, xylobiose and xylose from MeGAX$_3$ (FIG. 10), supporting their cooperative role in the intracellular processing the aldouronate MeGAX$_3$ derived from the extracellular action of the multimodular cell-associated XynA1.

All patents, patent applications, provisional applications, and publications referred to or cited herein are incorporated by reference in their entirety, including all figures and tables, to the extent they are not inconsistent with the explicit teachings of this specification.

TABLE 1

List of nucleotide sequences of primers used

| Primer | Nucleotide sequence | |
|---|---|---|
| PF54 | CGAGAGAGAGACATTCCTTATTACG | (SEQ ID NO: 30) |
| PR569 | CATCTGGTTGGTATGCTCCATCG | (SEQ ID NO: 31) |
| rre178f | GTGCTGGACGGATTGGAGCTTA | (SEQ ID NO: 32) |
| rre459r | CTCCGAGAACTGGCCTTGAACA | (SEQ ID NO: 33) |
| sbp1081f | AACTCGTATGGCGTAGGCAACC | (SEQ ID NO: 34) |
| sbp1361r | TGGCCTGTATAGTCGCTCCAGA | (SEQ ID NO: 35) |
| agua1069f | CGGACGCTTCAAGGACAATGTG | (SEQ ID NO: 36) |
| agua1354r | GGCCGTAATGCCGCTATGAGTA | (SEQ ID NO: 37) |
| xyl247f | CATACGCTGGTGTGGCACAATC | (SEQ ID NO: 38) |
| xyl623r | CCGTGAATCGGCACTTGCTTAG | (SEQ ID NO: 39) |
| bex948f | GGACAAGTCGGTGACCACCAAG | (SEQ ID NO: 40) |
| bex1291r | CTTGCGCCATCGCCGTTACAAG | (SEQ ID NO: 41) |
| xynA1-2237f | GCGTCGGAATGCAAGGCCATTA | (SEQ ID NO: 42) |
| xynA1-2503r | TCTCGGCTCTCCAGCTTGTGTT | (SEQ ID NO: 43) |
| amp10f | GATCTGGCAGCTTCCTGCATTC | (SEQ ID NO: 44) |
| amp204r | TCCAGTCCGCGGCTCTTATCAA | (SEQ ID NO: 45) |
| oxr535f | TCACGGCGCGAACACTTATCTC | (SEQ ID NO: 46) |
| oxr774r | GCTCATCACAGGCGGAAGGTAT | (SEQ ID NO: 47) |
| perm-agua791f | TAACGGCGGTTACGCCAACCTC | (SEQ ID NO: 48) |
| perm-agua81r | CCAGCCTGCGTATTGCTCCAAG | (SEQ ID NO: 49) |

TABLE 2

Identification of the relevant xylanolytic genes in the 15 kb genomic segment

| ORF | Protein | COG# | Function | E value[b] | Homologous protein/% identity[c] |
|---|---|---|---|---|---|
| yesN[a] | YesN | 4753 | Response regulator containing CheY-like receiver domain and AraC-type DNA-binding domain [Signal transduction mechanisms] | 3e−51 | *Bacillus subtilus* subsp. *subtilus* str. 168, GeneID: 938764/40% (64/159) |
| yesM[a] | YesM | 2972 | Predicted signal transduction protein with a C-terminal ATPase domain [Signal transduction mechanisms] | 1e−48 | *Bacillus subtilus* subsp. *subtilus* str. 168, GeneID: 936078/23% (138/592) |
| lplA[a] | UgpB | 1653 | ABC-type sugar transport system, periplasmic component [Carbohydrate transport and metabolism] | 4e−10 | *Bacillus subtilus* subsp. *subtilus* str. 168, GeneID: 936079/25% (49/191) |
| lplB[a] | LplB | 4209 | ABC-type polysaccharide transport system, permease component [Carbohydrate transport and metabolism] | 3e−92 | *Bacillus subtilus* subsp. *subtilus* str. 168, GeneID: 936088/39% (112/285) |
| ytcP[a] | UgpE | 0395 | ABC-type sugar transport system, permease component [Carbohydrate transport and metabolism] | 9e−41 | *Bacillus subtilus* subsp. *subtilus* str. 168, GeneID: 938095/34% (102/294) |
| aguA | AguA | pfam03648 | Glycosyl hydrolase family 67. Family of alpha-glucuronidase. | 0.0 | *Geobacillus stearothermophilus* T-6, Alpha-glucuronidase Chain A, gi: 37926810/ 67% (422/680) |
| xynA2 | XynA2 | smart00633 | Endoxylanase, Glycosyl hydrolase family 10 | 8e−90 | *Geobacillus stearothermophilus*, Intra-cellular xylanase IXT6, gi: 114054545/ 60% (199/327) |
| xynB[a] | XynB | pfam04616/ 3507 | Arabinofuranosidase Glycohydrolase family 43/ Beta-xylosidase. | 2e−74/ 8e−86 | *Geobacillus stearothermophilus*, Intra-cellular xylanase IXT6, XynB, gi: 114054567/32% (178/540) |

[a]Gene name is assigned to that closest in homology found in *Bacillus subtilus*, *subtilus* str. 168.
[b]similarity to the functional protein family assignment as determined by CD SEARCH, NCBI.
[c]Percent identity is the number of residues of the major portion of the query protein identical to those of the subject protein as determined by the NCBI BLAST program.

TABLE 3

Candidate CcpA binding sites and their locations 5' of aldouronate-utilization genes in *Paenibacillus* sp. JDR-2

| Binding site sequence & Distance from translation start site | SEQ ID NO: | Homology ratio to canonical sequence (Cho et al., 1999) | Gene |
|---|---|---|---|
| 5'-TGWAANCGNTNWCA | 50 | 14/14 | Cho et al., 1999 |
| 5'-TGAAATCGCTTACA[a]---145nt---ATG--- | 51 | 14/14 | yesN |
| 5'-TGAAAGTGCTTACA[a]---38nt---ATG--- | 52 | 13/14 | lplA |
| 5'-ATG---146nt---TGAAGCGGATGACA[b]--- | 53 | 12/14 | lplA |
| 5'-TGAACCGCTGGCAG[b]---183nt---ATG--- | 54 | 12/14 | xynA2 |
| 5'-TGTAAGCGCTTAAT[b]---30nt---ATG--- | 55 | 12/14 | xynA1 |

[a]identified by PPP (Prokaryotic Promoter Prediction) program (Groningen Biomolecular Sciences and Biotechnology Institute, Haren, the Netherlands, http://bioinformatics.biol.rug.nl/websoftware/ppp/ppp_start.php)
[b]identified by manual scanning of the upstream region of these genes

TABLE 4

Activities of the aldouronate-utilization gene products isolated from *Paenibacillus* sp. JDR-2

| SEQ ID NO: 1 | yesN | CheY-like, Ara C type response regulator |
| SEQ ID NO: 3 | yesM | Histidine kinase-type transduction protein |
| SEQ ID NO: 5 | lplA | Substrate binding protein |
| SEQ ID NO: 7 | lplB | Lipoprotein |
| SEQ ID NO: 9 | ytcP | Permease activity |
| SEQ ID NO: 11 | aguA | GH67 α-glucuronidase activity |
| SEQ ID NO: 13 | xynA2 | GH10 xylanase activity |
| SEQ ID NO: 15 | xynB | GH43 β-xylosidase activity |
| SEQ ID NO: 17 | | NADH-dependent flavin oxidoreductase |

TABLE 5

List of start and stop nucleotide number of genes coded in the two sequences EU024644 (SEQ ID NO: 21) and AJ938162 (SEQ ID NO: 19)

| Gene | Start | Stop |
| --- | --- | --- |
| GenBank # EU024644 | | |
| yesN | 620 | 2188 |
| yesM | 2204 | 3922 |
| lplA | 4056 | 5768 |
| lplB | 5858 | 6829 |
| ytcP | 6869 | 7789 |
| aguA | 7886 | 9949 |
| xynA2 | 9977 | 11002 |
| xynB | 10999 | 12564 |
| oxidoreductase | 12775 | 13899 |
| hypothetical protein | 14019 | 14726 |
| GenBank #AJ938162 | | |
| xynA1 | 1 | 4401 |

NB. The AJ938162 sequence is 4401 nucleotides long. Therefore the coding sequence is the entire nucleotide sequence of that submission.

REFERENCES

U.S. Pat. No. 6,342,362
U.S. Pat. No. 6,407,213
U.S. Pat. No. 6,417,337
U.S. Pat. No. 4,816,567
U.S. Pat. No. 6,319,691
U.S. Pat. No. 6,277,375
U.S. Pat. No. 5,643,570
U.S. Pat. No. 5,565,335
U.S. Pat. No. 5,561,071
U.S. Pat. No. 5,753,439
U.S. Pat. No. 6,214,545
Altschul, S. F. et al. (1990) "Basic Local Alignment Search Tool" *J. Mol. Biol.* 215(3):403-410.
Alwine, J. C. et al. (1977) "Method for detection of specific RNAs in agarose gels by transfer to diazobenzyloxymethyl-paper and hybridization with DNA probes" *Proc. Natl. Acad. Sci.* 74:5350-5354.
Altendorf et al. (1999—WWW, 2000) "Structure and Function of the $F_0$ Complex of the ATP Synthase from *Escherichia Coli*" *J. of Experimental Biology* 203:19-28.
Ausubel, M. et al. (1989) Current Protocols in Molecular Biology, Green Publishing Associates and Wiley Interscience, N.Y.
Baneyx, F. (1999) "Recombinant Protein Expression in *Escherichia coli*" *Biotechnology* 10:411-21.
Bell, K. S., A. O. Avrova, M. C. Holeva, L. Cardle, W. Morris, W. DeJong, I. K. Toth, R. Waugh, G. J. Bryan, and P. R. J. Birch (2002) "Sample sequencing of a selected region of the genome of *Erwinia* carotovora subsp. *atroseptica* reveals candidate phytopathogenicity genes and allows comparison with *Escherichia coli*" *Microbiology* 148:1367-1378.
Beltz, G. A. et al. (1983) "Isolation of multigene families and determination of homologies by filter hybridization methods" *Methods of Enzymology*, R. Wu, L. Grossman and K. Moldave [eds.] Academic Press, New York 100:266-285.
Bendtsen J. D., H. Nielsen, G. von Heijne, and S. Brunak (2004) "Improved prediction of signal peptides-SignalP 3.0" *J. Mol. Biol.* 340:783-795.
Berchtold, M. W. (1989) "A simple method for direct cloning and sequencing cDNA by the use of a single specific oligonucleotide and oligo(dT) in a polymerase chain reaction (PCR)" *Nuc. Acids. Res.* 17:453.
Bertani, G. (1951) "Studies on lysogenesis. I. The mode of phage liberation by lysogenic *Escherichia coli*". *J. Bacteriol.* 62:293-300.
Bianchi, N. et al. (1997) "Biosensor technology and surface plasmon resonance for real-time detection of HIV-1 genomic sequences amplified by polymerase chain reaction" *Clin. Diagn. Virol.* 8(3):199-208.
Biely P., J. Hirsch, D. C. la Grange, W. H. van Zyl, and B. A. Prior (2000) "A chromogenic substrate for a beta-xylosidase-coupled assay of alpha-glucuronidase" *Anal. Biochem.* 286:289-94.
Bluemenkrantz, N., and G. Asboe-Hansen (1973) "New method for quantitative determination of uronic acids" *Anal. Biochem.* 54:484-489.
Bounias, M. (1980) "N-(1-naphthyl)ethylenediamine dihydrochloride as a new reagent for nanomole quantification of sugars on thin-layer plates by a mathematical calibration process" *Anal. Biochem.* 106:291-295.
Cheung, A. L., K. J. Eberhardt, and V. A. Fischetti (1994) "A method to isolate RNA from Gram-positive bacteria and mycobacteria" *Anal. Biochem.* 222:511-514.
Cho, S-G and Y-J Choi (1999) "Catabolite repression of the xylanase gene (xynA) Expression in *Bacillus stearothermophilus* No. 236 and *B. subtilus*" *Biosci. Biotechnol. Biochem.* 63:2053-2058.
Clackson, T. et al. (991) "Making Antibody Fragments Using Phage Display Libraries" *Nature* 352:624-628.
Collins T., C. Gerday, and G. Feller (2005) "Xylanases, xylanase families and extremophilic xylanases" *FEMS Microbiol. Rev.* 29:3-23.
Conners, S. B., C. I. Montero, D. A. Comfort, K. R. Shockley, M. R. Johnson, S. R. Chhabra, and R. M. Kelly (2005) "An expression-driven approach to the prediction of carbohydrate transport and utilization regulons in the hyperthermophilic bacterium *Thermotoga maritima*" *J. Bacteriol.* 187:7267-7282.
Dien, B. S., M. A. Cotta, and T. W. Jeffries (2003) "Bacteria engineered for fuel ethanol production: current status" *Appl. Microbiol. Biotechnol.* 63:258-266.
Dubois, M., K. A. Gilles, J. K. Hamilton, P. A. Rebers, and F. Smith (1956) "Colorimetric method for the determination of sugars and related substances" *Anal. Chem.* 28:350-356.
Eihauer, A. et al. (2001) "The FLAG™ Peptide, a Versatile Fusion Tag for the Purification of Recombinant Proteins" *J. Biochem Biophys Methods* 49:455-65.
Gish, W. et al. (1993) "Identification of protein coding regions by database similarity search" *Nature Genetics* 3:266-272.
Golan, G., D. Shallom, A. Teplitsky, G. Zaide, S Shulami, T. Baasov, V. Stojanoff, A. Thompson, Y. Shoham, and G. Shoham (2004) "Crystal structures of *Geobacillus stearothermophilus* α-glucuronidase complexed with its substrate and products" *J. Biol. Chem.* 279:3014-3024.

Higgins, D. G. et al. (1996) "Using CLUSTAL for multiple sequence alignments" *Methods Enzymol.* 266:383-402.

Ingram, L. O., H. C. Aldrich, A. C. Borges, T. B. Causey, A. Martinez, F. Morales, A. Saleh, S. A. Underwood, L. P. Yomano, S. W. York, J. Zaldivar, and S. Zhou (1999) "Enteric bacterial catalysts for fuel ethanol production" *Biotechnol Prog* 15:855-66.

Jones, C. et al. (1995) "Current Trends in Molecular Recognition and Bioseparation" *J. of Chromatography A.* 707:3-22.

Keller, G. H., M. M. Manak (1987) *DNA Probes*, Stockton Press, New York, N.Y., pp. 169-170.

Kohler, G. et al. (1975) "Continuous Cultures of Fused Cells Secreting Antibody of Predefined Specificity" *Nature* 256 (5517):495-497.

Kuhad, R. C., A. Singh, and K. E. Eriksson (1997) "Microorganisms and enzymes involved in the degradation of plant fiber cell walls" *Adv. Biochem. Eng. Biotechnol.* 57:45-125.

Lloyd, T. A., and C. E. Wyman (2005) "Combined sugar yield for dilute sulfuric acid pretreatment of corn stover followed by enzymatic hydrolysis of the remaining solids" *Biores. Technol.* 96:1967-1977.

Maniatis, J.-M. et al. (1982) *Molecular Cloning: A Laboratory Manual*, Cold Spring Harbor Laboratory, New York.

Margolin, W. (2000) "Green Fluorescent Protein as a Reporter for Macromolecular Localization in Bacterial Cells" *Methods* 20:62-72.

Marks, J. D. et al. (1991) "By-Passing Immunization: Human Antibodies from V-Gene Libraries Displayed on Phage" *J. Mol. Biol.* 222(3):581-597.

McLaughlin, J. R., C. L. Murray, and J. C. Rabinowitz (1981) "Unique features in the ribosome binding site sequence of the Gram-positive *Staphylococcus aureus* β-lactamase gene" *J. Biol. Chem.* 256:11283-11291.

Melton, D. A. et al. (1984) "Efficient In Vitro Synthesis of Biologically Active RNA and RNA Hybridization Probes From Plasmids Containing a Bacteriophage SP6 Promoter" *Nuc. Acids Res.* 12:7035-7036.

Milner, Y. and Avigad, G. (1967) "A copper reagent for the determination of hexuronic acids and certain ketohexoses" *Carbohyd. Res.* 4:359-361.

Morrison, S. L. et al. (1984) "Chimeric Human Antibody Molecules: Mouse Antigen-Binding Domains with Human Constant Region Domains" *Proc. Natl. Acad. Sci. USA* 81:6851-6855.

Nagy, T., D. Nurizzo, G. J. Davies, P. Biely, J. H. Lakey, D. N. Bolam, and H. Gilbert (2003) "The α-glucuronidase, GlcA67A, of *Cellvibrio japonicus* utilizes the carboxylate and methyl groups of aldobiouronic acid as important substrate recognition determinants" *J. Biol. Chem.* 278:20286-20292.

Nelson, N. (1944) "A photometric adaptation of the Somogyi method for the determination of glucose" *J. Biol. Chem.* 153:375-380.

Nelson, K. E., R. A. Clayton, S. R. Gill, M. L. Gwinn, R. J. Dodson, D. H. Haft, E. K. Hickey, J. D. Peterson, W. C. Nelson, K. A. Ketchum, L. McDonald, T. R. Utterback, J. A. Malek, K. D. Linher, M. M. Garrett, A. M. Stewart, M. D. Cotton, M. S. Pratt, C. A. Phillips, D. Richardson, J. Heidelberg, G. G. Sutton, R. D. Fleischmann, O. White, S. L. Salzberg, H. O, Smith, J. C. Venter, and C. M. Fraser (1999) "Evidence for lateral gene transfer between Archaea and bacteria from genome sequence of *Thermotoga maritima*" *Nature* 399:323-329.

Nong G., V. Chow, J. Rice, F. St. John, and J. Preston (2005) "An aldouronic acid-utilization operon in a *Paenibacillus* sp. encodes an alpha-glucuronidase with activity on aldouronic acids generated by acid and enzyme mediated digestion of methyglucuronoxylan" Abstracts of the 105th National Meetings of the American Society of Microbiology in Atlanta Ga.

Pearson, W. R. et al. (1988) "Improved Tools for Biological Sequence Comparison" *Proc. Natl. Acad. Sci. USA* 85(8):2444-2448.

Pietu, G. et al. (1996) "Novel gene transcripts preferentially expressed in human muscles revealed by quantitative hybridization of a high density cDNA array" *Genome Research* 6(6):492-503.

Pincus, S., P. W. Mason, E. Konishi, B. A. Fonseca, R. E. Shope, C. M. Rice, and E. Paoletti (1992) "Recombinant vaccinia virus producing the prM and E proteins of yellow fever virus protects mice from lethal yellow fever encephalitis" *Virology* 187:290-297.

Preston, J. F., J. C. Hurlbert, J. D. Rice, A. Ragunathan, and F. J. St. John (2003) "Microbial strategies for the depolymerization of glucuronoxylan: leads to biotechnological applications of endoxylanases" pp. 191-210. In S. D. Mansfield and J. N. Sadler (ed.), Applications of enzymes to lignocellulosics. American Chemical Society, Washington D.C.

Puig, O. et al. (2001) "The Tandem Affinity Purification (TAP) Method: A General Procedure of Protein Complex Purification" *Methods* 24:218-29.

Quentin, Y., G. Fichant, and F. Denizot (1999) "Inventory, assembly and analysis of *Bacillus subtilus* ABC transport systems" *J. Mol. Biol.* 287:467-484.

Sambrook, J. et al (1989) Molecular Cloning, A Laboratory Manual, Second Edition, Cold Spring Harbor Press, N.Y., pp. 9.47-9.57.

Sassenfeld, H. M. (1990) "Engineering Proteins for Purification" *TibTech* 8:88-93.

Schena, M. et al. (1995) "Quantitative Monitoring of Gene Expression Patterns With a Complementary DNA Microarray" *Science* 270:467-470.

Schena, M. et al (1996a) "Parallel human genome analysis: microarray-based expression monitoring of 1000 genes" *Proc. Natl. Acad. Sci. U.S.A.* 93(20):10614-10619.

Schena, M. (1996b) "Genome analysis with gene expression microarrays" *BioEssays* 18(5):427-431.

Schneider, E. (2001) "ABC transporters catalyzing carbohydrate uptake" *Res. Microbiol.* 152:303-310.

Sheibani, N. (1999) "Prokaryotic Gene Fusion Expression Systems and Their Use in Structural and Functional Studies of Proteins" *Prep. Biochem. & Biotechnol.* 29(1):77-90.

Shulami, S., O. Gat, A. L. Sonenshein, and Y. Shoham (1999) "The glucuronic acid-utilization gene cluster from *Bacillus stearothermophilus* T-6" *J. Bacteriol.* 181:3695-3704.

Shulami S., G. Zaide, G. Zolotnitsky, Y. Langut, G. Feld, A. L. Sonenshein, and Y. Shoham (2007) "A two-component system regulates the expression of an ABC transporter for xylo-oligosaccharides in *Geobacillus stearothermophilus*" *Appl. Environ. Microbiol.* 73:874-84.

Skerra, A. et al. (1999) "Applications of a Peptide Ligand for Streptavidin: the Strep-tag" *Biomolecular Engineering* 16:79-86.

Smith, C. (1998) "Cookbook for Eukaryotic Protein Expression: Yeast, Insect, and Plant Expression Systems" *The Scientist* 12(22):20.

Smyth, G. K. et al. (2000) "Eukaryotic Expression and Purification of Recombinant Extracellular Matrix Proteins Carrying the Strep II Tag" *Methods in Molecular Biology* 139:49-57.

Suggs, S. V. et al (1981) *ICN-UCLA Symp. Dev. Biol. Using Purified Genes*, D. D. Brown [ed.], Academic Press, New York, 23:683-693.

Sunna, A. and G. Antranikian (1997) "Xylanolytic enzymes from fungi and bacteria" *Crit. Rev. Biotechnol.* 17:39-67.

St. John, F., J. D. Rice, and J. F. Preston (2006) "*Paenibacillus* sp. strain JDR-2 and xynA$_1$: a novel system for methylglucuronoxylan utilization" *Appl. Environ. Microbiol.* 72:1496-1506.

Takami, H., K. Nakasone, Y. Takaki, G. Maeno, R. Sasaki, N. Masui, F. Fuji, C. Hirama, Y. Nakamura, N. Ogasawara, S. Kuhara, K. Horikoshi (2000) "Complete genome sequence of the alkaliphilic bacterium *Bacillus halodurans* and genomic sequence comparison with *Bacillus subtilis*" *Nucleic Acids Res.* 28:4317-31.

Thompson, J. et al. (1994) "Clustal-W: *improving the sensitivity of progressive multiple sequence alignment through sequence weighting, position specific gap penalties and weight matrix choice*" *Nucleic Acids Res.* 22(2):4673-4680.

Unger, T. F. (1997) "Show Me the Money: Prokaryotic Expression Vectors and Purification Systems" *The Scientist* 11(17):20.

Wei, C. F. et al. (1983) "Isolation and comparison of two molecular species of the BAL 31 nuclease from *Alteromonas espejiana* with distinct kinetic properties" *J. Biol. Chem.* 258:13506-13512.

Zhou, S, and L. O. Ingram (2001) "Simultaneous saccharification and fermentation of amorphous cellulose to ethanol by recombinant *Klebsiella oxytoca* SZ21 without supplemental cellulase" *Biotechnol. Lett.* 23:1455-1462.

Zucker M. and L. Hankin (1970) "Regulation of pectate lyase synthesis in *Pseudomonas fluorescens* and *Erwinia carotovora*" *J Bacteriol.* 104:13-8.

We claim:

1. An isolated nucleic acid comprising a polynucleotide that encodes a polypeptide comprising the amino acid sequence of SEQ ID NO: 12, wherein said polypeptide has α-glucuronidase activity.

2. The isolated nucleic acid of claim 1, wherein said polynucleotide comprises the nucleotide sequence of SEQ ID NO: 11.

3. A genetic construct comprising the polynucleotide of claim 1.

4. The genetic construct of claim 3, wherein said polynucleotide comprises the nucleotide sequence of SEQ ID NO: 11.

5. A vector comprising the polynucleotide of claim 1.

6. The vector of claim 5, wherein said polynucleotide comprises the nucleotide sequence of SEQ ID NO: 11.

7. A host cell transformed with the nucleic acid of claim 1.

8. The host cell of claim 7, wherein said nucleic acid comprises a polynucleotide comprising the nucleotide sequence of SEQ ID NO: 11.

9. The host cell of claim 7, wherein said host cell is a *Bacillus* spp.

10. The host cell of claim 9, wherein said *Bacillus* spp is *Bacillus coagulans*.

11. A probe that hybridizes with the nucleic acid of claim 1.

12. The probe of claim 11, wherein said probe hybridizes with the nucleotide sequence of SEQ ID NO: 11.

13. An isolated polynucleotide that hybridizes under intermediate stringency or high stringency conditions to the nucleic acid of claim 1, wherein said intermediate or high stringency conditions comprise a hybridization step at 60° C. in the presence of a 5×SSC buffer and washes performed in a solution containing 2×SSC at 50° C. or a hybridization step at 65° C. in the presence of SSC buffer, 1×SSC corresponding to 0.15M NaCl and 0.05 M Na citrate, washes at 37° C. for 1 hour in a solution containing 2×SSC, 0.01% PVP, 0.01% Ficoll, and 0.01% BSA, followed by a wash in 0.1×SSC at 50° C. for 45 minutes, respectively.

14. The isolated polynucleotide of claim 13, wherein said nucleic acid comprises the nucleotide sequence of SEQ ID NO: 11.

15. A composition comprising a host cell transformed with a polynucleotide that encodes a polypeptide comprising the amino acid sequence of SEQ ID NO: 12, wherein said polypeptide has α-glucuronidase activity.

16. The composition of claim 15, wherein said host cell is contained in a solid medium.

17. The composition of claim 16, wherein said medium is a liquid medium.

18. An isolated nucleic acid that comprises a polynucleotide, wherein said polynucleotide is the full complement of the polynucleotide of claim 1.

* * * * *

UNITED STATES PATENT AND TRADEMARK OFFICE
CERTIFICATE OF CORRECTION

| | | |
|---|---|---|
| PATENT NO. | : 8,119,367 B2 | Page 1 of 1 |
| APPLICATION NO. | : 12/256155 | |
| DATED | : February 21, 2012 | |
| INVENTOR(S) | : James Faulkner Preston et al. | |

It is certified that error appears in the above-identified patent and that said Letters Patent is hereby corrected as shown below:

Column 3,
Lines 26-27, "MeGAX$_n$ (open triangles)" should read --MeGAX$_1$ (open triangles)--.
Lines 28-29, "MeGAX$_n$ (closed triangles)" should read --MeGAX$_1$ (closed triangles)--.
Line 40, "MeGAX$_1$" should read --MeGAX$_n$--.
Line 51, "20 mmoles" should read --20 nmoles--.

Column 6,
Line 37, "azoloformans" should read --azotoformans--.
Line 54, "schottinulleri" should read --schottmulleri--.

Column 17,
Lines 10-11, "aguA1069f and aguA1354r" should read --agua1069f and agua1354r--.
Line 17, "perm-aguA791f" should read --perm-agua791f--.
Line 17, "perm-aguA81r" should read --perm-agua81r--.

Column 20,
Line 10, "perm-aguA791f and perm-aguA81r" should read --perm-agua791f and perm-agua81r--.

Column 21,
Line 24, "Thermologa" should read --Thermotoga--.

Signed and Sealed this
Fifteenth Day of May, 2012

David J. Kappos
*Director of the United States Patent and Trademark Office*

SEQUENCE LISTING

```
<160> NUMBER OF SEQ ID NOS: 55

<210> SEQ ID NO 1
<211> LENGTH: 1569
<212> TYPE: DNA
<213> ORGANISM: Paenibacillus sp.
<220> FEATURE:
<221> NAME/KEY: CDS
<222> LOCATION: (1)..(1569)

<400> SEQUENCE: 1 atg tac aaa gtg tta ttg gtg gat gat gag att ttt gtg cgc aaa ggg      48
Met Tyr Lys Val Leu Leu Val Asp Asp Glu Ile Phe Val Arg Lys Gly
1               5                   10                  15 tta agg aat tta ata gac tgg gaa tcg ctt ggc tat gaa att tgc gat      96
Leu Arg Asn Leu Ile Asp Trp Glu Ser Leu Gly Tyr Glu Ile Cys Asp
            20                  25                  30 gaa gcg ggt aac gga cag gaa gca tta gag aaa ata cag ctg att aag     144
Glu Ala Gly Asn Gly Gln Glu Ala Leu Glu Lys Ile Gln Leu Ile Lys
        35                  40                  45 cct gat ctc gtt atc gcg gat atc cgg atg cca gtg ctg gac gga ttg     192
Pro Asp Leu Val Ile Ala Asp Ile Arg Met Pro Val Leu Asp Gly Leu
    50                  55                  60 gag ctt atc cgc aag gtt acc gag gag ggc gta cat agc ccg acc ttt     240
Glu Leu Ile Arg Lys Val Thr Glu Glu Gly Val His Ser Pro Thr Phe
65                  70                  75                  80 att atc gtc agc ggg tat cat gat ttc cag tac gcg cag cga gct ctc     288
Ile Ile Val Ser Gly Tyr His Asp Phe Gln Tyr Ala Gln Arg Ala Leu
                85                  90                  95 cgt tac gga gtc cat gac tat ata tta aag cct atc gat gaa gcg gaa     336
Arg Tyr Gly Val His Asp Tyr Ile Leu Lys Pro Ile Asp Glu Ala Glu
            100                 105                 110 ctg gag aca acg ttg aag gcg ctt tcc gga acg ttg gga tta aaa aag     384
Leu Glu Thr Thr Leu Lys Ala Leu Ser Gly Thr Leu Gly Leu Lys Lys
        115                 120                 125 ctg gcc acg atc gcg ggg gac agc ctg gtc acg gac tct att gtg gaa     432
Leu Ala Thr Ile Ala Gly Asp Ser Leu Val Thr Asp Ser Ile Val Glu
    130                 135                 140 acg ctt gtt caa ggc cag ttc tcg gag gcc gat aac gga gct tta tgc     480
Thr Leu Val Gln Gly Gln Phe Ser Glu Ala Asp Asn Gly Ala Leu Cys
145                 150                 155                 160 gcg gcg ctg caa atg cct gag ttc tcc agc ttc gat tac gtg ctg gtt     528
Ala Ala Leu Gln Met Pro Glu Phe Ser Ser Phe Asp Tyr Val Leu Val
                165                 170                 175
```

| | | |
|---|---|---|
| gag ctt cat gcc agc gcg caa tcc gca ggc acc gaa tgg cag gcc aag<br>Glu Leu His Ala Ser Ala Gln Ser Ala Gly Thr Glu Trp Gln Ala Lys<br>180 185 190 | | 576 |
| gag ctg gca gca gtc gtg cag tca gtg agc gct act cca agc agc aaa<br>Glu Leu Ala Ala Val Val Gln Ser Val Ser Ala Thr Pro Ser Ser Lys<br>195 200 205 | | 624 |
| att cct gtc tat gag cag acg agc ggt tta ttt ggc ctg ctt att gat<br>Ile Pro Val Tyr Glu Gln Thr Ser Gly Leu Phe Gly Leu Leu Ile Asp<br>210 215 220 | | 672 |
| cgg aag ccg ttt tta ccg ccg gaa ata cga ctt gaa tct gcc tat aac<br>Arg Lys Pro Phe Leu Pro Pro Glu Ile Arg Leu Glu Ser Ala Tyr Asn<br>225 230 235 240 | | 720 |
| agc ttg cat gcg gcc att gcg aaa tct tcg ggc aga ccg gtc acc tta<br>Ser Leu His Ala Ala Ile Ala Lys Ser Ser Gly Arg Pro Val Thr Leu<br>245 250 255 | | 768 |
| tat atc ggc aag acc gtg gaa cga ctg caa gaa atg tgc cta tcc tac<br>Tyr Ile Gly Lys Thr Val Glu Arg Leu Gln Glu Met Cys Leu Ser Tyr<br>260 265 270 | | 816 |
| cgg gcg gcg aat gaa gcc atg tcc tat aaa tac gcc gag caa ggc agc<br>Arg Ala Ala Asn Glu Ala Met Ser Tyr Lys Tyr Ala Glu Gln Gly Ser<br>275 280 285 | | 864 |
| tcc gtt atc tat gcg aat cag gta cag ggg acc cct ctg tat tat ttc<br>Ser Val Ile Tyr Ala Asn Gln Val Gln Gly Thr Pro Leu Tyr Tyr Phe<br>290 295 300 | | 912 |
| gat gtg gat tcg gag ctg tac agc cga cta ctc gag aga ctg gaa gag<br>Asp Val Asp Ser Glu Leu Tyr Ser Arg Leu Leu Glu Arg Leu Glu Glu<br>305 310 315 320 | | 960 |
| aat aac gcg gat ttg tat gag cag gat atc gag ctt tta ttc cgc caa<br>Asn Asn Ala Asp Leu Tyr Glu Gln Asp Ile Glu Leu Leu Phe Arg Gln<br>325 330 335 | | 1008 |
| ttt gtc gag aag cgg ttt gct ccc aat gcg gtt gcc aat acg att acc<br>Phe Val Glu Lys Arg Phe Ala Pro Asn Ala Val Ala Asn Thr Ile Thr<br>340 345 350 | | 1056 |
| cgg ttt gtg atc ggg att att aat ata att cgg aag atg gag gga gac<br>Arg Phe Val Ile Gly Ile Ile Asn Ile Ile Arg Lys Met Glu Gly Asp<br>355 360 365 | | 1104 |
| gag aag gga ctt agc aag ctc ccg ttc att atg gac tgg cag ggc agc<br>Glu Lys Gly Leu Ser Lys Leu Pro Phe Ile Met Asp Trp Gln Gly Ser<br>370 375 380 | | 1152 |
| aat agc cgt ctg cag gac ttg aag gga cta ttc acg gat ttc ctc cgc<br>Asn Ser Arg Leu Gln Asp Leu Lys Gly Leu Phe Thr Asp Phe Leu Arg<br>385 390 395 400 | | 1200 |
| gag gct gcc gtc tat ttg gca gag ctt cgg aac gag cag tcc aag ggc<br>Glu Ala Ala Val Tyr Leu Ala Glu Leu Arg Asn Glu Gln Ser Lys Gly<br>405 410 415 | | 1248 |
| ggg att gaa cgc atc aag aaa tac atc gaa gcg aac tat acg gag aat<br>Gly Ile Glu Arg Ile Lys Lys Tyr Ile Glu Ala Asn Tyr Thr Glu Asn<br>420 425 430 | | 1296 |
| att agc ctt aag agc att gca gga aaa ttt tat atg aac tcc gtt tat<br>Ile Ser Leu Lys Ser Ile Ala Gly Lys Phe Tyr Met Asn Ser Val Tyr<br>435 440 445 | | 1344 |
| ttg ggt cag ctg ttc cgt aaa acc tat ggg atc tat ttc aat gat ttt<br>Leu Gly Gln Leu Phe Arg Lys Thr Tyr Gly Ile Tyr Phe Asn Asp Phe<br>450 455 460 | | 1392 |
| cta ctg cag atc cgg atc gga gaa gcc aaa aag ctg ctt cgc cag acc<br>Leu Leu Gln Ile Arg Ile Gly Glu Ala Lys Lys Leu Leu Arg Gln Thr<br>465 470 475 480 | | 1440 |
| gat ctt agg atg tac gag att gcg gag aaa gtg ggc ttt cag aat gcc<br>Asp Leu Arg Met Tyr Glu Ile Ala Glu Lys Val Gly Phe Gln Asn Ala<br>485 490 495 | | 1488 |

```
gat tat ttc gtg acc caa ttt gag aag ctg gag aaa gtg aca ccg acc      1536
Asp Tyr Phe Val Thr Gln Phe Glu Lys Leu Glu Lys Val Thr Pro Thr
            500                 505                 510 gat tac cgc aac aag ctg ctg ggc aaa aaa taa                          1569
Asp Tyr Arg Asn Lys Leu Leu Gly Lys Lys
        515                 520

<210> SEQ ID NO 2
<211> LENGTH: 522
<212> TYPE: PRT
<213> ORGANISM: Paenibacillus sp.

<400> SEQUENCE: 2

Met Tyr Lys Val Leu Leu Val Asp Asp Glu Ile Phe Val Arg Lys Gly
1               5                   10                  15

Leu Arg Asn Leu Ile Asp Trp Glu Ser Leu Gly Tyr Glu Ile Cys Asp
            20                  25                  30

Glu Ala Gly Asn Gly Gln Glu Ala Leu Glu Lys Ile Gln Leu Ile Lys
        35                  40                  45

Pro Asp Leu Val Ile Ala Asp Ile Arg Met Pro Val Leu Asp Gly Leu
    50                  55                  60

Glu Leu Ile Arg Lys Val Thr Glu Glu Gly Val His Ser Pro Thr Phe
65                  70                  75                  80

Ile Ile Val Ser Gly Tyr His Asp Phe Gln Tyr Ala Gln Arg Ala Leu
                85                  90                  95

Arg Tyr Gly Val His Asp Tyr Ile Leu Lys Pro Ile Asp Glu Ala Glu
            100                 105                 110

Leu Glu Thr Thr Leu Lys Ala Leu Ser Gly Thr Leu Gly Leu Lys Lys
        115                 120                 125

Leu Ala Thr Ile Ala Gly Asp Ser Leu Val Thr Asp Ser Ile Val Glu
    130                 135                 140

Thr Leu Val Gln Gly Gln Phe Ser Glu Ala Asp Asn Gly Ala Leu Cys
145                 150                 155                 160

Ala Ala Leu Gln Met Pro Glu Phe Ser Ser Phe Asp Tyr Val Leu Val
                165                 170                 175

Glu Leu His Ala Ser Ala Gln Ser Ala Gly Thr Glu Trp Gln Ala Lys
            180                 185                 190

Glu Leu Ala Ala Val Val Gln Ser Val Ser Ala Thr Pro Ser Ser Lys
        195                 200                 205

Ile Pro Val Tyr Glu Gln Thr Ser Gly Leu Phe Gly Leu Leu Ile Asp
    210                 215                 220

Arg Lys Pro Phe Leu Pro Pro Glu Ile Arg Leu Glu Ser Ala Tyr Asn
225                 230                 235                 240

Ser Leu His Ala Ala Ile Ala Lys Ser Ser Gly Arg Pro Val Thr Leu
                245                 250                 255

Tyr Ile Gly Lys Thr Val Glu Arg Leu Gln Glu Met Cys Leu Ser Tyr
            260                 265                 270

Arg Ala Ala Asn Glu Ala Met Ser Tyr Lys Tyr Ala Glu Gln Gly Ser
        275                 280                 285

Ser Val Ile Tyr Ala Asn Gln Val Gln Gly Thr Pro Leu Tyr Tyr Phe
    290                 295                 300

Asp Val Asp Ser Glu Leu Tyr Ser Arg Leu Leu Glu Arg Leu Glu Glu
305                 310                 315                 320

Asn Asn Ala Asp Leu Tyr Glu Gln Asp Ile Glu Leu Leu Phe Arg Gln
                325                 330                 335
```

-continued

```
Phe Val Glu Lys Arg Phe Ala Pro Asn Ala Val Ala Asn Thr Ile Thr
             340                 345                 350
Arg Phe Val Ile Gly Ile Ile Asn Ile Ile Arg Lys Met Glu Gly Asp
         355                 360                 365
Glu Lys Gly Leu Ser Lys Leu Pro Phe Ile Met Asp Trp Gln Gly Ser
     370                 375                 380
Asn Ser Arg Leu Gln Asp Leu Lys Gly Leu Phe Thr Asp Phe Leu Arg
385                 390                 395                 400
Glu Ala Ala Val Tyr Leu Ala Glu Leu Arg Asn Glu Gln Ser Lys Gly
                 405                 410                 415
Gly Ile Glu Arg Ile Lys Lys Tyr Ile Glu Ala Asn Tyr Thr Glu Asn
             420                 425                 430
Ile Ser Leu Lys Ser Ile Ala Gly Lys Phe Tyr Met Asn Ser Val Tyr
         435                 440                 445
Leu Gly Gln Leu Phe Arg Lys Thr Tyr Gly Ile Tyr Phe Asn Asp Phe
     450                 455                 460
Leu Leu Gln Ile Arg Ile Gly Glu Ala Lys Lys Leu Leu Arg Gln Thr
465                 470                 475                 480
Asp Leu Arg Met Tyr Glu Ile Ala Glu Lys Val Gly Phe Gln Asn Ala
                 485                 490                 495
Asp Tyr Phe Val Thr Gln Phe Glu Lys Leu Glu Lys Val Thr Pro Thr
             500                 505                 510
Asp Tyr Arg Asn Lys Leu Leu Gly Lys Lys
         515                 520

<210> SEQ ID NO 3
<211> LENGTH: 1719
<212> TYPE: DNA
<213> ORGANISM: Paenibacillus sp.
<220> FEATURE:
<221> NAME/KEY: CDS
<222> LOCATION: (1)..(1719)

<400> SEQUENCE: 3 atg ggc aga ttt cat tgg aat cat ctt aaa ttg cgg gac aag ctt ttg      48
Met Gly Arg Phe His Trp Asn His Leu Lys Leu Arg Asp Lys Leu Leu
1               5                   10                  15 ctg atg tac gtc ttt tgc gta ttt atc ccg atc gta ttg acg aat atc      96
Leu Met Tyr Val Phe Cys Val Phe Ile Pro Ile Val Leu Thr Asn Ile
             20                  25                  30 gtc ttc tat aac gtt aca acc aac aat att aaa aac caa aaa tcg cat     144
Val Phe Tyr Asn Val Thr Thr Asn Asn Ile Lys Asn Gln Lys Ser His
         35                  40                  45 gac gcc gac atc gcc ctg gag aag ctt cag ggc gag ctt cgt gct gtc     192
Asp Ala Asp Ile Ala Leu Glu Lys Leu Gln Gly Glu Leu Arg Ala Val
     50                  55                  60 atc gat gaa gcc gcg ggt att tcc tac ctg tat tat atc gat ccg atg     240
Ile Asp Glu Ala Ala Gly Ile Ser Tyr Leu Tyr Tyr Ile Asp Pro Met
65                  70                  75                  80 ctg aat cag ctg ctg gat aaa aag tac gat tcc caa atc gaa tac gtt     288
Leu Asn Gln Leu Leu Asp Lys Lys Tyr Asp Ser Gln Ile Glu Tyr Val
                 85                  90                  95 gaa gct ttt aat aat atc cga agc gtc ttc aac aaa tcc gag cag gct     336
Glu Ala Phe Asn Asn Ile Arg Ser Val Phe Asn Lys Ser Glu Gln Ala
             100                 105                 110 tac aaa acg acc agc gct acg gtt att tat acc gat aat cca act gtg     384
Tyr Lys Thr Thr Ser Ala Thr Val Ile Tyr Thr Asp Asn Pro Thr Val
         115                 120                 125 tta tcc tcc gga cct att atg ccg ctt agc gaa acg gag aag gaa gcc     432
```

```
                    Leu Ser Ser Gly Pro Ile Met Pro Leu Ser Glu Thr Glu Lys Glu Ala
                                130             135                 140 gac tgg tac cgg gct ttt atg aag acg aat gtt tct tat ccg ttg ttt        480
Asp Trp Tyr Arg Ala Phe Met Lys Thr Asn Val Ser Tyr Pro Leu Phe
145                 150                 155                 160 ata cag gat gga gac acg ttt agc ctt gtt caa aga ctg aac tat gtc        528
Ile Gln Asp Gly Asp Thr Phe Ser Leu Val Gln Arg Leu Asn Tyr Val
                165                 170                 175 aaa ggc aac ggc tat aac aat ctg atc aag att gat ctg aat atg gca        576
Lys Gly Asn Gly Tyr Asn Asn Leu Ile Lys Ile Asp Leu Asn Met Ala
                180                 185                 190 acg gtc aag cag ttg ttt gcg tta tcc ggc ttt gag ggc agc att tac        624
Thr Val Lys Gln Leu Phe Ala Leu Ser Gly Phe Glu Gly Ser Ile Tyr
            195                 200                 205 ttc ttg aat ccg gaa ggt gcc gtc ctc tat tcc aac gac tcc agc gta        672
Phe Leu Asn Pro Glu Gly Ala Val Leu Tyr Ser Asn Asp Ser Ser Val
210                 215                 220 gac agg cat tca cag acg ctt ccg atg ccg aaa aac tct ctc tcc ttt        720
Asp Arg His Ser Gln Thr Leu Pro Met Pro Lys Asn Ser Leu Ser Phe
225                 230                 235                 240 gac aag gtt tac acg aac aac aat tat ttg aac gac tgg tcc ctg cat        768
Asp Lys Val Tyr Thr Asn Asn Asn Tyr Leu Asn Asp Trp Ser Leu His
                245                 250                 255 ggc gtc att aac gaa ggg agc ttt ctg cat gac gtg cgg aaa tcg ggt        816
Gly Val Ile Asn Glu Gly Ser Phe Leu His Asp Val Arg Lys Ser Gly
                260                 265                 270 tcc ttt gtc att ttt ttg gcg ctt att aac ttt gtg ctg cct tct ttg        864
Ser Phe Val Ile Phe Leu Ala Leu Ile Asn Phe Val Leu Pro Ser Leu
            275                 280                 285 att atc gcg gct ctc tcc aga tcc ata aac aaa cgt ctc gtc aag att        912
Ile Ile Ala Ala Leu Ser Arg Ser Ile Asn Lys Arg Leu Val Lys Ile
290                 295                 300 gta aag cat atg aaa aag gtg aaa aac cag cat ttc gag acg atc ccg        960
Val Lys His Met Lys Lys Val Lys Asn Gln His Phe Glu Thr Ile Pro
305                 310                 315                 320 ctt gat gat gcg cgc gat gag atc ggc caa tta acg ggt gaa ttc aac       1008
Leu Asp Asp Ala Arg Asp Glu Ile Gly Gln Leu Thr Gly Glu Phe Asn
                325                 330                 335 cgg atg acc gag cgg atc gac aac ctc att acc gat gtc tat cag gct       1056
Arg Met Thr Glu Arg Ile Asp Asn Leu Ile Thr Asp Val Tyr Gln Ala
                340                 345                 350 gat att cag aag aag gac ctg gag atc cgc cag cgc cag gca cag ctt       1104
Asp Ile Gln Lys Lys Asp Leu Glu Ile Arg Gln Arg Gln Ala Gln Leu
            355                 360                 365 cat gcc ctt cac agc cag atc aat ccc cac ttc ctg ttc aac tcg ctc       1152
His Ala Leu His Ser Gln Ile Asn Pro His Phe Leu Phe Asn Ser Leu
370                 375                 380 gag acg att cgg atg cgg agc ctg atg aag ggg gag acc gag acc gcg       1200
Glu Thr Ile Arg Met Arg Ser Leu Met Lys Gly Glu Thr Glu Thr Ala
385                 390                 395                 400 aag acc att cac tat atg gcg aag att ttc cgg aag tcg att tcc tgg       1248
Lys Thr Ile His Tyr Met Ala Lys Ile Phe Arg Lys Ser Ile Ser Trp
                405                 410                 415 aaa cgc agc tgg gtg tcg atc cgg gaa gag att gag ctg acg gaa tgc       1296
Lys Arg Ser Trp Val Ser Ile Arg Glu Glu Ile Glu Leu Thr Glu Cys
                420                 425                 430 ttc ctt gaa att cag aaa tac agg ttt ggc gac aag ctg caa tac cag       1344
Phe Leu Glu Ile Gln Lys Tyr Arg Phe Gly Asp Lys Leu Gln Tyr Gln
            435                 440                 445 atc acc gtc gaa gat acc gta tac gac cag atg att ccg aag atg acc       1392
```

```
Ile Thr Val Glu Asp Thr Val Tyr Asp Gln Met Ile Pro Lys Met Thr
            450                 455                 460 ttc ctg ccg ttt gtc gag aac gcc agc att cat ggc att gaa agc tcg       1440
Phe Leu Pro Phe Val Glu Asn Ala Ser Ile His Gly Ile Glu Ser Ser
465                 470                 475                 480 ccg gga atc ggt ctt att cag att cat atc gga atc gcc ggc aac aag       1488
Pro Gly Ile Gly Leu Ile Gln Ile His Ile Gly Ile Ala Gly Asn Lys
                485                 490                 495 ctg atg ttc agg ctg tcc gat aac ggg atc ggc atg tcc caa gcc aag       1536
Leu Met Phe Arg Leu Ser Asp Asn Gly Ile Gly Met Ser Gln Ala Lys
            500                 505                 510 ctg tcg gag ctg ctt aat tac ctg cgt ctg gat gat tcc atc ggt gac       1584
Leu Ser Glu Leu Leu Asn Tyr Leu Arg Leu Asp Asp Ser Ile Gly Asp
        515                 520                 525 aat gtc ggc atg aaa aac gtc tat acc cgg ctg aag cta tgc tat aaa       1632
Asn Val Gly Met Lys Asn Val Tyr Thr Arg Leu Lys Leu Cys Tyr Lys
    530                 535                 540 gac tcg ttt gaa ttc gac att gct agc gaa gaa ggt cat gga aca acc       1680
Asp Ser Phe Glu Phe Asp Ile Ala Ser Glu Glu Gly His Gly Thr Thr
545                 550                 555                 560 gtt gag ctg cgt ctt cct ctc gac atg aac ggg caa taa                   1719
Val Glu Leu Arg Leu Pro Leu Asp Met Asn Gly Gln
                565                 570

<210> SEQ ID NO 4
<211> LENGTH: 572
<212> TYPE: PRT
<213> ORGANISM: Paenibacillus sp.

<400> SEQUENCE: 4

Met Gly Arg Phe His Trp Asn His Leu Lys Leu Arg Asp Lys Leu Leu
1               5                   10                  15

Leu Met Tyr Val Phe Cys Val Phe Ile Pro Ile Val Leu Thr Asn Ile
            20                  25                  30

Val Phe Tyr Asn Val Thr Thr Asn Ile Lys Asn Gln Lys Ser His
        35                  40                  45

Asp Ala Asp Ile Ala Leu Glu Lys Leu Gln Gly Glu Leu Arg Ala Val
50                  55                  60

Ile Asp Glu Ala Ala Gly Ile Ser Tyr Leu Tyr Tyr Ile Asp Pro Met
65                  70                  75                  80

Leu Asn Gln Leu Leu Asp Lys Lys Tyr Asp Ser Gln Ile Glu Tyr Val
            85                  90                  95

Glu Ala Phe Asn Asn Ile Arg Ser Val Phe Asn Lys Ser Glu Gln Ala
        100                 105                 110

Tyr Lys Thr Thr Ser Ala Thr Val Ile Tyr Thr Asp Asn Pro Thr Val
    115                 120                 125

Leu Ser Ser Gly Pro Ile Met Pro Leu Ser Glu Thr Glu Lys Glu Ala
130                 135                 140

Asp Trp Tyr Arg Ala Phe Met Lys Thr Asn Val Ser Tyr Pro Leu Phe
145                 150                 155                 160

Ile Gln Asp Gly Asp Thr Phe Ser Leu Val Gln Arg Leu Asn Tyr Val
            165                 170                 175

Lys Gly Asn Gly Tyr Asn Asn Leu Ile Lys Ile Asp Leu Asn Met Ala
        180                 185                 190

Thr Val Lys Gln Leu Phe Ala Leu Ser Gly Phe Glu Gly Ser Ile Tyr
    195                 200                 205

Phe Leu Asn Pro Glu Gly Ala Val Leu Tyr Ser Asn Asp Ser Ser Val
210                 215                 220
```

Asp Arg His Ser Gln Thr Leu Pro Met Pro Lys Asn Ser Leu Ser Phe
225                 230                 235                 240

Asp Lys Val Tyr Thr Asn Asn Tyr Leu Asn Asp Trp Ser Leu His
            245                 250                 255

Gly Val Ile Asn Glu Gly Ser Phe Leu His Asp Val Arg Lys Ser Gly
                260                 265                 270

Ser Phe Val Ile Phe Leu Ala Leu Ile Asn Phe Val Leu Pro Ser Leu
        275                 280                 285

Ile Ile Ala Ala Leu Ser Arg Ser Ile Asn Lys Arg Leu Val Lys Ile
    290                 295                 300

Val Lys His Met Lys Lys Val Lys Asn Gln His Phe Glu Thr Ile Pro
305                 310                 315                 320

Leu Asp Asp Ala Arg Asp Glu Ile Gly Gln Leu Thr Gly Glu Phe Asn
                325                 330                 335

Arg Met Thr Glu Arg Ile Asp Asn Leu Ile Thr Asp Val Tyr Gln Ala
            340                 345                 350

Asp Ile Gln Lys Lys Asp Leu Glu Ile Arg Gln Arg Gln Ala Gln Leu
        355                 360                 365

His Ala Leu His Ser Gln Ile Asn Pro His Phe Leu Phe Asn Ser Leu
370                 375                 380

Glu Thr Ile Arg Met Arg Ser Leu Met Lys Gly Glu Thr Glu Thr Ala
385                 390                 395                 400

Lys Thr Ile His Tyr Met Ala Lys Ile Phe Arg Lys Ser Ile Ser Trp
                405                 410                 415

Lys Arg Ser Trp Val Ser Ile Arg Glu Glu Ile Glu Leu Thr Glu Cys
            420                 425                 430

Phe Leu Glu Ile Gln Lys Tyr Arg Phe Gly Asp Lys Leu Gln Tyr Gln
        435                 440                 445

Ile Thr Val Glu Asp Thr Val Tyr Asp Gln Met Ile Pro Lys Met Thr
    450                 455                 460

Phe Leu Pro Phe Val Glu Asn Ala Ser Ile His Gly Ile Glu Ser Ser
465                 470                 475                 480

Pro Gly Ile Gly Leu Ile Gln Ile His Ile Gly Ile Ala Gly Asn Lys
                485                 490                 495

Leu Met Phe Arg Leu Ser Asp Asn Gly Ile Gly Met Ser Gln Ala Lys
            500                 505                 510

Leu Ser Glu Leu Leu Asn Tyr Leu Arg Leu Asp Asp Ser Ile Gly Asp
        515                 520                 525

Asn Val Gly Met Lys Asn Val Tyr Thr Arg Leu Lys Leu Cys Tyr Lys
    530                 535                 540

Asp Ser Phe Glu Phe Asp Ile Ala Ser Glu Gly His Gly Thr Thr
545                 550                 555                 560

Val Glu Leu Arg Leu Pro Leu Asp Met Asn Gly Gln
                565                 570

<210> SEQ ID NO 5
<211> LENGTH: 1713
<212> TYPE: DNA
<213> ORGANISM: Paenibacillus sp.
<220> FEATURE:
<221> NAME/KEY: CDS
<222> LOCATION: (1)..(1713)

<400> SEQUENCE: 5 atg gtt aac aaa aag ctt tta act gtc agc ttg gct gct gct atg tta    48
Met Val Asn Lys Lys Leu Leu Thr Val Ser Leu Ala Ala Ala Met Leu

```
        1               5                  10                 15
gct gtt aca gca tcc gct tgc ggc ggc aat aac gat aac agc aat gca        96
Ala Val Thr Ala Ser Ala Cys Gly Gly Asn Asn Asp Asn Ser Asn Ala
              20                  25                  30 aat agc ggt aaa tcc ggc aat agc ggc aac gca gct tcc aac tcc gct       144
Asn Ser Gly Lys Ser Gly Asn Ser Gly Asn Ala Ala Ser Asn Ser Ala
         35                  40                  45 tct cct gaa gcg gat gac aaa aca ccc gtc act ttc tcg tac tac agc       192
Ser Pro Glu Ala Asp Asp Lys Thr Pro Val Thr Phe Ser Tyr Tyr Ser
 50                  55                  60 ttc acc agc caa aag gat gct ctt gcg agc gac acc gtt atc ggt aaa       240
Phe Thr Ser Gln Lys Asp Ala Leu Ala Ser Asp Thr Val Ile Gly Lys
 65                  70                  75                  80 gag ctg caa cag cag acc ggc gta gac tgg aaa atg gaa ttc ctc gtt       288
Glu Leu Gln Gln Gln Thr Gly Val Asp Trp Lys Met Glu Phe Leu Val
              85                  90                  95 ggc gat ccg caa acg aaa tcc ggc gtt atg atc gca agc ggc gac tat       336
Gly Asp Pro Gln Thr Lys Ser Gly Val Met Ile Ala Ser Gly Asp Tyr
             100                 105                 110 ccg gac gta atc gtt ccg gaa ggc gaa atc gac aag ctg ctt gac gct       384
Pro Asp Val Ile Val Pro Glu Gly Glu Ile Asp Lys Leu Leu Asp Ala
             115                 120                 125 ggc gca ttt att cct ctt gat gat ctg atc gag aaa tac ggt cca aac       432
Gly Ala Phe Ile Pro Leu Asp Asp Leu Ile Glu Lys Tyr Gly Pro Asn
130                 135                 140 atc aag cgc gta tac ggt cct tat ttt gat aaa ttc aga caa gca gac       480
Ile Lys Arg Val Tyr Gly Pro Tyr Phe Asp Lys Phe Arg Gln Ala Asp
145                 150                 155                 160 ggc aaa atg tac ttc ctg ccg ttt ggc gcg aac caa ggc tat atc ggc       528
Gly Lys Met Tyr Phe Leu Pro Phe Gly Ala Asn Gln Gly Tyr Ile Gly
                 165                 170                 175 gat ccc ggc atc agc caa ggc gca ttc tgg atc caa cgc tcc gtt ctg       576
Asp Pro Gly Ile Ser Gln Gly Ala Phe Trp Ile Gln Arg Ser Val Leu
             180                 185                 190 aag gaa gcg gga tat ccg aag atc aag acg ctt gac cag tac ttc gat       624
Lys Glu Ala Gly Tyr Pro Lys Ile Lys Thr Leu Asp Gln Tyr Phe Asp
             195                 200                 205 ctg atc aag caa tac caa gag aag cat ccg caa gta gac ggc aag gac       672
Leu Ile Lys Gln Tyr Gln Glu Lys His Pro Gln Val Asp Gly Lys Asp
210                 215                 220 acg att ggc ttt gca tcc ctt gca ggt cct gcc gac agc ttc ttc tcg       720
Thr Ile Gly Phe Ala Ser Leu Ala Gly Pro Ala Asp Ser Phe Phe Ser
225                 230                 235                 240 atc acc aac cct tcc atg cac ctt gcg ggc tac ccg aat gac ggc gac       768
Ile Thr Asn Pro Ser Met His Leu Ala Gly Tyr Pro Asn Asp Gly Asp
                 245                 250                 255 gtt atc gtc gac atg aac acg cat gag gct aaa act tac gca gct acg       816
Val Ile Val Asp Met Asn Thr His Glu Ala Lys Thr Tyr Ala Ala Thr
             260                 265                 270 gat atc gag aaa aaa tgg ctg caa aag ctg aac gaa gta aac gcg gaa       864
Asp Ile Glu Lys Lys Trp Leu Gln Lys Leu Asn Glu Val Asn Ala Glu
             275                 280                 285 ggc ttg ttc gat cct gag acc ttt aca gcg aac aaa gac caa ttc ctg       912
Gly Leu Phe Asp Pro Glu Thr Phe Thr Ala Asn Lys Asp Gln Phe Leu
290                 295                 300 gct aag ctg acc tcc ggc cgc gta ctt ggc tac ttc aac tac gca tgg       960
Ala Lys Leu Thr Ser Gly Arg Val Leu Gly Tyr Phe Asn Tyr Ala Trp
305                 310                 315                 320 cag gtt ggc gac gcg aca aac aac ctg aag aaa gcc ggc atc gac gag      1008
Gln Val Gly Asp Ala Thr Asn Asn Leu Lys Lys Ala Gly Ile Asp Glu
```

```
                    325                 330                 335
aag cgt tac gct ccg ctg cca atc gta ttc gac gag aat acg aaa gac    1056
Lys Arg Tyr Ala Pro Leu Pro Ile Val Phe Asp Glu Asn Thr Lys Asp
                340                 345                 350 caa tac gta gat ccg cct agc ttt gtt aac aac cgc ggt atc ggt atc    1104
Gln Tyr Val Asp Pro Pro Ser Phe Val Asn Asn Arg Gly Ile Gly Ile
            355                 360                 365 tcg gta aaa gcg aaa gac gct gta cgc att att aag tac ttc gac aac    1152
Ser Val Lys Ala Lys Asp Ala Val Arg Ile Ile Lys Tyr Phe Asp Asn
        370                 375                 380 ctt ctc aaa gaa gag aac caa gtt ctc gta cag tgg ggc gtt aaa gac    1200
Leu Leu Lys Glu Glu Asn Gln Val Leu Val Gln Trp Gly Val Lys Asp
385                 390                 395                 400 cag aac tac acc gtg gac gct aac ggc cgt tac gtg atg gat gcg cag    1248
Gln Asn Tyr Thr Val Asp Ala Asn Gly Arg Tyr Val Met Asp Ala Gln
                405                 410                 415 caa atc gct gac cgc aac gac cct gag aag aaa cgc aca gtc gga tgg    1296
Gln Ile Ala Asp Arg Asn Asp Pro Glu Lys Lys Arg Thr Val Gly Trp
            420                 425                 430 cag tac ttt gaa tac agc tgg ccg cgt tac ggc aac aac tcc gta ctg    1344
Gln Tyr Phe Glu Tyr Ser Trp Pro Arg Tyr Gly Asn Asn Ser Val Leu
        435                 440                 445 gct gac ggc aac tcg tat ggc gta ggc aac cag cct gaa gtg gct tac    1392
Ala Asp Gly Asn Ser Tyr Gly Val Gly Asn Gln Pro Glu Val Ala Tyr
450                 455                 460 gcg ggt tac acg gac ggc gac aaa gcg ctg ctg gac gcc tac ggc gtg    1440
Ala Gly Tyr Thr Asp Gly Asp Lys Ala Leu Leu Asp Ala Tyr Gly Val
465                 470                 475                 480 aag acc ttc tcc gaa tac ttc tcg aag cct gac gat cgc tcc tgg tac    1488
Lys Thr Phe Ser Glu Tyr Phe Ser Lys Pro Asp Asp Arg Ser Trp Tyr
                485                 490                 495 ccg gca tgg agt atc aac aaa ggt caa ggc acg cct gag cag atc ttc    1536
Pro Ala Trp Ser Ile Asn Lys Gly Gln Gly Thr Pro Glu Gln Ile Phe
            500                 505                 510 cag caa aaa gcc ggc gac ctg caa aag aaa ttc gtt ccg aag ctt gta    1584
Gln Gln Lys Ala Gly Asp Leu Gln Lys Lys Phe Val Pro Lys Leu Val
        515                 520                 525 ctt gcc aag cct agc gaa ttc gac tcg atc tgg agc gac tat aca ggc    1632
Leu Ala Lys Pro Ser Glu Phe Asp Ser Ile Trp Ser Asp Tyr Thr Gly
530                 535                 540 caa atg ggc aag ctt gac gtg aaa ggc tat gaa acc ttc gtt acg aaa    1680
Gln Met Gly Lys Leu Asp Val Lys Gly Tyr Glu Thr Phe Val Thr Lys
545                 550                 555                 560 gta gtt caa gac cgt atc gcg ggc aag tgg taa                        1713
Val Val Gln Asp Arg Ile Ala Gly Lys Trp
                565                 570

<210> SEQ ID NO 6
<211> LENGTH: 570
<212> TYPE: PRT
<213> ORGANISM: Paenibacillus sp.

<400> SEQUENCE: 6

Met Val Asn Lys Lys Leu Leu Thr Val Ser Leu Ala Ala Met Leu
1               5                   10                  15

Ala Val Thr Ala Ser Ala Cys Gly Gly Asn Asn Asp Asn Ser Asn Ala
                20                  25                  30

Asn Ser Gly Lys Ser Gly Asn Ser Gly Asn Ala Ala Ser Asn Ser Ala
            35                  40                  45

Ser Pro Glu Ala Asp Asp Lys Thr Pro Val Thr Phe Ser Tyr Tyr Ser
```

```
              50                  55                  60
Phe Thr Ser Gln Lys Asp Ala Leu Ala Ser Asp Thr Val Ile Gly Lys
 65                  70                  75                  80

Glu Leu Gln Gln Gln Thr Gly Val Asp Trp Lys Met Glu Phe Leu Val
                 85                  90                  95

Gly Asp Pro Gln Thr Lys Ser Gly Val Met Ile Ala Ser Gly Asp Tyr
            100                 105                 110

Pro Asp Val Ile Val Pro Glu Gly Glu Ile Asp Lys Leu Leu Asp Ala
        115                 120                 125

Gly Ala Phe Ile Pro Leu Asp Asp Leu Ile Glu Lys Tyr Gly Pro Asn
130                 135                 140

Ile Lys Arg Val Tyr Gly Pro Tyr Phe Asp Lys Phe Arg Gln Ala Asp
145                 150                 155                 160

Gly Lys Met Tyr Phe Leu Pro Phe Gly Ala Asn Gln Gly Tyr Ile Gly
                165                 170                 175

Asp Pro Gly Ile Ser Gln Gly Ala Phe Trp Ile Gln Arg Ser Val Leu
            180                 185                 190

Lys Glu Ala Gly Tyr Pro Lys Ile Lys Thr Leu Asp Gln Tyr Phe Asp
        195                 200                 205

Leu Ile Lys Gln Tyr Gln Glu Lys His Pro Gln Val Asp Gly Lys Asp
210                 215                 220

Thr Ile Gly Phe Ala Ser Leu Ala Gly Pro Ala Asp Ser Phe Phe Ser
225                 230                 235                 240

Ile Thr Asn Pro Ser Met His Leu Ala Gly Tyr Pro Asn Asp Gly Asp
                245                 250                 255

Val Ile Val Asp Met Asn Thr His Glu Ala Lys Thr Tyr Ala Ala Thr
            260                 265                 270

Asp Ile Glu Lys Lys Trp Leu Gln Lys Leu Asn Glu Val Asn Ala Glu
        275                 280                 285

Gly Leu Phe Asp Pro Glu Thr Phe Thr Ala Asn Lys Asp Gln Phe Leu
290                 295                 300

Ala Lys Leu Thr Ser Gly Arg Val Leu Gly Tyr Phe Asn Tyr Ala Trp
305                 310                 315                 320

Gln Val Gly Asp Ala Thr Asn Asn Leu Lys Lys Ala Gly Ile Asp Glu
                325                 330                 335

Lys Arg Tyr Ala Pro Leu Pro Ile Val Phe Asp Glu Asn Thr Lys Asp
            340                 345                 350

Gln Tyr Val Asp Pro Pro Ser Phe Val Asn Asn Arg Gly Ile Gly Ile
        355                 360                 365

Ser Val Lys Ala Lys Asp Ala Val Arg Ile Ile Lys Tyr Phe Asp Asn
370                 375                 380

Leu Leu Lys Glu Glu Asn Gln Val Leu Val Gln Trp Gly Val Lys Asp
385                 390                 395                 400

Gln Asn Tyr Thr Val Asp Ala Asn Gly Arg Tyr Val Met Asp Ala Gln
                405                 410                 415

Gln Ile Ala Asp Arg Asn Asp Pro Glu Lys Lys Arg Thr Val Gly Trp
            420                 425                 430

Gln Tyr Phe Glu Tyr Ser Trp Pro Arg Tyr Gly Asn Asn Ser Val Leu
        435                 440                 445

Ala Asp Gly Asn Ser Tyr Gly Val Gly Asn Gln Pro Glu Val Ala Tyr
450                 455                 460

Ala Gly Tyr Thr Asp Gly Asp Lys Ala Leu Leu Asp Ala Tyr Gly Val
465                 470                 475                 480
```

```
Lys Thr Phe Ser Glu Tyr Phe Ser Lys Pro Asp Asp Arg Ser Trp Tyr
            485                 490                 495

Pro Ala Trp Ser Ile Asn Lys Gly Gln Gly Thr Pro Glu Gln Ile Phe
            500                 505                 510

Gln Gln Lys Ala Gly Asp Leu Gln Lys Lys Phe Val Pro Lys Leu Val
            515                 520                 525

Leu Ala Lys Pro Ser Glu Phe Asp Ser Ile Trp Ser Asp Tyr Thr Gly
            530                 535                 540

Gln Met Gly Lys Leu Asp Val Lys Gly Tyr Glu Thr Phe Val Thr Lys
545                 550                 555                 560

Val Val Gln Asp Arg Ile Ala Gly Lys Trp
            565                 570

<210> SEQ ID NO 7
<211> LENGTH: 972
<212> TYPE: DNA
<213> ORGANISM: Paenibacillus sp.
<220> FEATURE:
<221> NAME/KEY: CDS
<222> LOCATION: (1)..(972)

<400> SEQUENCE: 7 gtg gag aac ata cat gaa gtt aca cca tct gtt gtc agg agt ccc aaa      48
Val Glu Asn Ile His Glu Val Thr Pro Ser Val Val Arg Ser Pro Lys
1               5                   10                  15 gca agc gaa tca cgg ctt caa ctg ttt ttc aaa aag tta ttg cag caa      96
Ala Ser Glu Ser Arg Leu Gln Leu Phe Phe Lys Lys Leu Leu Gln Gln
                20                  25                  30 aaa gtg ctc gtg ttt atg tcg atg ccg ttt gta tta tgg ctt ttc ctg     144
Lys Val Leu Val Phe Met Ser Met Pro Phe Val Leu Trp Leu Phe Leu
            35                  40                  45 ttt aag tac gta ccg ctc tgg ggc tgg acc atc tcc ttt caa aag ttc     192
Phe Lys Tyr Val Pro Leu Trp Gly Trp Thr Ile Ser Phe Gln Lys Phe
        50                  55                  60 aga ccg gca aag gat ttg ttc gat cag gag tgg gta ggc tgg aaa aac     240
Arg Pro Ala Lys Asp Leu Phe Asp Gln Glu Trp Val Gly Trp Lys Asn
65                  70                  75                  80 ttc aac ttc ctg ttt aac gac gac tcc ttc tat cgc gtg tta aga aat     288
Phe Asn Phe Leu Phe Asn Asp Asp Ser Phe Tyr Arg Val Leu Arg Asn
                85                  90                  95 acg atc gtt atg agc tcc atc aat ctt gta tta ggt ttt gtt acc gca     336
Thr Ile Val Met Ser Ser Ile Asn Leu Val Leu Gly Phe Val Thr Ala
                100                 105                 110 atc gta ttg gcg att tta tta aac gag ctt cgc caa att atg ttc aag     384
Ile Val Leu Ala Ile Leu Leu Asn Glu Leu Arg Gln Ile Met Phe Lys
            115                 120                 125 cgg gtc gta cag acg atc agc tac cta ccg cat ttt att tcc tgg gtc     432
Arg Val Val Gln Thr Ile Ser Tyr Leu Pro His Phe Ile Ser Trp Val
        130                 135                 140 gtt gcg gcc aat att att tct tcg gcg ctt gcg ccc gaa ggg atc gtt     480
Val Ala Ala Asn Ile Ile Ser Ser Ala Leu Ala Pro Glu Gly Ile Val
145                 150                 155                 160 aat att cta ttg acg aga atg cat ctg att gat cag cct atc tta tgg     528
Asn Ile Leu Leu Thr Arg Met His Leu Ile Asp Gln Pro Ile Leu Trp
                165                 170                 175 ctg ggc aaa ggg aat tac ttc tgg ggc atc ctt ggc gca tcg gaa gtt     576
Leu Gly Lys Gly Asn Tyr Phe Trp Gly Ile Leu Gly Ala Ser Glu Val
                180                 185                 190 tgg aaa aac gtc ggc tgg aac acc att atc tat ttg gcg gct att aca     624
Trp Lys Asn Val Gly Trp Asn Thr Ile Ile Tyr Leu Ala Ala Ile Thr
            195                 200                 205
```

```
acc att gac cct tcc caa tac gaa gct gcc gag att gac ggg gcg aac    672
Thr Ile Asp Pro Ser Gln Tyr Glu Ala Ala Glu Ile Asp Gly Ala Asn
    210                 215                 220 cgt tta caa cgg atc ctg cat att act tta ccg ggt ctg aag tcg gtt    720
Arg Leu Gln Arg Ile Leu His Ile Thr Leu Pro Gly Leu Lys Ser Val
225                 230                 235                 240 atc gta atc ctg ttg atc atg aac ctt gga aat att ctg gaa tcg gga    768
Ile Val Ile Leu Leu Ile Met Asn Leu Gly Asn Ile Leu Glu Ser Gly
                245                 250                 255 ttt gag ccg caa tac ttg ctc ggc aac ggg atg acc gtg gac tat tcc    816
Phe Glu Pro Gln Tyr Leu Leu Gly Asn Gly Met Thr Val Asp Tyr Ser
            260                 265                 270 gag aac ctt gat ata ttt gtg ttg aaa tac ggc atg aac atg ggc aac    864
Glu Asn Leu Asp Ile Phe Val Leu Lys Tyr Gly Met Asn Met Gly Asn
        275                 280                 285 tat tcc ttg gct aca gca gcc ggc atg ttc aaa acg gtc gtt agc ttt    912
Tyr Ser Leu Ala Thr Ala Ala Gly Met Phe Lys Thr Val Val Ser Phe
    290                 295                 300 atc ttc ctc tta tcg gcc aac tcg att gcg aag cgg ctt ggc gag agc    960
Ile Phe Leu Leu Ser Ala Asn Ser Ile Ala Lys Arg Leu Gly Glu Ser
305                 310                 315                 320 aga ctg ttc tag                                                    972
Arg Leu Phe
```

<210> SEQ ID NO 8
<211> LENGTH: 323
<212> TYPE: PRT
<213> ORGANISM: Paenibacillus sp.

<400> SEQUENCE: 8

```
Val Glu Asn Ile His Glu Val Thr Pro Ser Val Val Arg Ser Pro Lys
1               5                   10                  15

Ala Ser Glu Ser Arg Leu Gln Leu Phe Phe Lys Lys Leu Leu Gln Gln
            20                  25                  30

Lys Val Leu Val Phe Met Ser Met Pro Phe Val Leu Trp Leu Phe Leu
        35                  40                  45

Phe Lys Tyr Val Pro Leu Trp Gly Trp Thr Ile Ser Phe Gln Lys Phe
    50                  55                  60

Arg Pro Ala Lys Asp Leu Phe Asp Gln Glu Trp Val Gly Trp Lys Asn
65                  70                  75                  80

Phe Asn Phe Leu Phe Asn Asp Asp Ser Phe Tyr Arg Val Leu Arg Asn
                85                  90                  95

Thr Ile Val Met Ser Ser Ile Asn Leu Val Leu Gly Phe Val Thr Ala
            100                 105                 110

Ile Val Leu Ala Ile Leu Leu Asn Glu Leu Arg Gln Ile Met Phe Lys
        115                 120                 125

Arg Val Val Gln Thr Ile Ser Tyr Leu Pro His Phe Ile Ser Trp Val
    130                 135                 140

Val Ala Ala Asn Ile Ile Ser Ser Ala Leu Ala Pro Glu Gly Ile Val
145                 150                 155                 160

Asn Ile Leu Leu Thr Arg Met His Leu Ile Asp Gln Pro Ile Leu Trp
                165                 170                 175

Leu Gly Lys Gly Asn Tyr Phe Trp Gly Ile Leu Gly Ala Ser Glu Val
            180                 185                 190

Trp Lys Asn Val Gly Trp Asn Thr Ile Ile Tyr Leu Ala Ala Ile Thr
        195                 200                 205

Thr Ile Asp Pro Ser Gln Tyr Glu Ala Ala Glu Ile Asp Gly Ala Asn
```

```
            210                 215                 220
Arg Leu Gln Arg Ile Leu His Ile Thr Leu Pro Gly Leu Lys Ser Val
225                 230                 235                 240

Ile Val Ile Leu Leu Ile Met Asn Leu Gly Asn Ile Leu Glu Ser Gly
                245                 250                 255

Phe Glu Pro Gln Tyr Leu Leu Gly Asn Gly Met Thr Val Asp Tyr Ser
            260                 265                 270

Glu Asn Leu Asp Ile Phe Val Leu Lys Tyr Gly Met Asn Met Gly Asn
        275                 280                 285

Tyr Ser Leu Ala Thr Ala Ala Gly Met Phe Lys Thr Val Val Ser Phe
    290                 295                 300

Ile Phe Leu Leu Ser Ala Asn Ser Ile Ala Lys Arg Leu Gly Glu Ser
305                 310                 315                 320

Arg Leu Phe

<210> SEQ ID NO 9
<211> LENGTH: 921
<212> TYPE: DNA
<213> ORGANISM: Paenibacillus sp.
<220> FEATURE:
<221> NAME/KEY: CDS
<222> LOCATION: (1)..(921)

<400> SEQUENCE: 9 atg aaa gag agt tcg gcc aaa gcc agg tac agc tct tta ccg gat aag      48
Met Lys Glu Ser Ser Ala Lys Ala Arg Tyr Ser Ser Leu Pro Asp Lys
1               5                   10                  15 att ttt gat aca agt aat ata gtt ttt atg ttg ctc gtc gtg acg gtt      96
Ile Phe Asp Thr Ser Asn Ile Val Phe Met Leu Leu Val Val Thr Val
                20                  25                  30 acg cta tat cct ttc ctt aat atg ttc gcg ttg tcg ttc aac gat gcg     144
Thr Leu Tyr Pro Phe Leu Asn Met Phe Ala Leu Ser Phe Asn Asp Ala
            35                  40                  45 aat gac tcg atc cgc ggc ggc att tat gct tgg cca agg atg tgg aca     192
Asn Asp Ser Ile Arg Gly Gly Ile Tyr Ala Trp Pro Arg Met Trp Thr
        50                  55                  60 tgg gat aac tac agc tat att ttt aat gaa gca tcc atc tat cac gct     240
Trp Asp Asn Tyr Ser Tyr Ile Phe Asn Glu Ala Ser Ile Tyr His Ala
65                  70                  75                  80 acg ttg atc tcc gcc ttg cgt acg att gcc ggc acg att act tcc gtc     288
Thr Leu Ile Ser Ala Leu Arg Thr Ile Ala Gly Thr Ile Thr Ser Val
                85                  90                  95 ttc tgt acg gct atg ctg gct tat acg atc agc cgc cag gag ttt gtt     336
Phe Cys Thr Ala Met Leu Ala Tyr Thr Ile Ser Arg Gln Glu Phe Val
            100                 105                 110 ctg cgc aaa ttc gtt acg ctg gtc gca atc ttc acg atg tac ttc agc     384
Leu Arg Lys Phe Val Thr Leu Val Ala Ile Phe Thr Met Tyr Phe Ser
        115                 120                 125 gga ggt ctc att ccg gga tac ctg ctg atc aaa gag ctc cat atg att     432
Gly Gly Leu Ile Pro Gly Tyr Leu Leu Ile Lys Glu Leu His Met Ile
130                 135                 140 aac tcg ttc tgg gtt tat att atc ccc ggc att atc ggc gtc ttt aat     480
Asn Ser Phe Trp Val Tyr Ile Ile Pro Gly Ile Ile Gly Val Phe Asn
145                 150                 155                 160 atg atc gta atc cga tcc ttt atc gag gga ttg ccg gac ggc att atg     528
Met Ile Val Ile Arg Ser Phe Ile Glu Gly Leu Pro Asp Gly Ile Met
                165                 170                 175 gaa tcg gcg aaa att gac gga gcg ggc gaa ttc att acc ttc atg cga     576
Glu Ser Ala Lys Ile Asp Gly Ala Gly Glu Phe Ile Thr Phe Met Arg
            180                 185                 190
```

```
att gtt ttg ccg ctg acc gtg cct gct ctt gcg acc gtt tcg ctc ttc    624
Ile Val Leu Pro Leu Thr Val Pro Ala Leu Ala Thr Val Ser Leu Phe
    195                 200                 205 gta gcg gtg tct caa tgg aat tcc tgg ttt gac gta ttt ctg tac aac    672
Val Ala Val Ser Gln Trp Asn Ser Trp Phe Asp Val Phe Leu Tyr Asn
210                 215                 220 tct tcg cat ctt aac ctg agc acc ttg caa tac gaa tta atg aaa ata    720
Ser Ser His Leu Asn Leu Ser Thr Leu Gln Tyr Glu Leu Met Lys Ile
225                 230                 235                 240 ttg caa acc tcc aat acg gcg gca tcg tca acc aat gca ggc gat cag    768
Leu Gln Thr Ser Asn Thr Ala Ala Ser Ser Thr Asn Ala Gly Asp Gln
                245                 250                 255 ttt gca gcc gga caa agc ggc gta acg gcg gtt acg cca acc tcg atc    816
Phe Ala Ala Gly Gln Ser Gly Val Thr Ala Val Thr Pro Thr Ser Ile
                260                 265                 270 cgt gcg acg atg act att gtt gcg agt ctg ccg att att ctg gta tat    864
Arg Ala Thr Met Thr Ile Val Ala Ser Leu Pro Ile Ile Leu Val Tyr
            275                 280                 285 ccg ttc ctg cag aaa tac ttt gtt aaa ggg atg acc gta ggc ggc gtt    912
Pro Phe Leu Gln Lys Tyr Phe Val Lys Gly Met Thr Val Gly Gly Val
290                 295                 300 aaa ggt taa                                                        921
Lys Gly
305
```

<210> SEQ ID NO 10
<211> LENGTH: 306
<212> TYPE: PRT
<213> ORGANISM: Paenibacillus sp.

<400> SEQUENCE: 10

```
Met Lys Glu Ser Ser Ala Lys Ala Arg Tyr Ser Ser Leu Pro Asp Lys
1               5                   10                  15

Ile Phe Asp Thr Ser Asn Ile Val Phe Met Leu Leu Val Val Thr Val
                20                  25                  30

Thr Leu Tyr Pro Phe Leu Asn Met Phe Ala Leu Ser Phe Asn Asp Ala
            35                  40                  45

Asn Asp Ser Ile Arg Gly Gly Ile Tyr Ala Trp Pro Arg Met Trp Thr
        50                  55                  60

Trp Asp Asn Tyr Ser Tyr Ile Phe Asn Glu Ala Ser Ile Tyr His Ala
65                  70                  75                  80

Thr Leu Ile Ser Ala Leu Arg Thr Ile Ala Gly Thr Ile Thr Ser Val
                85                  90                  95

Phe Cys Thr Ala Met Leu Ala Tyr Thr Ile Ser Arg Gln Glu Phe Val
            100                 105                 110

Leu Arg Lys Phe Val Thr Leu Val Ala Ile Phe Thr Met Tyr Phe Ser
        115                 120                 125

Gly Gly Leu Ile Pro Gly Tyr Leu Leu Ile Lys Glu Leu His Met Ile
    130                 135                 140

Asn Ser Phe Trp Val Tyr Ile Ile Pro Gly Ile Ile Gly Val Phe Asn
145                 150                 155                 160

Met Ile Val Ile Arg Ser Phe Ile Glu Gly Leu Pro Asp Gly Ile Met
                165                 170                 175

Glu Ser Ala Lys Ile Asp Gly Ala Gly Glu Phe Ile Thr Phe Met Arg
            180                 185                 190

Ile Val Leu Pro Leu Thr Val Pro Ala Leu Ala Thr Val Ser Leu Phe
        195                 200                 205
```

```
Val Ala Val Ser Gln Trp Asn Ser Trp Phe Asp Val Phe Leu Tyr Asn
        210                 215                 220
Ser Ser His Leu Asn Leu Ser Thr Leu Gln Tyr Glu Leu Met Lys Ile
225                 230                 235                 240
Leu Gln Thr Ser Asn Thr Ala Ala Ser Ser Thr Asn Ala Gly Asp Gln
                245                 250                 255
Phe Ala Ala Gly Gln Ser Gly Val Thr Ala Val Thr Pro Thr Ser Ile
            260                 265                 270
Arg Ala Thr Met Thr Ile Val Ala Ser Leu Pro Ile Ile Leu Val Tyr
        275                 280                 285
Pro Phe Leu Gln Lys Tyr Phe Val Lys Gly Met Thr Val Gly Gly Val
    290                 295                 300
Lys Gly
305

<210> SEQ ID NO 11
<211> LENGTH: 2064
<212> TYPE: DNA
<213> ORGANISM: Paenibacillus sp.
<220> FEATURE:
<221> NAME/KEY: CDS
<222> LOCATION: (1)..(2064)

<400> SEQUENCE: 11 atg gga gac aac gga tac gcg gca tgg ctg aga tac gat caa gtg aag     48
Met Gly Asp Asn Gly Tyr Ala Ala Trp Leu Arg Tyr Asp Gln Val Lys
1               5                   10                  15 gat gaa acg cgc ttg gag caa tac gca ggc tgg acg ggt gag ctc gtg     96
Asp Glu Thr Arg Leu Glu Gln Tyr Ala Gly Trp Thr Gly Glu Leu Val
            20                  25                  30 ctg ccc gcg gga gta ccg atg gaa ggg atc atg aag aca gcc gcc gtg    144
Leu Pro Ala Gly Val Pro Met Glu Gly Ile Met Lys Thr Ala Ala Val
        35                  40                  45 gaa ttg tcg cgg gga atc cgc tcc atg ctg ggc aca acg cct tcg gtt    192
Glu Leu Ser Arg Gly Ile Arg Ser Met Leu Gly Thr Thr Pro Ser Val
    50                  55                  60 acg cat gaa gca tca ggg cag cgt ttt atc gtg ctg gag gtt ctt ggc    240
Thr His Glu Ala Ser Gly Gln Arg Phe Ile Val Leu Glu Val Leu Gly
65                  70                  75                  80 ggc ggc tct tgg ata gat caa gcg gcc ggc gat gcg gcg gct cta tct    288
Gly Gly Ser Trp Ile Asp Gln Ala Ala Gly Asp Ala Ala Ala Leu Ser
                85                  90                  95 gat gag ggc tac ttc tta aaa acc gtt cga gaa gcg gag aag gaa tat    336
Asp Glu Gly Tyr Phe Leu Lys Thr Val Arg Glu Ala Glu Lys Glu Tyr
            100                 105                 110 att atc gcg gcc ggc aag tcc gag aaa gca gta ctg tac gcg gta ttc    384
Ile Ile Ala Ala Gly Lys Ser Glu Lys Ala Val Leu Tyr Ala Val Phe
        115                 120                 125 cat ctg ctg cgc ctg atg cag tcc ggg act gcg att gat cag tta aat    432
His Leu Leu Arg Leu Met Gln Ser Gly Thr Ala Ile Asp Gln Leu Asn
    130                 135                 140 ctg gtc gag tcg ccg aaa tac agc ctt cgc atg att aac cat tgg gat    480
Leu Val Glu Ser Pro Lys Tyr Ser Leu Arg Met Ile Asn His Trp Asp
145                 150                 155                 160 aac atg gac ggc agc gtg gag cgc ggt tac tcc ggc cgt tcg att ttt    528
Asn Met Asp Gly Ser Val Glu Arg Gly Tyr Ser Gly Arg Ser Ile Phe
                165                 170                 175 tac gat aac aac aaa gtg ctg tcc gat tcg gaa cgg att cgc gat tac    576
Tyr Asp Asn Asn Lys Val Leu Ser Asp Ser Glu Arg Ile Arg Asp Tyr
            180                 185                 190
```

```
gcc cgt ctg atg gca tcg gtc gga att aat ggc atc gcg att aat aac         624
Ala Arg Leu Met Ala Ser Val Gly Ile Asn Gly Ile Ala Ile Asn Asn
        195                 200                 205 gta aac gtc cac cgc gaa gag aca ttc ctt att acg gag aag ctt ctg         672
Val Asn Val His Arg Glu Glu Thr Phe Leu Ile Thr Glu Lys Leu Leu
    210                 215                 220 ccg gat gtt gtc cgt atc gcc gag gta ttt ggc gaa tac ggc ata aag         720
Pro Asp Val Val Arg Ile Ala Glu Val Phe Gly Glu Tyr Gly Ile Lys
225                 230                 235                 240 ctg ttc ctg agc gtg aac tat gcc gga acc att gag att ggc ggc ctg         768
Leu Phe Leu Ser Val Asn Tyr Ala Gly Thr Ile Glu Ile Gly Gly Leu
                245                 250                 255 gag aca gcc gat cct ctt gat ccg gcc gtg cgc ggc tgg tgg aag gag         816
Glu Thr Ala Asp Pro Leu Asp Pro Ala Val Arg Gly Trp Trp Lys Glu
            260                 265                 270 aag gcg gct gaa gtg tac cgt tat att ccg gac ttt ggg ggc ttc ctt         864
Lys Ala Ala Glu Val Tyr Arg Tyr Ile Pro Asp Phe Gly Gly Phe Leu
        275                 280                 285 gtg aaa gcc gat tcc gag aat cgc ccc ggt ccg ttt acc tac gga cgc         912
Val Lys Ala Asp Ser Glu Asn Arg Pro Gly Pro Phe Thr Tyr Gly Arg
    290                 295                 300 gac cat gcg gac gga gct aac atg ctg gct gaa gca ttg gag ccg ttt         960
Asp His Ala Asp Gly Ala Asn Met Leu Ala Glu Ala Leu Glu Pro Phe
305                 310                 315                 320 ggc gga ctt gtg ctc tgg cgg tgc ttc gtt tac aac tgc cat cag gac        1008
Gly Gly Leu Val Leu Trp Arg Cys Phe Val Tyr Asn Cys His Gln Asp
                325                 330                 335 tgg cgg gat cgc tca acc gac cgt gcg cgt gcc gct tac gat cac ttt        1056
Trp Arg Asp Arg Ser Thr Asp Arg Ala Arg Ala Ala Tyr Asp His Phe
            340                 345                 350 aag ccg ctg gac gga cgc ttc aag gac aat gtg att ttg cag att aag        1104
Lys Pro Leu Asp Gly Arg Phe Lys Asp Asn Val Ile Leu Gln Ile Lys
        355                 360                 365 aac ggt ccg atg gac ttc cag gtc cgc gag ccg gtc tcg ccg ctc ttt        1152
Asn Gly Pro Met Asp Phe Gln Val Arg Glu Pro Val Ser Pro Leu Phe
    370                 375                 380 ggc gcg atg gag cat acc aac cag atg atg gaa ttc cag att gcc cag        1200
Gly Ala Met Glu His Thr Asn Gln Met Met Glu Phe Gln Ile Ala Gln
385                 390                 395                 400 gaa tat acg ggc cag cag aag gat gtc tgc ttc ctc att ccg cag tgg        1248
Glu Tyr Thr Gly Gln Gln Lys Asp Val Cys Phe Leu Ile Pro Gln Trp
                405                 410                 415 aag gaa gtc ttg aac ttt gac act tac gtc aaa ggt gcg ggc agc acg        1296
Lys Glu Val Leu Asn Phe Asp Thr Tyr Val Lys Gly Ala Gly Ser Thr
            420                 425                 430 gtg aag gag att gcg gca ggc agc gtc cat gcc tat act cat agc ggc        1344
Val Lys Glu Ile Ala Ala Gly Ser Val His Ala Tyr Thr His Ser Gly
        435                 440                 445 att acg gcc gtc agc aat atc ggc aac gac gag aac tgg acc ggg cat        1392
Ile Thr Ala Val Ser Asn Ile Gly Asn Asp Glu Asn Trp Thr Gly His
    450                 455                 460 cat ctc gcg cag gcg aat ttg tac ggc tac gga cgc tta atc tgg aat        1440
His Leu Ala Gln Ala Asn Leu Tyr Gly Tyr Gly Arg Leu Ile Trp Asn
465                 470                 475                 480 ccg gag ctt tct tcg gag gag att gcg gcg gaa tgg gct gcc caa acg        1488
Pro Glu Leu Ser Ser Glu Glu Ile Ala Ala Glu Trp Ala Ala Gln Thr
                485                 490                 495 ttt ggc ggc aat aag aac gta cag gat gtt ctt gta aac ttc ctg ctg        1536
Phe Gly Gly Asn Lys Asn Val Gln Asp Val Leu Val Asn Phe Leu Leu
            500                 505                 510
```

```
gag tcg ttg tcc att tac gag aat tat aca gcg ccg cta ggc gta ggc    1584
Glu Ser Leu Ser Ile Tyr Glu Asn Tyr Thr Ala Pro Leu Gly Val Gly
        515                 520                 525 tgg atg gtt acg cct cat tat cac tac ggt ccg gat att gac ggc tac    1632
Trp Met Val Thr Pro His Tyr His Tyr Gly Pro Asp Ile Asp Gly Tyr
530                 535                 540 gaa tat tcc aag tgg gga aca tac cat ttt gcc gat cat aag gga att    1680
Glu Tyr Ser Lys Trp Gly Thr Tyr His Phe Ala Asp His Lys Gly Ile
545                 550                 555                 560 ggg gtt gac cgt acg gct cag acg ggt acc ggc tac agc agc cag tat    1728
Gly Val Asp Arg Thr Ala Gln Thr Gly Thr Gly Tyr Ser Ser Gln Tyr
                565                 570                 575 gct ttg ccg aac gcc gag gtc tac gac agc ctg gag gct tgt ccg gat    1776
Ala Leu Pro Asn Ala Glu Val Tyr Asp Ser Leu Glu Ala Cys Pro Asp
            580                 585                 590 gag ctg ctg ctc ttc ttc cat cat gtg cct tac acg cat cag ttg aaa    1824
Glu Leu Leu Leu Phe Phe His His Val Pro Tyr Thr His Gln Leu Lys
        595                 600                 605 tcc ggc aag acg gtt att cag cat att tac gat acg cat ttc gcc ggc    1872
Ser Gly Lys Thr Val Ile Gln His Ile Tyr Asp Thr His Phe Ala Gly
610                 615                 620 gtg gag cgg gtt gaa tat tgg atg aac cgc tgg cag gag ctt gag ggt    1920
Val Glu Arg Val Glu Tyr Trp Met Asn Arg Trp Gln Glu Leu Glu Gly
625                 630                 635                 640 ctc gtg gac ggc gac cgg ttc cgc cat gta acg gga cgc atg aac tgg    1968
Leu Val Asp Gly Asp Arg Phe Arg His Val Thr Gly Arg Met Asn Trp
                645                 650                 655 cag cgt gaa aat gcc aag caa tgg cgc gac atc gtt aat acg tat ttc    2016
Gln Arg Glu Asn Ala Lys Gln Trp Arg Asp Ile Val Asn Thr Tyr Phe
            660                 665                 670 ttc cgc aaa tcc ggt att ccg gat acc cat aac cgg gtg att tac taa    2064
Phe Arg Lys Ser Gly Ile Pro Asp Thr His Asn Arg Val Ile Tyr
        675                 680                 685

<210> SEQ ID NO 12
<211> LENGTH: 687
<212> TYPE: PRT
<213> ORGANISM: Paenibacillus sp.

<400> SEQUENCE: 12

Met Gly Asp Asn Gly Tyr Ala Ala Trp Leu Arg Tyr Asp Gln Val Lys
1               5                   10                  15

Asp Glu Thr Arg Leu Glu Gln Tyr Ala Gly Trp Thr Gly Glu Leu Val
            20                  25                  30

Leu Pro Ala Gly Val Pro Met Glu Gly Ile Met Lys Thr Ala Ala Val
        35                  40                  45

Glu Leu Ser Arg Gly Ile Arg Ser Met Leu Gly Thr Thr Pro Ser Val
    50                  55                  60

Thr His Glu Ala Ser Gly Gln Arg Phe Ile Val Leu Glu Val Leu Gly
65                  70                  75                  80

Gly Gly Ser Trp Ile Asp Gln Ala Ala Gly Asp Ala Ala Leu Ser
                85                  90                  95

Asp Glu Gly Tyr Phe Leu Lys Thr Val Arg Glu Ala Glu Lys Glu Tyr
            100                 105                 110

Ile Ile Ala Ala Gly Lys Ser Glu Lys Ala Val Leu Tyr Ala Val Phe
        115                 120                 125

His Leu Leu Arg Leu Met Gln Ser Gly Thr Ala Ile Asp Gln Leu Asn
    130                 135                 140

Leu Val Glu Ser Pro Lys Tyr Ser Leu Arg Met Ile Asn His Trp Asp
```

```
            145                 150                 155                 160
Asn Met Asp Gly Ser Val Glu Arg Gly Tyr Ser Gly Arg Ser Ile Phe
                165                 170                 175

Tyr Asp Asn Asn Lys Val Leu Ser Asp Ser Glu Arg Ile Arg Asp Tyr
                180                 185                 190

Ala Arg Leu Met Ala Ser Val Gly Ile Asn Gly Ile Ala Ile Asn Asn
                195                 200                 205

Val Asn Val His Arg Glu Glu Thr Phe Leu Ile Thr Glu Lys Leu Leu
210                 215                 220

Pro Asp Val Val Arg Ile Ala Glu Val Phe Gly Glu Tyr Gly Ile Lys
225                 230                 235                 240

Leu Phe Leu Ser Val Asn Tyr Ala Gly Thr Ile Glu Ile Gly Gly Leu
                245                 250                 255

Glu Thr Ala Asp Pro Leu Asp Pro Ala Val Arg Gly Trp Trp Lys Glu
                260                 265                 270

Lys Ala Ala Glu Val Tyr Arg Tyr Ile Pro Asp Phe Gly Gly Phe Leu
                275                 280                 285

Val Lys Ala Asp Ser Glu Asn Arg Pro Gly Pro Phe Thr Tyr Gly Arg
                290                 295                 300

Asp His Ala Asp Gly Ala Asn Met Leu Ala Glu Ala Leu Glu Pro Phe
305                 310                 315                 320

Gly Gly Leu Val Leu Trp Arg Cys Phe Val Tyr Asn Cys His Gln Asp
                325                 330                 335

Trp Arg Asp Arg Ser Thr Asp Arg Ala Arg Ala Tyr Asp His Phe
                340                 345                 350

Lys Pro Leu Asp Gly Arg Phe Lys Asp Asn Val Ile Leu Gln Ile Lys
                355                 360                 365

Asn Gly Pro Met Asp Phe Gln Val Arg Glu Pro Val Ser Pro Leu Phe
                370                 375                 380

Gly Ala Met Glu His Thr Asn Gln Met Met Glu Phe Gln Ile Ala Gln
385                 390                 395                 400

Glu Tyr Thr Gly Gln Gln Lys Asp Val Cys Phe Leu Ile Pro Gln Trp
                405                 410                 415

Lys Glu Val Leu Asn Phe Asp Thr Tyr Val Lys Gly Ala Gly Ser Thr
                420                 425                 430

Val Lys Glu Ile Ala Ala Gly Ser Val His Ala Tyr Thr His Ser Gly
                435                 440                 445

Ile Thr Ala Val Ser Asn Ile Gly Asn Asp Glu Asn Trp Thr Gly His
                450                 455                 460

His Leu Ala Gln Ala Asn Leu Tyr Gly Tyr Gly Arg Leu Ile Trp Asn
465                 470                 475                 480

Pro Glu Leu Ser Ser Glu Glu Ile Ala Ala Glu Trp Ala Ala Gln Thr
                485                 490                 495

Phe Gly Gly Asn Lys Asn Val Gln Asp Val Leu Val Asn Phe Leu Leu
                500                 505                 510

Glu Ser Leu Ser Ile Tyr Glu Asn Tyr Thr Ala Pro Leu Gly Val Gly
                515                 520                 525

Trp Met Val Thr Pro His Tyr His Tyr Gly Pro Asp Ile Asp Gly Tyr
                530                 535                 540

Glu Tyr Ser Lys Trp Gly Thr Tyr His Phe Ala Asp His Lys Gly Ile
545                 550                 555                 560

Gly Val Asp Arg Thr Ala Gln Thr Gly Thr Gly Tyr Ser Gln Tyr
                565                 570                 575
```

```
Ala Leu Pro Asn Ala Glu Val Tyr Asp Ser Leu Glu Ala Cys Pro Asp
                580                 585                 590

Glu Leu Leu Leu Phe Phe His His Val Pro Tyr Thr His Gln Leu Lys
            595                 600                 605

Ser Gly Lys Thr Val Ile Gln His Ile Tyr Asp Thr His Phe Ala Gly
        610                 615                 620

Val Glu Arg Val Glu Tyr Trp Met Asn Arg Trp Gln Glu Leu Glu Gly
625                 630                 635                 640

Leu Val Asp Gly Asp Arg Phe Arg His Val Thr Gly Arg Met Asn Trp
                645                 650                 655

Gln Arg Glu Asn Ala Lys Gln Trp Arg Asp Ile Val Asn Thr Tyr Phe
            660                 665                 670

Phe Arg Lys Ser Gly Ile Pro Asp Thr His Asn Arg Val Ile Tyr
        675                 680                 685

<210> SEQ ID NO 13
<211> LENGTH: 1026
<212> TYPE: DNA
<213> ORGANISM: Paenibacillus sp.
<220> FEATURE:
<221> NAME/KEY: CDS
<222> LOCATION: (1)..(1026)

<400> SEQUENCE: 13 atg tca tat act tcg gag ttg ccg gca ctt cgt tcc gtt tat aag gat      48
Met Ser Tyr Thr Ser Glu Leu Pro Ala Leu Arg Ser Val Tyr Lys Asp
1               5                   10                  15 tac ttt gat att ggg gca gct gtg aat ctg acg aca att gca tcc cag      96
Tyr Phe Asp Ile Gly Ala Ala Val Asn Leu Thr Thr Ile Ala Ser Gln
            20                  25                  30 aag gat gtt ctt act gcc cat tac aac agt ctg act gcc gaa aat gac     144
Lys Asp Val Leu Thr Ala His Tyr Asn Ser Leu Thr Ala Glu Asn Asp
        35                  40                  45 atg aag ttc gaa cgc gtg cat ccg cag gaa ggg cag tat acg ttc gaa     192
Met Lys Phe Glu Arg Val His Pro Gln Glu Gly Gln Tyr Thr Phe Glu
    50                  55                  60 gcg gcg gac aag atc gct gac ttt gcg gct gca aac gcc atg aag ctg     240
Ala Ala Asp Lys Ile Ala Asp Phe Ala Ala Ala Asn Ala Met Lys Leu
65                  70                  75                  80 cgc ggg cat acg ctg gtg tgg cac aat cag acc cct gac tgg ata ttc     288
Arg Gly His Thr Leu Val Trp His Asn Gln Thr Pro Asp Trp Ile Phe
                85                  90                  95 caa aat gcg aat gga tcg cca gtc gat agg gaa acg ctg ctt gcc cgg     336
Gln Asn Ala Asn Gly Ser Pro Val Asp Arg Glu Thr Leu Leu Ala Arg
            100                 105                 110 atg aaa agc cat atc gaa aag gtt gtt ggc cgg tat aaa ggc att att     384
Met Lys Ser His Ile Glu Lys Val Val Gly Arg Tyr Lys Gly Ile Ile
        115                 120                 125 tac ggc tgg gat gtt gtg aac gag gtt atc gac gat aaa aac ggt gtc     432
Tyr Gly Trp Asp Val Val Asn Glu Val Ile Asp Asp Lys Asn Gly Val
    130                 135                 140 tgg ctt agg gag tcc aaa tgg cta aac tta gcc ggg gaa gat ttt atc     480
Trp Leu Arg Glu Ser Lys Trp Leu Asn Leu Ala Gly Glu Asp Phe Ile
145                 150                 155                 160 gca aaa gcc ttc gag tat gcg cat gcc gcc gac ccg aaa gcg ctt ctg     528
Ala Lys Ala Phe Glu Tyr Ala His Ala Ala Asp Pro Lys Ala Leu Leu
                165                 170                 175 ttc tac aat gat tac aac gag tgc att ccg gag aag cgg gat aaa att     576
Phe Tyr Asn Asp Tyr Asn Glu Cys Ile Pro Glu Lys Arg Asp Lys Ile
            180                 185                 190
```

```
atc cgt atc gtt caa tcg ctg cag gct aag caa gtg ccg att cac ggt       624
Ile Arg Ile Val Gln Ser Leu Gln Ala Lys Gln Val Pro Ile His Gly
        195                 200                 205 atc ggc ctg cag ggg cat tgg aat ttg aac ggt cca agt ctt gcc gag       672
Ile Gly Leu Gln Gly His Trp Asn Leu Asn Gly Pro Ser Leu Ala Glu
210                 215                 220 atc cgg gaa gcc atc gaa cgt tac gcg gca acg ggt ctt aag ctg cag       720
Ile Arg Glu Ala Ile Glu Arg Tyr Ala Ala Thr Gly Leu Lys Leu Gln
225                 230                 235                 240 gta acg gag ctg gat att tcg gta ttc gat cat gac gat aag cgg acg       768
Val Thr Glu Leu Asp Ile Ser Val Phe Asp His Asp Asp Lys Arg Thr
                245                 250                 255 gat ctg acg gag cct acg gca gac atg ctg gag cgg cag gcg gaa cgt       816
Asp Leu Thr Glu Pro Thr Ala Asp Met Leu Glu Arg Gln Ala Glu Arg
        260                 265                 270 tac ggg cag gta ttc gag ctg ttc cgc gaa tac aaa gag gcg att acc       864
Tyr Gly Gln Val Phe Glu Leu Phe Arg Glu Tyr Lys Glu Ala Ile Thr
    275                 280                 285 gcc gtt acg ttc tgg ggc gca gcc gac gat tac acc tgg ctg gat aac       912
Ala Val Thr Phe Trp Gly Ala Ala Asp Asp Tyr Thr Trp Leu Asp Asn
290                 295                 300 ttc ccg gta cgc ggg cgg aaa aat tgg ccg ttt gtg ttt gat gcc aac       960
Phe Pro Val Arg Gly Arg Lys Asn Trp Pro Phe Val Phe Asp Ala Asn
305                 310                 315                 320 cac gag cct aaa gct tcc ttc cgg aaa ata acc gat tgg cag gaa gcg      1008
His Glu Pro Lys Ala Ser Phe Arg Lys Ile Thr Asp Trp Gln Glu Ala
                325                 330                 335 ggg caa atc gat tca tga                                              1026
Gly Gln Ile Asp Ser
        340
```

<210> SEQ ID NO 14
<211> LENGTH: 341
<212> TYPE: PRT
<213> ORGANISM: Paenibacillus sp.

<400> SEQUENCE: 14

```
Met Ser Tyr Thr Ser Glu Leu Pro Ala Leu Arg Ser Val Tyr Lys Asp
1               5                   10                  15

Tyr Phe Asp Ile Gly Ala Ala Val Asn Leu Thr Thr Ile Ala Ser Gln
            20                  25                  30

Lys Asp Val Leu Thr Ala His Tyr Asn Ser Leu Thr Ala Glu Asn Asp
        35                  40                  45

Met Lys Phe Glu Arg Val His Pro Gln Glu Gly Gln Tyr Thr Phe Glu
    50                  55                  60

Ala Ala Asp Lys Ile Ala Asp Phe Ala Ala Ala Asn Ala Met Lys Leu
65                  70                  75                  80

Arg Gly His Thr Leu Val Trp His Asn Gln Thr Pro Asp Trp Ile Phe
                85                  90                  95

Gln Asn Ala Asn Gly Ser Pro Val Asp Arg Glu Thr Leu Leu Ala Arg
            100                 105                 110

Met Lys Ser His Ile Glu Lys Val Val Gly Arg Tyr Lys Gly Ile Ile
        115                 120                 125

Tyr Gly Trp Asp Val Val Asn Glu Val Ile Asp Lys Asn Gly Val
    130                 135                 140

Trp Leu Arg Glu Ser Lys Trp Leu Asn Leu Ala Gly Glu Asp Phe Ile
145                 150                 155                 160

Ala Lys Ala Phe Glu Tyr Ala His Ala Ala Asp Pro Lys Ala Leu Leu
                165                 170                 175
```

```
Phe Tyr Asn Asp Tyr Asn Glu Cys Ile Pro Glu Lys Arg Asp Lys Ile
            180                 185                 190

Ile Arg Ile Val Gln Ser Leu Gln Ala Lys Gln Val Pro Ile His Gly
195                 200                 205

Ile Gly Leu Gln Gly His Trp Asn Leu Asn Gly Pro Ser Leu Ala Glu
            210                 215                 220

Ile Arg Glu Ala Ile Glu Arg Tyr Ala Ala Thr Gly Leu Lys Leu Gln
225                 230                 235                 240

Val Thr Glu Leu Asp Ile Ser Val Phe Asp His Asp Asp Lys Arg Thr
                245                 250                 255

Asp Leu Thr Glu Pro Thr Ala Asp Met Leu Glu Arg Gln Ala Glu Arg
            260                 265                 270

Tyr Gly Gln Val Phe Glu Leu Phe Arg Glu Tyr Lys Glu Ala Ile Thr
        275                 280                 285

Ala Val Thr Phe Trp Gly Ala Ala Asp Asp Tyr Thr Trp Leu Asp Asn
    290                 295                 300

Phe Pro Val Arg Gly Arg Lys Asn Trp Pro Phe Val Phe Asp Ala Asn
305                 310                 315                 320

His Glu Pro Lys Ala Ser Phe Arg Lys Ile Thr Asp Trp Gln Glu Ala
                325                 330                 335

Gly Gln Ile Asp Ser
            340

<210> SEQ ID NO 15
<211> LENGTH: 1566
<212> TYPE: DNA
<213> ORGANISM: Paenibacillus sp.
<220> FEATURE:
<221> NAME/KEY: CDS
<222> LOCATION: (1)..(1566)

<400> SEQUENCE: 15 atg aca tac gca tca aca ggc aaa atc acg tac agg aac ccg gta ctg      48
Met Thr Tyr Ala Ser Thr Gly Lys Ile Thr Tyr Arg Asn Pro Val Leu
1               5                   10                  15 ccg ggc ttt tat ccg gat cca agc gct gtt cgg gta ggc gaa gat tat      96
Pro Gly Phe Tyr Pro Asp Pro Ser Ala Val Arg Val Gly Glu Asp Tyr
                20                  25                  30 tac atg gtg acc agc acc ttt gaa tat ttt ccg gga gtt ccg gtg ttt     144
Tyr Met Val Thr Ser Thr Phe Glu Tyr Phe Pro Gly Val Pro Val Phe
            35                  40                  45 cgc agc aag gat ctc gtt cat tgg gag cag att ggt cat gtg tta acc     192
Arg Ser Lys Asp Leu Val His Trp Glu Gln Ile Gly His Val Leu Thr
        50                  55                  60 agg gaa agc caa gtg aat ctg ctg agc cgc aac agc tcg gag ggc atc     240
Arg Glu Ser Gln Val Asn Leu Leu Ser Arg Asn Ser Ser Glu Gly Ile
65                  70                  75                  80 tat gcg cct gct ctt cgt tat cat gaa ggc gta ttt tat atg att aca     288
Tyr Ala Pro Ala Leu Arg Tyr His Glu Gly Val Phe Tyr Met Ile Thr
                85                  90                  95 acg gat gtg tac ggg ata ggc aac ttc tat gta acc gca acg gat ccg     336
Thr Asp Val Tyr Gly Ile Gly Asn Phe Tyr Val Thr Ala Thr Asp Pro
            100                 105                 110 gca gga cca tgg tcc gat ccg att cgg att cct tac ggc aat atc gat     384
Ala Gly Pro Trp Ser Asp Pro Ile Arg Ile Pro Tyr Gly Asn Ile Asp
        115                 120                 125 cct tct ctg ttt ttt gac gat gac ggc aaa gcg tac gtc tcg gcg cag     432
Pro Ser Leu Phe Phe Asp Asp Asp Gly Lys Ala Tyr Val Ser Ala Gln
130                 135                 140
```

```
gcc ggc ttt ggc gag acg tct cat att atc caa tac gag att gat atc      480
Ala Gly Phe Gly Glu Thr Ser His Ile Ile Gln Tyr Glu Ile Asp Ile
145                 150                 155                 160 ctg acg ggc gag gcc tta tcg gag cct gtt gtt gta ttt gag gga gac      528
Leu Thr Gly Glu Ala Leu Ser Glu Pro Val Val Val Phe Glu Gly Asp
                165                 170                 175 gaa ggg cct tgg gta gaa ggg ccg cat ctg tac aaa ata aac ggc ttt      576
Glu Gly Pro Trp Val Glu Gly Pro His Leu Tyr Lys Ile Asn Gly Phe
    180                 185                 190 tat tat atg atg acc gca tcc ggc gga acg ggg ccg atg cac agg gag      624
Tyr Tyr Met Met Thr Ala Ser Gly Gly Thr Gly Pro Met His Arg Glu
195                 200                 205 att atc ggc cgc ggc acc tct cct tac gga ccg ttt gaa atg ctg ccg      672
Ile Ile Gly Arg Gly Thr Ser Pro Tyr Gly Pro Phe Glu Met Leu Pro
210                 215                 220 cat ccg att ctg acg cat aac gag tta cag gat cat ccg att caa tac      720
His Pro Ile Leu Thr His Asn Glu Leu Gln Asp His Pro Ile Gln Tyr
225                 230                 235                 240 acc ggc cat gtt gag ctg ctc gat gac gtt cgt ggc cag tgg tgg gca      768
Thr Gly His Val Glu Leu Leu Asp Asp Val Arg Gly Gln Trp Trp Ala
                245                 250                 255 ttg ttt ctt ggc gtc cgg ccg caa ggc ggc aac ggc agc gtg ctt ggc      816
Leu Phe Leu Gly Val Arg Pro Gln Gly Gly Asn Gly Ser Val Leu Gly
                260                 265                 270 cgc gag acg ttc ctt gct ccc gta cgc tgg agt gaa gac ggc tgg ccg      864
Arg Glu Thr Phe Leu Ala Pro Val Arg Trp Ser Glu Asp Gly Trp Pro
            275                 280                 285 atg att gat aat aac gaa ggt cat gta tca atg gtt atg gag gga ccg      912
Met Ile Asp Asn Asn Glu Gly His Val Ser Met Val Met Glu Gly Pro
290                 295                 300 gct atc cgg gag agc aaa acc tcc atg gcc ggc atg gac aag tcg gtg      960
Ala Ile Arg Glu Ser Lys Thr Ser Met Ala Gly Met Asp Lys Ser Val
305                 310                 315                 320 acc acc aag ttc act tcc gaa ggg ctt agt ctc gaa tgg atg tat aac     1008
Thr Thr Lys Phe Thr Ser Glu Gly Leu Ser Leu Glu Trp Met Tyr Asn
                325                 330                 335 cgg gtg atc ccc gga ccg gag gag ctg tct tta acg gag aag gaa ggc     1056
Arg Val Ile Pro Gly Pro Glu Glu Leu Ser Leu Thr Glu Lys Glu Gly
                340                 345                 350 tgc ctt aga cta agc ggc aat gcc aaa ggt ctt cgc gac gga gga gct     1104
Cys Leu Arg Leu Ser Gly Asn Ala Lys Gly Leu Arg Asp Gly Gly Ala
            355                 360                 365 aat gta ttc gta tgc cgc cgc cag cag cat cat cgg atg agc atc gag     1152
Asn Val Phe Val Cys Arg Arg Gln Gln His His Arg Met Ser Ile Glu
370                 375                 380 act cgc ctg acc ttt gtt ccg gga aga gaa ggg gag cag gca gga att     1200
Thr Arg Leu Thr Phe Val Pro Gly Arg Glu Gly Glu Gln Ala Gly Ile
385                 390                 395                 400 gcc gcg cgg ctg agt gac aag tcc cat tac tcg atc gga atc acg aag     1248
Ala Ala Arg Leu Ser Asp Lys Ser His Tyr Ser Ile Gly Ile Thr Lys
                405                 410                 415 aag gac gga caa acc ggc att ctt gta acg gcg atg gcg caa gga agc     1296
Lys Asp Gly Gln Thr Gly Ile Leu Val Thr Ala Met Ala Gln Gly Ser
                420                 425                 430 gga acg gaa gtc ttt acc cca att gag gag cag gtt ccc gtc cgg ctc     1344
Gly Thr Glu Val Phe Thr Pro Ile Glu Glu Gln Val Pro Val Arg Leu
            435                 440                 445 tcg atc cgt tcg gac gag aag gaa tac gag ctt ttg tat acc ttg gga     1392
Ser Ile Arg Ser Asp Glu Lys Glu Tyr Glu Leu Leu Tyr Thr Leu Gly
450                 455                 460
```

```
ggt gcg tcc gcg gag tgg gtc agc cta agg acc ttg ccg gtg gaa gcc    1440
Gly Ala Ser Ala Glu Trp Val Ser Leu Arg Thr Leu Pro Val Glu Ala
465                 470                 475                 480 tta acg ccg gat gcg gac gga gct ttt acg ggc gta tgt ctt ggc atg    1488
Leu Thr Pro Asp Ala Asp Gly Ala Phe Thr Gly Val Cys Leu Gly Met
                485                 490                 495 ttt gca gca gga acg gag gaa ggc cat tcg gct ccc gct tat tac gat    1536
Phe Ala Ala Gly Thr Glu Glu Gly His Ser Ala Pro Ala Tyr Tyr Asp
            500                 505                 510 tac ttc gag tat cgt ccc gag agc ggt tga                            1566
Tyr Phe Glu Tyr Arg Pro Glu Ser Gly
        515                 520

<210> SEQ ID NO 16
<211> LENGTH: 521
<212> TYPE: PRT
<213> ORGANISM: Paenibacillus sp.

<400> SEQUENCE: 16

Met Thr Tyr Ala Ser Thr Gly Lys Ile Thr Tyr Arg Asn Pro Val Leu
1               5                   10                  15

Pro Gly Phe Tyr Pro Asp Pro Ser Ala Val Arg Val Gly Glu Asp Tyr
            20                  25                  30

Tyr Met Val Thr Ser Thr Phe Glu Tyr Phe Pro Gly Val Pro Val Phe
        35                  40                  45

Arg Ser Lys Asp Leu Val His Trp Glu Gln Ile Gly His Val Leu Thr
    50                  55                  60

Arg Glu Ser Gln Val Asn Leu Leu Ser Arg Asn Ser Ser Glu Gly Ile
65                  70                  75                  80

Tyr Ala Pro Ala Leu Arg Tyr His Glu Gly Val Phe Tyr Met Ile Thr
                85                  90                  95

Thr Asp Val Tyr Gly Ile Gly Asn Phe Tyr Val Thr Ala Thr Asp Pro
            100                 105                 110

Ala Gly Pro Trp Ser Asp Pro Ile Arg Ile Pro Tyr Gly Asn Ile Asp
        115                 120                 125

Pro Ser Leu Phe Phe Asp Asp Asp Gly Lys Ala Tyr Val Ser Ala Gln
    130                 135                 140

Ala Gly Phe Gly Glu Thr Ser His Ile Ile Gln Tyr Glu Ile Asp Ile
145                 150                 155                 160

Leu Thr Gly Glu Ala Leu Ser Glu Pro Val Val Phe Glu Gly Asp
                165                 170                 175

Glu Gly Pro Trp Val Glu Gly Pro His Leu Tyr Lys Ile Asn Gly Phe
            180                 185                 190

Tyr Tyr Met Met Thr Ala Ser Gly Gly Thr Gly Pro Met His Arg Glu
        195                 200                 205

Ile Ile Gly Arg Gly Thr Ser Pro Tyr Gly Pro Phe Glu Met Leu Pro
    210                 215                 220

His Pro Ile Leu Thr His Asn Glu Leu Gln Asp His Pro Ile Gln Tyr
225                 230                 235                 240

Thr Gly His Val Glu Leu Leu Asp Asp Val Arg Gly Gln Trp Trp Ala
                245                 250                 255

Leu Phe Leu Gly Val Arg Pro Gln Gly Gly Asn Gly Ser Val Leu Gly
            260                 265                 270

Arg Glu Thr Phe Leu Ala Pro Val Arg Trp Ser Glu Asp Gly Trp Pro
        275                 280                 285

Met Ile Asp Asn Asn Glu Gly His Val Ser Met Val Met Glu Gly Pro
```

```
            290                 295                 300
Ala Ile Arg Glu Ser Lys Thr Ser Met Ala Gly Met Asp Lys Ser Val
305                 310                 315                 320

Thr Thr Lys Phe Thr Ser Glu Gly Leu Ser Leu Glu Trp Met Tyr Asn
                325                 330                 335

Arg Val Ile Pro Gly Pro Glu Leu Ser Leu Thr Glu Lys Glu Gly
                340                 345                 350

Cys Leu Arg Leu Ser Gly Asn Ala Lys Gly Leu Arg Asp Gly Ala
                355                 360                 365

Asn Val Phe Val Cys Arg Arg Gln Gln His His Arg Met Ser Ile Glu
370                 375                 380

Thr Arg Leu Thr Phe Val Pro Gly Arg Glu Gly Gln Ala Gly Ile
385                 390                 395                 400

Ala Ala Arg Leu Ser Asp Lys Ser His Tyr Ser Ile Gly Ile Thr Lys
                405                 410                 415

Lys Asp Gly Gln Thr Gly Ile Leu Val Thr Ala Met Ala Gln Gly Ser
                420                 425                 430

Gly Thr Glu Val Phe Thr Pro Ile Glu Glu Gln Val Pro Val Arg Leu
                435                 440                 445

Ser Ile Arg Ser Asp Glu Lys Glu Tyr Glu Leu Leu Tyr Thr Leu Gly
                450                 455                 460

Gly Ala Ser Ala Glu Trp Val Ser Leu Arg Thr Leu Pro Val Glu Ala
465                 470                 475                 480

Leu Thr Pro Asp Ala Asp Gly Ala Phe Thr Gly Val Cys Leu Gly Met
                485                 490                 495

Phe Ala Ala Gly Thr Glu Glu Gly His Ser Ala Pro Ala Tyr Tyr Asp
                500                 505                 510

Tyr Phe Glu Tyr Arg Pro Glu Ser Gly
                515                 520

<210> SEQ ID NO 17
<211> LENGTH: 1125
<212> TYPE: DNA
<213> ORGANISM: Paenibacillus sp.
<220> FEATURE:
<221> NAME/KEY: CDS
<222> LOCATION: (1)..(1125)

<400> SEQUENCE: 17 ttg gag cag aat tat aaa ccg tta ttt gaa tcc ttt act ttc ccg agc      48
Leu Glu Gln Asn Tyr Lys Pro Leu Phe Glu Ser Phe Thr Phe Pro Ser
1               5                   10                  15 gga gtg gaa gta aag aac cgc att gtg atg gcg ccg atg acg cac tca      96
Gly Val Glu Val Lys Asn Arg Ile Val Met Ala Pro Met Thr His Ser
                20                  25                  30 tcc tct aat gat gat gga acg gta acg gat gcg gag ctg gaa tac tat     144
Ser Ser Asn Asp Asp Gly Thr Val Thr Asp Ala Glu Leu Glu Tyr Tyr
            35                  40                  45 gcc cgc cgg tcc gag gga gct ggc atg gtc ata acg gca tgt att tat     192
Ala Arg Arg Ser Glu Gly Ala Gly Met Val Ile Thr Ala Cys Ile Tyr
        50                  55                  60 gtc acg cca aac ggc aaa gga ttt ccc ggg gaa ttc gcg gga gac agc     240
Val Thr Pro Asn Gly Lys Gly Phe Pro Gly Glu Phe Ala Gly Asp Ser
65                  70                  75                  80 gat gct atg att ccg ggg ctt gct cgt ctt gca gag acg att aaa gcc     288
Asp Ala Met Ile Pro Gly Leu Ala Arg Leu Ala Glu Thr Ile Lys Ala
                85                  90                  95 aga ggc gcg aaa gct att ctc caa att ttc cat ggc ggc cgc cgt gta     336
```

```
                Arg Gly Ala Lys Ala Ile Leu Gln Ile Phe His Gly Arg Arg Val
                                100                 105                 110 ccg ccg gca ttg gtg cca aac ggc gat gtg gtt agc gca agc gcc gtt          384
Pro Pro Ala Leu Val Pro Asn Gly Asp Val Val Ser Ala Ser Ala Val
            115                 120                 125 gcg gcg acg gaa agc ccg gat gtt gtt ccg cgc gag ctg aag cac gaa          432
Ala Ala Thr Glu Ser Pro Asp Val Val Pro Arg Glu Leu Lys His Glu
130                 135                 140 gag att gaa gcg att atc cgc gat ttt ggc gag acg acc cgc cgc gcg          480
Glu Ile Glu Ala Ile Ile Arg Asp Phe Gly Glu Thr Thr Arg Arg Ala
145                 150                 155                 160 gcg ctt gcc ggc ttc gac gga gtc gaa att cac ggc gcg aac act tat          528
Ala Leu Ala Gly Phe Asp Gly Val Glu Ile His Gly Ala Asn Thr Tyr
                165                 170                 175 ctc ctg cag cag ttc tat tcc ccg cat tcc aac cgc aga aac gat caa          576
Leu Leu Gln Gln Phe Tyr Ser Pro His Ser Asn Arg Arg Asn Asp Gln
            180                 185                 190 tgg ggc gga gat atc gac cgg aga ctt aca ttc ccg ctc gcc gtt gtt          624
Trp Gly Gly Asp Ile Asp Arg Arg Leu Thr Phe Pro Leu Ala Val Val
        195                 200                 205 gat gaa gtg aaa cgc gcc gcg gct gag cat gcc aaa ggg cca ttc ttg          672
Asp Glu Val Lys Arg Ala Ala Ala Glu His Ala Lys Gly Pro Phe Leu
210                 215                 220 gtc gga tac cga ttc tct ccg gaa gaa ccg gag aca ccg gga ctt acg          720
Val Gly Tyr Arg Phe Ser Pro Glu Glu Pro Glu Thr Pro Gly Leu Thr
225                 230                 235                 240 atg gag gat acc ttc cgc ctg ttg gat gag ctt gcg cag aag gat ttg          768
Met Glu Asp Thr Phe Arg Leu Leu Asp Glu Leu Ala Gln Lys Asp Leu
                245                 250                 255 gat tac ctt cat gtc tcg ttg ttt gac ttc cgt tcc aag ccg tcg cgt          816
Asp Tyr Leu His Val Ser Leu Phe Asp Phe Arg Ser Lys Pro Ser Arg
            260                 265                 270 ggt gcg gat gat agc aaa aca aga ctg gaa tgg gtc gcg gag cgg gta          864
Gly Ala Asp Asp Ser Lys Thr Arg Leu Glu Trp Val Ala Glu Arg Val
        275                 280                 285 gcg ggc cgc gta ccg gtt atc ggc gta ggt tcg att aac tcg gcc gac          912
Ala Gly Arg Val Pro Val Ile Gly Val Gly Ser Ile Asn Ser Ala Asp
290                 295                 300 gat gcc att gaa gct cag caa acg ggc att ccg ctg gtt gcg att ggc          960
Asp Ala Ile Glu Ala Gln Gln Thr Gly Ile Pro Leu Val Ala Ile Gly
305                 310                 315                 320 cgc gta ctg ctg acg gat ccg gac tgg gta cag aag gtt gaa acc gga         1008
Arg Val Leu Leu Thr Asp Pro Asp Trp Val Gln Lys Val Glu Thr Gly
                325                 330                 335 cgc gag gat gag att cag tcc cgc tta agc tta agc tcg cag aag aag         1056
Arg Glu Asp Glu Ile Gln Ser Arg Leu Ser Leu Ser Ser Gln Lys Lys
            340                 345                 350 ctt gta att ccc gac ggt tta tgg cgc atg ttg acg gca aga gaa ggc         1104
Leu Val Ile Pro Asp Gly Leu Trp Arg Met Leu Thr Ala Arg Glu Gly
        355                 360                 365 tgg ctg cca ttt acc gat taa                                             1125
Trp Leu Pro Phe Thr Asp
    370

<210> SEQ ID NO 18
<211> LENGTH: 374
<212> TYPE: PRT
<213> ORGANISM: Paenibacillus sp.

<400> SEQUENCE: 18

Leu Glu Gln Asn Tyr Lys Pro Leu Phe Glu Ser Phe Thr Phe Pro Ser
```

```
                1               5                   10                  15
            Gly Val Glu Val Lys Asn Arg Ile Val Met Ala Pro Met Thr His Ser
                            20                  25                  30

Ser Ser Asn Asp Asp Gly Thr Val Thr Asp Ala Glu Leu Glu Tyr Tyr
                        35                  40                  45

Ala Arg Arg Ser Glu Gly Ala Gly Met Val Ile Thr Ala Cys Ile Tyr
                    50                  55                  60

Val Thr Pro Asn Gly Lys Gly Phe Pro Gly Phe Ala Gly Asp Ser
            65                      70                  75              80

Asp Ala Met Ile Pro Gly Leu Ala Arg Leu Ala Glu Thr Ile Lys Ala
                            85                  90                  95

Arg Gly Ala Lys Ala Ile Leu Gln Ile Phe His Gly Gly Arg Arg Val
                        100                 105                 110

Pro Pro Ala Leu Val Pro Asn Gly Asp Val Val Ser Ala Ser Ala Val
                        115                 120                 125

Ala Ala Thr Glu Ser Pro Asp Val Val Pro Arg Glu Leu Lys His Glu
                    130                 135                 140

Glu Ile Glu Ala Ile Ile Arg Asp Phe Gly Glu Thr Thr Arg Arg Ala
            145                     150                 155                 160

Ala Leu Ala Gly Phe Asp Gly Val Glu Ile His Gly Ala Asn Thr Tyr
                                165                 170                 175

Leu Leu Gln Gln Phe Tyr Ser Pro His Ser Asn Arg Arg Asn Asp Gln
                        180                 185                 190

Trp Gly Gly Asp Ile Asp Arg Arg Leu Thr Phe Pro Leu Ala Val Val
                        195                 200                 205

Asp Glu Val Lys Arg Ala Ala Ala Glu His Ala Lys Gly Pro Phe Leu
                    210                 215                 220

Val Gly Tyr Arg Phe Ser Pro Glu Glu Pro Glu Thr Pro Gly Leu Thr
            225                     230                 235                 240

Met Glu Asp Thr Phe Arg Leu Leu Asp Glu Leu Ala Gln Lys Asp Leu
                                245                 250                 255

Asp Tyr Leu His Val Ser Leu Phe Asp Phe Arg Ser Lys Pro Ser Arg
                        260                 265                 270

Gly Ala Asp Asp Ser Lys Thr Arg Leu Glu Trp Val Ala Glu Arg Val
                        275                 280                 285

Ala Gly Arg Val Pro Val Ile Gly Val Gly Ser Ile Asn Ser Ala Asp
                    290                 295                 300

Asp Ala Ile Glu Ala Gln Gln Thr Gly Ile Pro Leu Val Ala Ile Gly
            305                     310                 315                 320

Arg Val Leu Leu Thr Asp Pro Asp Trp Val Gln Lys Val Glu Thr Gly
                                325                 330                 335

Arg Glu Asp Glu Ile Gln Ser Arg Leu Ser Leu Ser Ser Gln Lys Lys
                        340                 345                 350

Leu Val Ile Pro Asp Gly Leu Trp Arg Met Leu Thr Ala Arg Glu Gly
                        355                 360                 365

Trp Leu Pro Phe Thr Asp
                370

<210> SEQ ID NO 19
<211> LENGTH: 4404
<212> TYPE: DNA
<213> ORGANISM: Paenibacillus sp.
<220> FEATURE:
<221> NAME/KEY: CDS
<222> LOCATION: (1)..(4404)
```

<400> SEQUENCE: 19

```
atg agt aga tcc ttg aaa aag ttc gtc tcg atc ctg ctc gca gca gcc        48
Met Ser Arg Ser Leu Lys Lys Phe Val Ser Ile Leu Leu Ala Ala Ala
1               5                   10                  15 ctg ctg atc ccg atc ggc aga ctt gca ccg gtt gcg gaa gct gca gag        96
Leu Leu Ile Pro Ile Gly Arg Leu Ala Pro Val Ala Glu Ala Ala Glu
            20                  25                  30 aat ccc acc att gtt tat cac gaa gac ttt gca atc gat aaa gga aaa       144
Asn Pro Thr Ile Val Tyr His Glu Asp Phe Ala Ile Asp Lys Gly Lys
35                  40                  45 gcc att caa tcc ggt ggc gcc agc ctc act cag gta aca gga aaa gta       192
Ala Ile Gln Ser Gly Gly Ala Ser Leu Thr Gln Val Thr Gly Lys Val
50                  55                  60 ttt gac ggc aac aat gat gga agc gct tta tat gta agc aac cgt gca       240
Phe Asp Gly Asn Asn Asp Gly Ser Ala Leu Tyr Val Ser Asn Arg Ala
65                  70                  75                  80 aac acc tgg gat gcg gct gat ttc aag ttc gct gac atc ggg ctt cag       288
Asn Thr Trp Asp Ala Ala Asp Phe Lys Phe Ala Asp Ile Gly Leu Gln
                85                  90                  95 aac ggg aaa acc tat acc gtt acg gta aaa gga tat gta gac caa gat       336
Asn Gly Lys Thr Tyr Thr Val Thr Val Lys Gly Tyr Val Asp Gln Asp
            100                 105                 110 gcg act gtc cct tcc ggt gcc cag gcc ttt ctt caa gcg gtg gac agc       384
Ala Thr Val Pro Ser Gly Ala Gln Ala Phe Leu Gln Ala Val Asp Ser
        115                 120                 125 aat aac tac ggc ttc ttg gca agc gct aac ttc gca gca gga acc gct       432
Asn Asn Tyr Gly Phe Leu Ala Ser Ala Asn Phe Ala Ala Gly Thr Ala
130                 135                 140 ttt acg ctg acc aaa gag ttt acg gtc gat aca agc gtc agc acc caa       480
Phe Thr Leu Thr Lys Glu Phe Thr Val Asp Thr Ser Val Ser Thr Gln
145                 150                 155                 160 ttg cgc gtt caa tcc agt gaa gaa ggc aaa gcc gtt ccg ttc tac att       528
Leu Arg Val Gln Ser Ser Glu Glu Gly Lys Ala Val Pro Phe Tyr Ile
                165                 170                 175 gga gac att cta ata aca gca aac ccg acg act acc aca aac acg gtt       576
Gly Asp Ile Leu Ile Thr Ala Asn Pro Thr Thr Thr Thr Asn Thr Val
            180                 185                 190 tac cat gaa gac ttt gca aca gac aaa gga aaa gcg gtg caa tcc ggc       624
Tyr His Glu Asp Phe Ala Thr Asp Lys Gly Lys Ala Val Gln Ser Gly
        195                 200                 205 ggc gct aat ctt gcc caa gtt gca gat aaa gta ttc gat ggc aac gat       672
Gly Ala Asn Leu Ala Gln Val Ala Asp Lys Val Phe Asp Gly Asn Asp
210                 215                 220 gac gga aaa gca ttg tat gta agt aac cgt gca aat acc tgg gat gcg       720
Asp Gly Lys Ala Leu Tyr Val Ser Asn Arg Ala Asn Thr Trp Asp Ala
225                 230                 235                 240 gct gat ttc aag ttc gct gac atc ggg ctt cag aac gga aaa acc tat       768
Ala Asp Phe Lys Phe Ala Asp Ile Gly Leu Gln Asn Gly Lys Thr Tyr
                245                 250                 255 acc gtt acg gta aaa gga tat gtc gac caa gac gcg act gtc cct tcc       816
Thr Val Thr Val Lys Gly Tyr Val Asp Gln Asp Ala Thr Val Pro Ser
            260                 265                 270 ggt gcc caa gct ttt tta caa gcg gtg gac agc aat aac tac ggc ttc       864
Gly Ala Gln Ala Phe Leu Gln Ala Val Asp Ser Asn Asn Tyr Gly Phe
        275                 280                 285 ttg gca agc gct aac ttc gcg gca aga agt gcc ttt acg ctg acc aaa       912
Leu Ala Ser Ala Asn Phe Ala Ala Arg Ser Ala Phe Thr Leu Thr Lys
290                 295                 300 gag ttt acg gtc gat aca agc gtc acc acc caa ttg cgc gtt caa tcc       960
Glu Phe Thr Val Asp Thr Ser Val Thr Thr Gln Leu Arg Val Gln Ser
```

```
                    305                 310                 315                 320
agt gaa gaa ggc aag gcc gtt ccg ttc tac atc gga gat att ctg att      1008
Ser Glu Glu Gly Lys Ala Val Pro Phe Tyr Ile Gly Asp Ile Leu Ile
                    325                 330                 335 acc gaa acc gtc aac tcg ggc ggt gga caa gaa gat cct cct agg ccg      1056
Thr Glu Thr Val Asn Ser Gly Gly Gly Gln Glu Asp Pro Pro Arg Pro
                340                 345                 350 cca gcg ttg ccg ttc aac acg att acg ttc gag gat caa aca gcc gga      1104
Pro Ala Leu Pro Phe Asn Thr Ile Thr Phe Glu Asp Gln Thr Ala Gly
            355                 360                 365 ggt ttt act ggc cgt gca ggc acc gaa aca ctg acg gtt acg aat gaa      1152
Gly Phe Thr Gly Arg Ala Gly Thr Glu Thr Leu Thr Val Thr Asn Glu
        370                 375                 380 tct aac cat acg gcg gac ggc tct tac tcc ctg aag gtg gaa ggc aga      1200
Ser Asn His Thr Ala Asp Gly Ser Tyr Ser Leu Lys Val Glu Gly Arg
385                 390                 395                 400 aca aca agc tgg cat ggc ccc tcc tta cgc gta gag aag tac gtg gat      1248
Thr Thr Ser Trp His Gly Pro Ser Leu Arg Val Glu Lys Tyr Val Asp
                    405                 410                 415 aaa ggc tac gag tat aag gtg act gct tgg gtg aag ctg ttg tct ccc      1296
Lys Gly Tyr Glu Tyr Lys Val Thr Ala Trp Val Lys Leu Leu Ser Pro
                420                 425                 430 gaa aca agc acc aag ctg gag ctt gcc tcc cag gtc ggg gac ggc ggc      1344
Glu Thr Ser Thr Lys Leu Glu Leu Ala Ser Gln Val Gly Asp Gly Gly
            435                 440                 445 agc gcc aac tac cca acg cca act acc caa gcc tgg caa gca aga cga      1392
Ser Ala Asn Tyr Pro Thr Pro Thr Thr Gln Ala Trp Gln Ala Arg Arg
        450                 455                 460 tta ccc gca gcc gac ggc tgg gtt cag ctg caa ggc aac tat cgc tat      1440
Leu Pro Ala Ala Asp Gly Trp Val Gln Leu Gln Gly Asn Tyr Arg Tyr
465                 470                 475                 480 aac agc gta ggc ggc gaa tat ctg acc att tac gta cag agc tcc aat      1488
Asn Ser Val Gly Gly Glu Tyr Leu Thr Ile Tyr Val Gln Ser Ser Asn
                    485                 490                 495 gca acg gcg tct tac tac atc gac gat atc agc ttt gaa agc acg gga      1536
Ala Thr Ala Ser Tyr Tyr Ile Asp Asp Ile Ser Phe Glu Ser Thr Gly
                500                 505                 510 tcc ggt cct gtc ggc att cag aag gat ctg gct cca ctc aaa gac gta      1584
Ser Gly Pro Val Gly Ile Gln Lys Asp Leu Ala Pro Leu Lys Asp Val
            515                 520                 525 tac aaa aac gac ttc ctg atc ggc aac gcc atc tcc gcg gaa gat ctg      1632
Tyr Lys Asn Asp Phe Leu Ile Gly Asn Ala Ile Ser Ala Glu Asp Leu
        530                 535                 540 gaa gga acg cgt ctt gag ctg ctg aag atg cat cat gat gtc gta acc      1680
Glu Gly Thr Arg Leu Glu Leu Leu Lys Met His His Asp Val Val Thr
545                 550                 555                 560 gcg ggc aat gcg atg aag ccg gat gcc ctg cag cca acg aag ggc aac      1728
Ala Gly Asn Ala Met Lys Pro Asp Ala Leu Gln Pro Thr Lys Gly Asn
                    565                 570                 575 ttt acc ttc acg gca gca gac gcc atg atc gac aaa gta ctg gcg gaa      1776
Phe Thr Phe Thr Ala Ala Asp Ala Met Ile Asp Lys Val Leu Ala Glu
                580                 585                 590 ggc atg aaa atg cac ggt cac gtg ctt gtg tgg cat caa caa tcg cct      1824
Gly Met Lys Met His Gly His Val Leu Val Trp His Gln Gln Ser Pro
            595                 600                 605 gct tgg ctg aat acc aag aaa gac gac aat aac aac acg gta ccg ctc      1872
Ala Trp Leu Asn Thr Lys Lys Asp Asp Asn Asn Asn Thr Val Pro Leu
        610                 615                 620 gga cgc gat gaa gcg ttg gat aac ttg aga acg cac atc cag acc gtt      1920
Gly Arg Asp Glu Ala Leu Asp Asn Leu Arg Thr His Ile Gln Thr Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 625 |     |     |     | 630 |     |     |     | 635 |     |     |     | 640 |     |      |
| atg | aag | cat | ttc | ggc | aac | aag | gtt | atc | tca | tgg | gat | gtt | gta | aac | gaa | 1968 |
| Met | Lys | His | Phe | Gly | Asn | Lys | Val | Ile | Ser | Trp | Asp | Val | Val | Asn | Glu |      |
|     |     |     |     | 645 |     |     |     |     | 650 |     |     |     |     | 655 |     |      |
| gcg | atg | aac | gac | aat | ccg | tcc | aat | ccg | gcg | gat | tat | aaa | gcc | tcg | ctg | 2016 |
| Ala | Met | Asn | Asp | Asn | Pro | Ser | Asn | Pro | Ala | Asp | Tyr | Lys | Ala | Ser | Leu |      |
|     |     |     |     | 660 |     |     |     |     | 665 |     |     |     |     | 670 |     |      |
| cgt | cag | act | cct | tgg | tat | caa | gcc | atc | gga | tcg | gac | tac | gtc | gag | cag | 2064 |
| Arg | Gln | Thr | Pro | Trp | Tyr | Gln | Ala | Ile | Gly | Ser | Asp | Tyr | Val | Glu | Gln |      |
|     |     |     |     |     | 675 |     |     |     |     | 680 |     |     |     |     | 685 |      |
| gcg | ttc | ctc | gcc | gca | aga | gaa | gtg | ctt | gac | gaa | aat | cct | agc | tgg | aat | 2112 |
| Ala | Phe | Leu | Ala | Ala | Arg | Glu | Val | Leu | Asp | Glu | Asn | Pro | Ser | Trp | Asn |      |
|     |     | 690 |     |     |     |     | 695 |     |     |     | 700 |     |     |     |     |      |
| atc | aag | ctg | tat | tac | aac | gat | tac | aac | gaa | gac | aac | cag | aat | aaa | gcg | 2160 |
| Ile | Lys | Leu | Tyr | Tyr | Asn | Asp | Tyr | Asn | Glu | Asp | Asn | Gln | Asn | Lys | Ala |      |
| 705 |     |     |     |     | 710 |     |     |     |     | 715 |     |     |     |     | 720 |      |
| acc | gcc | att | tat | aac | atg | gtc | aaa | gac | atc | aac | gac | cgc | tac | gcg | gca | 2208 |
| Thr | Ala | Ile | Tyr | Asn | Met | Val | Lys | Asp | Ile | Asn | Asp | Arg | Tyr | Ala | Ala |      |
|     |     |     |     | 725 |     |     |     |     | 730 |     |     |     |     | 735 |     |      |
| gct | cac | aac | ggc | aag | ctt | cta | att | gac | ggc | gtc | gga | atg | caa | ggc | cat | 2256 |
| Ala | His | Asn | Gly | Lys | Leu | Leu | Ile | Asp | Gly | Val | Gly | Met | Gln | Gly | His |      |
|     |     |     | 740 |     |     |     |     | 745 |     |     |     |     | 750 |     |     |      |
| tac | aat | atc | aat | aca | aat | ccg | gat | aac | gta | aag | ctt | tcc | ctg | gag | aaa | 2304 |
| Tyr | Asn | Ile | Asn | Thr | Asn | Pro | Asp | Asn | Val | Lys | Leu | Ser | Leu | Glu | Lys |      |
|     |     |     | 755 |     |     |     |     | 760 |     |     |     |     | 765 |     |     |      |
| ttt | att | tct | ctt | ggc | gtt | gaa | gtc | agc | gta | agc | gag | ctt | gac | gtt | acg | 2352 |
| Phe | Ile | Ser | Leu | Gly | Val | Glu | Val | Ser | Val | Ser | Glu | Leu | Asp | Val | Thr |      |
|     |     | 770 |     |     |     |     | 775 |     |     |     |     | 780 |     |     |     |      |
| gcc | gga | aac | aac | tat | acg | ctc | cct | gaa | aat | ctg | gct | gtc | ggg | caa | gcc | 2400 |
| Ala | Gly | Asn | Asn | Tyr | Thr | Leu | Pro | Glu | Asn | Leu | Ala | Val | Gly | Gln | Ala |      |
| 785 |     |     |     |     | 790 |     |     |     |     | 795 |     |     |     |     | 800 |      |
| tat | ctg | tac | gcc | cag | ttg | ttc | aag | ctt | tac | aaa | gag | cat | gcg | gat | cat | 2448 |
| Tyr | Leu | Tyr | Ala | Gln | Leu | Phe | Lys | Leu | Tyr | Lys | Glu | His | Ala | Asp | His |      |
|     |     |     |     | 805 |     |     |     |     | 810 |     |     |     |     | 815 |     |      |
| atc | gca | cgc | gta | acg | ttc | tgg | ggc | atg | gac | gac | aac | aca | agc | tgg | aga | 2496 |
| Ile | Ala | Arg | Val | Thr | Phe | Trp | Gly | Met | Asp | Asp | Asn | Thr | Ser | Trp | Arg |      |
|     |     |     | 820 |     |     |     |     | 825 |     |     |     |     | 830 |     |     |      |
| gcc | gag | aac | aac | ccg | ctc | ctg | ttc | gat | aag | aac | ctg | cag | gct | aaa | ccg | 2544 |
| Ala | Glu | Asn | Asn | Pro | Leu | Leu | Phe | Asp | Lys | Asn | Leu | Gln | Ala | Lys | Pro |      |
|     |     | 835 |     |     |     |     | 840 |     |     |     |     | 845 |     |     |     |      |
| gcc | tac | tat | ggc | gtt | att | gat | ccg | gac | aaa | tac | atg | gaa | gaa | cat | gcg | 2592 |
| Ala | Tyr | Tyr | Gly | Val | Ile | Asp | Pro | Asp | Lys | Tyr | Met | Glu | Glu | His | Ala |      |
| 850 |     |     |     |     | 855 |     |     |     |     | 860 |     |     |     |     |     |      |
| cca | gag | tcg | aaa | gat | gcc | aac | cag | gca | gag | gcc | caa | tac | ggt | act | ccg | 2640 |
| Pro | Glu | Ser | Lys | Asp | Ala | Asn | Gln | Ala | Glu | Ala | Gln | Tyr | Gly | Thr | Pro |      |
| 865 |     |     |     | 870 |     |     |     |     | 875 |     |     |     |     | 880 |     |      |
| gtt | att | gac | ggc | acc | gta | gat | tca | atc | tgg | agc | aat | gca | cag | gca | atg | 2688 |
| Val | Ile | Asp | Gly | Thr | Val | Asp | Ser | Ile | Trp | Ser | Asn | Ala | Gln | Ala | Met |      |
|     |     |     |     | 885 |     |     |     |     | 890 |     |     |     |     | 895 |     |      |
| ccg | gtc | aac | cgt | tat | cag | atg | gct | tgg | cag | ggt | gca | acg | ggt | acg | gct | 2736 |
| Pro | Val | Asn | Arg | Tyr | Gln | Met | Ala | Trp | Gln | Gly | Ala | Thr | Gly | Thr | Ala |      |
|     |     |     | 900 |     |     |     |     | 905 |     |     |     |     | 910 |     |     |      |
| aag | gca | ctc | tgg | gat | gat | cag | aac | ctg | tat | gtc | ctg | att | cag | gtc | agc | 2784 |
| Lys | Ala | Leu | Trp | Asp | Asp | Gln | Asn | Leu | Tyr | Val | Leu | Ile | Gln | Val | Ser |      |
|     |     | 915 |     |     |     |     | 920 |     |     |     |     | 925 |     |     |     |      |
| gac | tcc | cag | ctc | aac | aaa | gca | aac | gaa | aat | gca | tgg | gaa | cag | gac | tcc | 2832 |
| Asp | Ser | Gln | Leu | Asn | Lys | Ala | Asn | Glu | Asn | Ala | Trp | Glu | Gln | Asp | Ser |      |
|     | 930 |     |     |     |     | 935 |     |     |     |     | 940 |     |     |     |     |      |
| gtt | gaa | gtc | ttc | ctt | gac | caa | aac | aac | gga | aaa | acc | acc | ttc | tat | caa | 2880 |
| Val | Glu | Val | Phe | Leu | Asp | Gln | Asn | Asn | Gly | Lys | Thr | Thr | Phe | Tyr | Gln |      |

-continued

```
         945              950              955              960
aac gat gac ggt caa tat cgg gtt aac ttt gac aac gag acc tcc ttt    2928
Asn Asp Asp Gly Gln Tyr Arg Val Asn Phe Asp Asn Glu Thr Ser Phe
                965              970              975 agt ccc gca agc att gca gcc ggc ttc gag tct caa acc aag aaa acg    2976
Ser Pro Ala Ser Ile Ala Ala Gly Phe Glu Ser Gln Thr Lys Lys Thr
            980              985              990 gct aac agc tac acc gtt gag ctg aaa att ccg ctc acg gct gtg acg    3024
Ala Asn Ser Tyr Thr Val Glu Leu Lys Ile Pro Leu Thr Ala Val Thr
            995              1000             1005 cct gcc aat cag aag aag ctt ggc ttc gac gta caa atc aat gac        3069
Pro Ala Asn Gln Lys Lys Leu Gly Phe Asp Val Gln Ile Asn Asp
    1010             1015             1020 gca aca gac ggc gcg cgt acc agc gtt gcc gca tgg aac gat aca        3114
Ala Thr Asp Gly Ala Arg Thr Ser Val Ala Ala Trp Asn Asp Thr
    1025             1030             1035 acc ggc aac ggc tac cag gat act tcg gta tac ggc gag ctt acg        3159
Thr Gly Asn Gly Tyr Gln Asp Thr Ser Val Tyr Gly Glu Leu Thr
    1040             1045             1050 ctg gct ggc aaa ggc aca ggc gga acc ggc act gtc ggc acc acc        3204
Leu Ala Gly Lys Gly Thr Gly Gly Thr Gly Thr Val Gly Thr Thr
    1055             1060             1065 gta ccg caa acg ggc aac gtg gtg aag aat ccg gac ggc tcc aca        3249
Val Pro Gln Thr Gly Asn Val Val Lys Asn Pro Asp Gly Ser Thr
    1070             1075             1080 acg ctg aag cct gag gtc aaa acc act aac ggc aat gcc gtt ggc        3294
Thr Leu Lys Pro Glu Val Lys Thr Thr Asn Gly Asn Ala Val Gly
    1085             1090             1095 acg gtt acc ggc gac gat ctg aaa aaa gcg ctc gat caa gca gct        3339
Thr Val Thr Gly Asp Asp Leu Lys Lys Ala Leu Asp Gln Ala Ala
    1100             1105             1110 ccg gcg gca ggc ggc aag aag caa gtc atc att gac gtg ccg ctg        3384
Pro Ala Ala Gly Gly Lys Lys Gln Val Ile Ile Asp Val Pro Leu
    1115             1120             1125 cag gct aat gcc gct acg tat gcc gtc caa ctg cct acg caa agc        3429
Gln Ala Asn Ala Ala Thr Tyr Ala Val Gln Leu Pro Thr Gln Ser
    1130             1135             1140 tta aag agc caa gac ggc tac cag ctg acg gcg aaa atc gcc aac        3474
Leu Lys Ser Gln Asp Gly Tyr Gln Leu Thr Ala Lys Ile Ala Asn
    1145             1150             1155 gct ttt att caa att cca agc aat atg ctg gcc aat acg aac gtg        3519
Ala Phe Ile Gln Ile Pro Ser Asn Met Leu Ala Asn Thr Asn Val
    1160             1165             1170 act acg gat caa gta tcc atc cgg gta gcg aaa gct tcc ctc gat        3564
Thr Thr Asp Gln Val Ser Ile Arg Val Ala Lys Ala Ser Leu Asp
    1175             1180             1185 aac gtt gat gcc gcg act cgc gag ctg atc ggc aac cgt ccg gtt        3609
Asn Val Asp Ala Ala Thr Arg Glu Leu Ile Gly Asn Arg Pro Val
    1190             1195             1200 atc gac ctg agc ctt gtt gca ggc ggc aat gtg att gca tgg aac        3654
Ile Asp Leu Ser Leu Val Ala Gly Gly Asn Val Ile Ala Trp Asn
    1205             1210             1215 aac cca act gcg cct gta acg gtt gct gtt cct tac gcg cca acc        3699
Asn Pro Thr Ala Pro Val Thr Val Ala Val Pro Tyr Ala Pro Thr
    1220             1225             1230 gcg gaa gag ctc aag cat ccg gag cat atc ttg atc tgg tat atc        3744
Ala Glu Glu Leu Lys His Pro Glu His Ile Leu Ile Trp Tyr Ile
    1235             1240             1245 gat ggc agc gga aag gca act ccg gtt cct aac agc cgc tat gac        3789
Asp Gly Ser Gly Lys Ala Thr Pro Val Pro Asn Ser Arg Tyr Asp
```

```
gca gcg ctt gga gca gtc gtt ttc caa acg acg cat ttc agc act    3834
Ala Ala Leu Gly Ala Val Val Phe Gln Thr Thr His Phe Ser Thr
1265                1270                1275 tat gca gcc gta tcc gtc ttc aca acg ttt gga gac ctg gca aaa    3879
Tyr Ala Ala Val Ser Val Phe Thr Thr Phe Gly Asp Leu Ala Lys
    1280                1285                1290 gta cct tgg gcc aaa gaa gcg att gac gct atg gcc tcc cgc ggc    3924
Val Pro Trp Ala Lys Glu Ala Ile Asp Ala Met Ala Ser Arg Gly
1295                1300                1305 gtg atc aaa ggc acc ggc gag aac acc ttc tct cct gcg gcc tcc    3969
Val Ile Lys Gly Thr Gly Glu Asn Thr Phe Ser Pro Ala Ala Ser
1310                1315                1320 att aag cgg gca gac ttt atc gct ctt ctc gta aga gcg ctt gag    4014
Ile Lys Arg Ala Asp Phe Ile Ala Leu Leu Val Arg Ala Leu Glu
    1325                1330                1335 ctt cac ggt acc ggt act acg gat act gct atg ttt agc gat gta    4059
Leu His Gly Thr Gly Thr Thr Asp Thr Ala Met Phe Ser Asp Val
1340                1345                1350 ccg gca aac gct tat tac tat aat gaa cta gcc gtt gcg aaa cag    4104
Pro Ala Asn Ala Tyr Tyr Tyr Asn Glu Leu Ala Val Ala Lys Gln
1355                1360                1365 ctt ggc atc gca aca ggc ttt gaa gac aac acc ttc aaa ccg gac    4149
Leu Gly Ile Ala Thr Gly Phe Glu Asp Asn Thr Phe Lys Pro Asp
    1370                1375                1380 agc agc att tcc cgt caa gac atg atg gtg ctg acc acg cgc gct    4194
Ser Ser Ile Ser Arg Gln Asp Met Met Val Leu Thr Thr Arg Ala
1385                1390                1395 ctt gcc gta ctc ggc aag cag ctg ccg gca ggc ggc tcc ctg aac    4239
Leu Ala Val Leu Gly Lys Gln Leu Pro Ala Gly Gly Ser Leu Asn
1400                1405                1410 gca ttc tcc gat gcg gca agc gtt gcg ggt tac gcg caa gac agc    4284
Ala Phe Ser Asp Ala Ala Ser Val Ala Gly Tyr Ala Gln Asp Ser
    1415                1420                1425 gtg gca gcg ctt gta aaa gcc ggc gtc gtt caa ggc agc ggc agc    4329
Val Ala Ala Leu Val Lys Ala Gly Val Val Gln Gly Ser Gly Ser
1430                1435                1440 aag ctt gct ccg aat gac cag ctg acc cgc gcg gaa gca gcg gtt    4374
Lys Leu Ala Pro Asn Asp Gln Leu Thr Arg Ala Glu Ala Ala Val
1445                1450                1455 att ctg tac cgc atc tgg aag ctg caa taa                        4404
Ile Leu Tyr Arg Ile Trp Lys Leu Gln
    1460                1465
```

<210> SEQ ID NO 20
<211> LENGTH: 1467
<212> TYPE: PRT
<213> ORGANISM: Paenibacillus sp.

<400> SEQUENCE: 20

```
Met Ser Arg Ser Leu Lys Lys Phe Val Ser Ile Leu Leu Ala Ala Ala
1               5                   10                  15

Leu Leu Ile Pro Ile Gly Arg Leu Ala Pro Val Ala Glu Ala Ala Glu
            20                  25                  30

Asn Pro Thr Ile Val Tyr His Glu Asp Phe Ala Ile Asp Lys Gly Lys
        35                  40                  45

Ala Ile Gln Ser Gly Gly Ala Ser Leu Thr Gln Val Thr Gly Lys Val
    50                  55                  60

Phe Asp Gly Asn Asn Asp Gly Ser Ala Leu Tyr Val Ser Asn Arg Ala
65                  70                  75                  80
```

Asn Thr Trp Asp Ala Ala Asp Phe Lys Phe Ala Asp Ile Gly Leu Gln
                85                  90                  95

Asn Gly Lys Thr Tyr Thr Val Thr Val Lys Gly Tyr Val Asp Gln Asp
            100                 105                 110

Ala Thr Val Pro Ser Gly Ala Gln Ala Phe Leu Gln Ala Val Asp Ser
        115                 120                 125

Asn Asn Tyr Gly Phe Leu Ala Ser Ala Asn Phe Ala Ala Gly Thr Ala
    130                 135                 140

Phe Thr Leu Thr Lys Glu Phe Thr Val Asp Thr Ser Val Ser Thr Gln
145                 150                 155                 160

Leu Arg Val Gln Ser Ser Glu Glu Gly Lys Ala Val Pro Phe Tyr Ile
                165                 170                 175

Gly Asp Ile Leu Ile Thr Ala Asn Pro Thr Thr Thr Asn Thr Val
            180                 185                 190

Tyr His Glu Asp Phe Ala Thr Asp Lys Gly Lys Ala Val Gln Ser Gly
            195                 200                 205

Gly Ala Asn Leu Ala Gln Val Ala Asp Lys Val Phe Asp Gly Asn Asp
    210                 215                 220

Asp Gly Lys Ala Leu Tyr Val Ser Asn Arg Ala Asn Thr Trp Asp Ala
225                 230                 235                 240

Ala Asp Phe Lys Phe Ala Asp Ile Gly Leu Gln Asn Gly Lys Thr Tyr
                245                 250                 255

Thr Val Thr Val Lys Gly Tyr Val Asp Gln Asp Ala Thr Val Pro Ser
            260                 265                 270

Gly Ala Gln Ala Phe Leu Gln Ala Val Asp Ser Asn Asn Tyr Gly Phe
        275                 280                 285

Leu Ala Ser Ala Asn Phe Ala Ala Arg Ser Ala Phe Thr Leu Thr Lys
    290                 295                 300

Glu Phe Thr Val Asp Thr Ser Val Thr Gln Leu Arg Val Gln Ser
305                 310                 315                 320

Ser Glu Glu Gly Lys Ala Val Pro Phe Tyr Ile Gly Asp Ile Leu Ile
                325                 330                 335

Thr Glu Thr Val Asn Ser Gly Gly Gln Glu Asp Pro Pro Arg Pro
            340                 345                 350

Pro Ala Leu Pro Phe Asn Thr Ile Thr Phe Glu Asp Gln Thr Ala Gly
        355                 360                 365

Gly Phe Thr Gly Arg Ala Gly Thr Glu Thr Leu Thr Val Thr Asn Glu
    370                 375                 380

Ser Asn His Thr Ala Asp Gly Ser Tyr Ser Leu Lys Val Glu Gly Arg
385                 390                 395                 400

Thr Thr Ser Trp His Gly Pro Ser Leu Arg Val Glu Lys Tyr Val Asp
                405                 410                 415

Lys Gly Tyr Glu Tyr Lys Val Thr Ala Trp Val Lys Leu Leu Ser Pro
            420                 425                 430

Glu Thr Ser Thr Lys Leu Glu Leu Ala Ser Gln Val Gly Asp Gly Gly
        435                 440                 445

Ser Ala Asn Tyr Pro Thr Pro Thr Gln Ala Trp Gln Ala Arg Arg
    450                 455                 460

Leu Pro Ala Ala Asp Gly Trp Val Gln Leu Gln Gly Asn Tyr Arg Tyr
465                 470                 475                 480

Asn Ser Val Gly Gly Glu Tyr Leu Thr Ile Tyr Val Gln Ser Ser Asn
                485                 490                 495

Ala Thr Ala Ser Tyr Tyr Ile Asp Asp Ile Ser Phe Glu Ser Thr Gly

```
                500                 505                 510
Ser Gly Pro Val Gly Ile Gln Lys Asp Leu Ala Pro Leu Lys Asp Val
            515                 520                 525
Tyr Lys Asn Asp Phe Leu Ile Gly Asn Ala Ile Ser Ala Glu Asp Leu
        530                 535                 540
Glu Gly Thr Arg Leu Glu Leu Leu Lys Met His His Asp Val Val Thr
545                 550                 555                 560
Ala Gly Asn Ala Met Lys Pro Asp Ala Leu Gln Pro Thr Lys Gly Asn
                565                 570                 575
Phe Thr Phe Thr Ala Ala Asp Ala Met Ile Asp Lys Val Leu Ala Glu
            580                 585                 590
Gly Met Lys Met His Gly His Val Leu Val Trp His Gln Gln Ser Pro
        595                 600                 605
Ala Trp Leu Asn Thr Lys Lys Asp Asp Asn Asn Thr Val Pro Leu
610                 615                 620
Gly Arg Asp Glu Ala Leu Asp Asn Leu Arg Thr His Ile Gln Thr Val
625                 630                 635                 640
Met Lys His Phe Gly Asn Lys Val Ile Ser Trp Asp Val Val Asn Glu
                645                 650                 655
Ala Met Asn Asp Asn Pro Ser Asn Pro Ala Asp Tyr Lys Ala Ser Leu
            660                 665                 670
Arg Gln Thr Pro Trp Tyr Gln Ala Ile Gly Ser Asp Tyr Val Glu Gln
        675                 680                 685
Ala Phe Leu Ala Ala Arg Glu Val Leu Asp Glu Asn Pro Ser Trp Asn
        690                 695                 700
Ile Lys Leu Tyr Tyr Asn Asp Tyr Asn Glu Asp Asn Gln Asn Lys Ala
705                 710                 715                 720
Thr Ala Ile Tyr Asn Met Val Lys Asp Ile Asn Asp Arg Tyr Ala Ala
                725                 730                 735
Ala His Asn Gly Lys Leu Leu Ile Asp Gly Val Gly Met Gln Gly His
            740                 745                 750
Tyr Asn Ile Asn Thr Asn Pro Asp Asn Val Lys Leu Ser Leu Glu Lys
        755                 760                 765
Phe Ile Ser Leu Gly Val Glu Val Ser Val Ser Glu Leu Asp Val Thr
        770                 775                 780
Ala Gly Asn Asn Tyr Thr Leu Pro Glu Asn Leu Ala Val Gly Gln Ala
785                 790                 795                 800
Tyr Leu Tyr Ala Gln Leu Phe Lys Leu Tyr Lys Glu His Ala Asp His
                805                 810                 815
Ile Ala Arg Val Thr Phe Trp Gly Met Asp Asp Asn Thr Ser Trp Arg
            820                 825                 830
Ala Glu Asn Asn Pro Leu Leu Phe Asp Lys Asn Leu Gln Ala Lys Pro
        835                 840                 845
Ala Tyr Tyr Gly Val Ile Asp Pro Asp Lys Tyr Met Glu Glu His Ala
        850                 855                 860
Pro Glu Ser Lys Asp Ala Asn Gln Ala Glu Ala Gln Tyr Gly Thr Pro
865                 870                 875                 880
Val Ile Asp Gly Thr Val Asp Ser Ile Trp Ser Asn Ala Gln Ala Met
                885                 890                 895
Pro Val Asn Arg Tyr Gln Met Ala Trp Gln Gly Ala Thr Gly Thr Ala
            900                 905                 910
Lys Ala Leu Trp Asp Asp Gln Asn Leu Tyr Val Leu Ile Gln Val Ser
        915                 920                 925
```

-continued

Asp Ser Gln Leu Asn Lys Ala Asn Glu Asn Ala Trp Glu Gln Asp Ser
930                935                940

Val Glu Val Phe Leu Asp Gln Asn Asn Gly Lys Thr Thr Phe Tyr Gln
945                950                955                960

Asn Asp Asp Gly Gln Tyr Arg Val Asn Phe Asp Asn Glu Thr Ser Phe
            965                970                975

Ser Pro Ala Ser Ile Ala Ala Gly Phe Glu Ser Gln Thr Lys Lys Thr
            980                985                990

Ala Asn Ser Tyr Thr Val Glu Leu Lys Ile Pro Leu Thr Ala Val Thr
        995                1000                1005

Pro Ala Asn Gln Lys Lys Leu Gly Phe Asp Val Gln Ile Asn Asp
    1010                1015                1020

Ala Thr Asp Gly Ala Arg Thr Ser Val Ala Ala Trp Asn Asp Thr
    1025                1030                1035

Thr Gly Asn Gly Tyr Gln Asp Thr Ser Val Tyr Gly Glu Leu Thr
    1040                1045                1050

Leu Ala Gly Lys Gly Thr Gly Gly Thr Gly Thr Val Gly Thr Thr
    1055                1060                1065

Val Pro Gln Thr Gly Asn Val Val Lys Asn Pro Asp Gly Ser Thr
    1070                1075                1080

Thr Leu Lys Pro Glu Val Lys Thr Thr Asn Gly Asn Ala Val Gly
    1085                1090                1095

Thr Val Thr Gly Asp Asp Leu Lys Lys Ala Leu Asp Gln Ala Ala
    1100                1105                1110

Pro Ala Ala Gly Gly Lys Lys Gln Val Ile Ile Asp Val Pro Leu
    1115                1120                1125

Gln Ala Asn Ala Ala Thr Tyr Ala Val Gln Leu Pro Thr Gln Ser
    1130                1135                1140

Leu Lys Ser Gln Asp Gly Tyr Gln Leu Thr Ala Lys Ile Ala Asn
    1145                1150                1155

Ala Phe Ile Gln Ile Pro Ser Asn Met Leu Ala Asn Thr Asn Val
    1160                1165                1170

Thr Thr Asp Gln Val Ser Ile Arg Val Ala Lys Ala Ser Leu Asp
    1175                1180                1185

Asn Val Asp Ala Ala Thr Arg Glu Leu Ile Gly Asn Arg Pro Val
    1190                1195                1200

Ile Asp Leu Ser Leu Val Ala Gly Gly Asn Val Ile Ala Trp Asn
    1205                1210                1215

Asn Pro Thr Ala Pro Val Thr Val Ala Val Pro Tyr Ala Pro Thr
    1220                1225                1230

Ala Glu Glu Leu Lys His Pro Glu His Ile Leu Ile Trp Tyr Ile
    1235                1240                1245

Asp Gly Ser Gly Lys Ala Thr Pro Val Pro Asn Ser Arg Tyr Asp
    1250                1255                1260

Ala Ala Leu Gly Ala Val Val Phe Gln Thr Thr His Phe Ser Thr
    1265                1270                1275

Tyr Ala Ala Val Ser Val Phe Thr Thr Phe Gly Asp Leu Ala Lys
    1280                1285                1290

Val Pro Trp Ala Lys Glu Ala Ile Asp Ala Met Ala Ser Arg Gly
    1295                1300                1305

Val Ile Lys Gly Thr Gly Glu Asn Thr Phe Ser Pro Ala Ala Ser
    1310                1315                1320

Ile Lys Arg Ala Asp Phe Ile Ala Leu Leu Val Arg Ala Leu Glu
    1325                1330                1335

```
Leu His Gly Thr Gly Thr Thr Asp Thr Ala Met Phe Ser Asp Val
    1340            1345                1350
Pro Ala Asn Ala Tyr Tyr Tyr Asn Glu Leu Ala Val Ala Lys Gln
    1355            1360                1365
Leu Gly Ile Ala Thr Gly Phe Glu Asp Asn Thr Phe Lys Pro Asp
    1370            1375                1380
Ser Ser Ile Ser Arg Gln Asp Met Met Val Leu Thr Thr Arg Ala
    1385            1390                1395
Leu Ala Val Leu Gly Lys Gln Leu Pro Ala Gly Gly Ser Leu Asn
    1400            1405                1410
Ala Phe Ser Asp Ala Ala Ser Val Ala Gly Tyr Ala Gln Asp Ser
    1415            1420                1425
Val Ala Ala Leu Val Lys Ala Gly Val Val Gln Gly Ser Gly Ser
    1430            1435                1440
Lys Leu Ala Pro Asn Asp Gln Leu Thr Arg Ala Glu Ala Ala Val
    1445            1450                1455
Ile Leu Tyr Arg Ile Trp Lys Leu Gln
    1460            1465
```

<210> SEQ ID NO 21
<211> LENGTH: 15276
<212> TYPE: DNA
<213> ORGANISM: Paenibacillus sp.

<400> SEQUENCE: 21

```
cggcgaacgg atctggcagc ttcctgcatt cccggagtat aagagacagc tgagaagcga      60
tgcggccgat ctgaagaaca gcggcggacg atatgccggt gcaaccacag gcggtttgtt     120
tatcggcgct ttcgcggagg atcttccttg ggttcatctg acattgccg gtacggcatt      180
ccttgataag agccgcggac tggaaccaaa aggagcaacc ggcgtcatgg ttcgcacgct     240
ggtcgaactg gtaacgaaga acgagggcta aagtcaaact cattgaacgg ctagttatga     300
tcggctgaaa tcccgccgtc atagctggct gttttacttt acaagggttg tataatccct     360
ttaattcgca aagaaagttc tatagtttct cggtattgga cgtcgtataa ccgctttata     420
attttctgta taagcttgtc gggaagtaac aagccatatc ttgaaatcgc ttacagaaaa     480
aatgttaact gttcaaaaga cctaacaata ggagaaaaac aggtaatcag agcaggatgt     540
tttataatac gattgctttt ataattatta atgtcattaa ggattagcta gaagattcag     600
ctgtcagggg gccttgcata tgtacaaagt gttattggtg gatgatgaga ttttgtgcg      660
caaagggtta aggaatttaa tagactggga atcgcttggc tatgaaattt gcgatgaagc     720
gggtaacgga caggaagcat tagagaaaat acagctgatt aagcctgatc tcgttatcgc     780
ggatatccgg atgccagtgc tggacggatt ggagcttatc cgcaaggtta ccgaggaggg     840
cgtacatagc ccgaccttta ttatcgtcag cgggtatcat gatttccagt acgcgcagcg     900
agctctccgt tacggagtcc atgactatat attaaagcct atcgatgaag cggaactgga     960
gacaacgttg aaggcgcttt ccggaacgtt gggattaaaa aagctggcca cgatcgcggg    1020
ggacagcctg gtcacggact ctattgtgga aacgcttgtt caaggccagt ctcggaggc     1080
cgataacgga gctttatgcg cggcgctgca aatgcctgag ttctccagct tcgattacgt    1140
gctggttgag cttcatgcca gcgcgcaatc cgcaggcacc gaatggcagg ccaaggagct    1200
ggcagcagtc gtgcagtcag tgagcgctac tccaagcagc aaaattcctg tctatgagca    1260
gacgagcggt ttatttggcc tgcttattga tcggaagccg tttttaccgc cggaaatacg    1320
```

-continued

```
acttgaatct gcctataaca gcttgcatgc ggccattgcg aaatcttcgg gcagaccggt      1380
caccttatat atcggcaaga ccgtggaacg actgcaagaa atgtgcctat cctaccgggc      1440
ggcgaatgaa gccatgtcct ataaatacgc cgagcaaggc agctccgtta tctatgcgaa      1500
tcaggtacag gggacccctc tgtattattt cgatgtggat tcggagctgt acagccgact      1560
actcgagaga ctggaagaga ataacgcgga tttgtatgag caggatatcg agctttatt      1620
ccgccaattt gtcgagaagc ggtttgctcc caatgcggtt gccaatacga ttacccggtt      1680
tgtgatcggg attattaata taattcggaa gatggaggga gacgagaagg gacttagcaa      1740
gctcccgttc attatggact ggcagggcag caatagccgt ctgcaggact tgaagggact      1800
attcacggat ttcctccgcg aggctgccgt ctatttggca gagcttcgga acgagcagtc      1860
caagggcggg attgaacgca tcaagaaata catcgaagcg aactatacgg agaatattag      1920
ccttaagagc attgcaggaa aattttatat gaactccgtt tatttgggtc agctgttccg      1980
taaaacctat gggatctatt tcaatgattt tctactgcag atccggatcg agaagccaa      2040
aaagctgctt cgccagaccg atcttaggat gtacgagatt gcggagaaag tgggctttca      2100
gaatgccgat tatttcgtga cccaatttga gaagctggag aaagtgacac cgaccgatta      2160
ccgcaacaag ctgctgggca aaaataaac gggtggagat ttgatgggca gatttcattg      2220
gaatcatctt aaattgcggg acaagctttt gctgatgtac gtcttttgcg tatttatccc      2280
gatcgtattg acgaatatcg tcttctataa cgttacaacc aacaatatta aaaccaaaa      2340
atcgcatgac gccgacatcg ccctggagaa gcttcagggc gagcttcgtg ctgtcatcga      2400
tgaagccgcg ggtatttcct acctgtatta tatcgatccg atgctgaatc agctgctgga      2460
taaaaagtac gattcccaaa tcgaatacgt tgaagctttt aataatatcc gaagcgtctt      2520
caacaaatcc gagcaggctt acaaaacgac cagcgctacg gttatttata ccgataatcc      2580
aactgtgtta tcctccggac ctattatgcc gcttagcgaa acggagaagg aagccgactg      2640
gtaccgggct tttatgaaga cgaatgtttc ttatccgttg tttatacagg atggagacac      2700
gtttagcctt gttcaaagac tgaactatgt caaaggcaac ggctataaca atctgatcaa      2760
gattgatctg aatatggcaa cggtcaagca gttgtttgcg ttatccggct ttgagggcag      2820
catttacttc ttgaatccgg aaggtgccgt cctctattcc aacgactcca gcgtagacag      2880
gcattcacag acgcttccga tgccgaaaaa ctctctctcc tttgacaagg tttacacgaa      2940
caacaattat ttgaacgact ggtccctgca tggcgtcatt aacgaaggga gctttctgca      3000
tgacgtgcgg aaatcgggtt cctttgtcat tttttttggcg cttattaact ttgtgctgcc      3060
ttctttgatt atcgcggctc tctccagatc cataaacaaa cgtctcgtca agattgtaaa      3120
gcatatgaaa aaggtgaaaa accagcattt cgagacgatc ccgcttgatg atgcgcgcga      3180
tgagatcggc caattaacgg gtgaattcaa ccggatgacc gagcggatcg acaacctcat      3240
taccgatgtc tatcaggctg atattcagaa gaaggacctg gagatccgcc agcgccaggc      3300
acagcttcat gcccttcaca gccagatcaa tccccacttc ctgttcaact cgctcgagac      3360
gattcggatg cggagcctga tgaagggga gaccgagacc gcgaagacca ttcactatat      3420
ggcgaagatt ttccggaagt cgatttcctg gaaacgcagc tgggtgtcga tccgggaaga      3480
gattgagctg acggaatgct tccttgaaat tcagaaatac aggtttggcg acaagctgca      3540
ataccagatc accgtcgaag ataccgtata cgaccagatg attccgaaga tgaccttcct      3600
gccgttttgtc gagaacgcca gcattcatgg cattgaaagc tcgccgggaa tcggtcttat      3660
tcagattcat atcggaatcg ccggcaacaa gctgatgttc aggctgtccg ataacgggat      3720
```

```
cggcatgtcc caagccaagc tgtcggagct gcttaattac ctgcgtctgg atgattccat   3780
cggtgacaat gtcggcatga aaacgtcta tacccggctg aagctatgct ataaagactc    3840
gtttgaattc gacattgcta gcgaagaagg tcatggaaca accgttgagc tgcgtcttcc   3900
tctcgacatg aacgggcaat aaatgacaaa aaagttgaac tatgctttc aaagtacgaa    3960
ctaaagtttg aggggtaatc aagccttcgg attcgtttta tgatgaaagt gcttacaaca   4020
aacacgttga aatgacgaaa ggggtctaaa cagaaatggt taacaaaaag cttttaactg   4080
tcagcttggc tgctgctatg ttagctgtta cagcatccgc ttgcggcggc aataacgata   4140
acagcaatgc aaatagcggt aaatccggca atagcggcaa cgcagcttcc aactccgctt   4200
ctcctgaagc ggatgacaaa acacccgtca ctttctcgta ctacagcttc accagccaaa   4260
aggatgctct tgcgagcgac accgttatcg gtaaagagct gcaacagcag accggcgtag   4320
actggaaaat ggaattcctc gttggcgatc cgcaaacgaa atccggcgtt atgatcgcaa   4380
gcggcgacta tccggacgta atcgttccgg aaggcgaaat cgacaagctg cttgacgctg   4440
gcgcatttat tcctcttgat gatctgatcg agaaatacgg tccaaacatc aagcgcgtat   4500
acgtccctta ttttgataaa ttcagacaag cagacggcaa aatgtacttc ctgccgtttg   4560
gcgcgaacca aggctatatc ggcgatcccg gcatcagcca aggcgcattc tggatccaac   4620
gctccgttct gaaggaagcg ggatatccga agatcaagac gcttgaccag tacttcgatc   4680
tgatcaagca ataccaagag aagcatccgc aagtagacgg caaggacacg attggctttg   4740
catcccttgc aggtcctgcc gacagcttct tctcgatcac caacccttcc atgcaccttg   4800
cgggctaccc gaatgacggc gacgttatcg tcgacatgaa cacgcatgag gctaaaactt   4860
acgcagctac ggatatcgag aaaaaatggc tgcaaaagct gaacgaagta acgcggaag    4920
gcttgttcga tcctgagacc tttacagcga acaaagacca attcctggct aagctgacct   4980
ccggccgcgt acttggctac ttcaactacg catggcaggt tggcgacgcg acaaacaacc   5040
tgaagaaagc cggcatcgac gagaagcgtt acgctccgct gccaatcgta ttcgacgaga   5100
atacgaaaga ccaatacgta gatccgccta gctttgttaa caaccgcggt atcggtatct   5160
cggtaaaagc gaaagacgct gtacgcatta ttaagtactt cgacaacctt ctcaaagaag   5220
agaaccaagt tctcgtacag tggggcgtta agaccagaa ctacaccgtg gacgctaacg    5280
gccgttacgt gatggatgcg cagcaaatcg ctgaccgcaa cgaccctgag aagaaacgca   5340
cagtcggatg gcagtacttt gaatacagct ggccgcgtta cggcaacaac tccgtactgg   5400
ctgacggcaa ctcgtatggc gtaggcaacc agcctgaagt ggcttacgcg ggttacacgg   5460
acggcgacaa agcgctgctg gacgcctacg gcgtgaagac cttctccgaa tacttctcga   5520
agcctgacga tcgctcctgg tacccggcat ggagtatcaa caaggtcaa ggcacgcctg    5580
agcagatctt ccagcaaaaa gccggcgacc tgcaaaagaa attcgttccg aagcttgtac   5640
ttgccaagcc tagcgaattc gactcgatct ggagcgacta tacaggccaa atgggcaagc   5700
ttgacgtgaa aggctatgaa accttcgtta cgaaagtagt tcaagaccgt atcgcgggca   5760
agtggtaagc aaataaaagt agacggaagg ccggaaagct gattccggcc ttccgatcta   5820
ttggattcat gcaggatgct agagagggga agagcaagtg gagaacatac atgaagttac   5880
accatctgtt gtcaggagtc ccaaagcaag cgaatcacgg cttcaactgt ttttcaaaaa   5940
gttattgcag caaaaagtgc tcgtgtttat gtcgatgccg tttgtattat ggcttttcct   6000
gtttaagtac gtaccgctct ggggctggac catctccttt caaagttca gaccggcaaa    6060
ggatttgttc gatcaggagt gggtaggctg gaaaaacttg aacttcctgt ttaacgacga   6120
```

```
ctccttctat cgcgtgttaa gaaatacgat cgttatgagc tccatcaatc ttgtattagg    6180
ttttgttacc gcaatcgtat tggcgatttt attaaacgag cttcgccaaa ttatgttcaa    6240
gcgggtcgta cagacgatca gctacctacc gcattttatt tcctgggtcg ttgcggccaa    6300
tattatttct tcggcgcttg cgcccgaagg gatcgttaat attctattga cgagaatgca    6360
tctgattgat cagcctatct tatggctggg caaagggaat tacttctggg gcatccttgg    6420
cgcatcggaa gtttggaaaa acgtcggctg gaacaccatt atctatttgg cggctattac    6480
aaccattgac ccttcccaat acgaagctgc cgagattgac ggggcgaacc gtttacaacg    6540
gatcctgcat attactttac cgggtctgaa gtcggttatc gtaatcctgt tgatcatgaa    6600
ccttggaaat attctggaat cgggatttga gccgcaatac ttgctcggca acgggatgac    6660
cgtggactat tccgagaacc ttgatatatt tgtgttgaaa tacggcatga acatgggcaa    6720
ctattccttg gctacagcag ccggcatgtt caaaacggtc gttagcttta tcttcctctt    6780
atcggccaac tcgattgcga agcggcttgg cgagagcaga ctgttctaga tttaaccgaa    6840
agttggacga agcaaggagg ctatcgacat gaaagagagt tcggccaaag ccaggtacag    6900
ctctttaccg gataagattt ttgatacaag taatatagtt tttatgttgc tcgtcgtgac    6960
ggttacgcta tatcctttcc ttaatatgtt cgcgttgtcg ttcaacgatg cgaatgactc    7020
gatccgcggc ggcatttatg cttggccaag gatgtggaca tgggataact acagctatat    7080
ttttaatgaa gcatccatct atcacgctac gttgatctcc gccttgcgta cgattgccgg    7140
cacgattact tccgtcttct gtacggctat gctggcttat acgatcagcc gccaggagtt    7200
tgttctgcgc aaattcgtta cgctggtcgc aatcttcacg atgtacttca gcggaggtct    7260
cattccggga tacctgctga tcaaagagct ccatatgatt aactcgttct gggtttatat    7320
tatccccggc attatcggcg tctttaatat gatcgtaatc cgatccttta tcgagggatt    7380
gccggacggc attatggaat cggcgaaaat tgacggagcg ggcgaattca ttaccttcat    7440
gcgaattgtt ttgccgctga ccgtgcctgc tcttgcgacc gtttcgctct tcgtagcggt    7500
gtctcaatgg aattcctggt ttgacgtatt tctgtacaac tcttcgcatc ttaacctgag    7560
caccttgcaa tacgaattaa tgaaaatatt gcaaacctcc aatacggcgg catcgtcaac    7620
caatgcaggc gatcagtttg cagccggaca aagcggcgta acggcggtta cgccaacctc    7680
gatccgtgcg acgatgacta ttgttgcgag tctgccgatt attctggtat atccgttcct    7740
gcagaaatac tttgttaaag ggatgaccgt aggcggcgtt aaaggttaat cgcttgaatc    7800
acgcgtccct cgactttgca tcgggcggac gcttttttc taattttggc tgtttgtata    7860
acaattctta ttaggggat tagagatggg agacaacgga tacgcggcat ggctgagata    7920
cgatcaagtc aaggatgaaa cgcgcttgga gcaatacgca ggctggacgg gtgagctcgt    7980
gctgcccgcg ggagtaccga tggaagggat catgaagaca gccgccgtgg aattgtcgcg    8040
gggaatccgc tccatgctgg gcacaacgcc ttcggttacg catgaagcat cagggcagcg    8100
ttttatcgtg ctggaggttc ttggcggcgg ctcttggata gatcaagcgg ccggcgatgc    8160
ggcggctcta tctgatgagg gctacttctt aaaaaccgtt cgagaagcgg agaaggaata    8220
tattatcgcg gccggcaagt ccgagaaagc agtactgtac gcggtattcc atctgctgcg    8280
cctgatgcag tccgggactg cgattgatca gttaaatctg tcgagtcgc cgaaatacag    8340
ccttcgcatg attaaccatt gggataacat ggacggcagc gtggagcgcg ttactccgg    8400
ccgttcgatt ttttacgata caacaaagt gctgtccgat tcggaacgga ttcgcgatta    8460
cgcccgtctg atggcatcgg tcggaattaa tggcatcgcg attaataacg taaacgtcca    8520
```

```
ccgcgaagag acattcctta ttacggagaa gcttctgccg gatgttgtcc gtatcgccga    8580
ggtatttggc gaatacggca taaagctgtt cctgagcgtg aactatgccg gaaccattga    8640
gattggcggc ctggagacag ccgatcctct tgatccggcc gtgcgcggct ggtggaagga    8700
gaaggcggct gaagtgtacc gttatattcc ggactttggg ggcttccttg tgaaagccga    8760
ttccgagaat cgccccggtc cgtttaccta cggacgcgac catgcggacg gagctaacat    8820
gctggctgaa gcattggagc cgtttggcgg acttgtgctc tggcggtgct tcgtttacaa    8880
ctgccatcag gactggcggg atcgctcaac cgaccgtgcg cgtgccgctt acgatcactt    8940
taagccgctg gacggacgct tcaaggacaa tgtgattttg cagattaaga acggtccgat    9000
ggacttccag gtccgcgagc cggtctcgcc gctctttggc gcgatggagc ataccaacca    9060
gatgatggaa ttccagattg cccaggaata tacgggccag cagaaggatg tctgcttcct    9120
cattccgcag tggaaggaag tcttgaactt tgacacttac gtcaaaggtg cgggcagcac    9180
ggtgaaggag attgcggcag gcagcgtcca tgcctatact catagcggca ttacggccgt    9240
cagcaatatc ggcaacgacg agaactggac cgggcatcat ctcgcgcagg cgaatttgta    9300
cggctacgga cgcttaatct ggaatccgga gctttcttcg gaggagattg cggcggaatg    9360
ggctgcccaa acgtttggcg gcaataagaa cgtacaggat gttcttgtaa acttcctgct    9420
ggagtcgttg tccatttacg agaattatac agcgccgcta ggcgtaggct ggatggttac    9480
gcctcattat cactacggtc cggatattga cggctacgaa tattccaagt ggggaacata    9540
ccattttgcc gatcataagg gaattggggt tgaccgtacg gctcagacgg gtaccggcta    9600
cagcagccag tatgctttgc cgaacgccga ggtctacgac agcctggagg cttgtccgga    9660
tgagctgctg ctcttcttcc atcatgtgcc ttacacgcat cagttgaaat ccggcaagac    9720
ggttattcag catatttacg atacgcattt cgccggcgtg gagcgggttg aatattggat    9780
gaaccgctgg caggagcttg agggtctcgt ggacggcgac cggttccgcc atgtaacggg    9840
acgcatgaac tggcagcgtg aaaatgccaa gcaatggcgc gacatcgtta atacgtattt    9900
cttccgcaaa tccggtattc cggatacccca taaccgggtg atttactaat ctacaaggaa    9960
agagttggtg caggatatgt catatacttc ggagttgccg gcacttcgtt ccgttttataa    10020
ggattacttt gatattgggg cagctgtgaa tctgacgaca attgcatccc agaaggatgt    10080
tcttactgcc cattacaaca gtctgactgc cgaaaatgac atgaagttcg aacgcgtgca    10140
tccgcaggaa gggcagtata cgttcgaagc ggcggacaag atcgctgact ttgcggctgc    10200
aaacgccatg aagctgcgcg gcatacgct ggtgtgcac aatcagaccc ctgactggat    10260
attccaaaat gcgaatggat cgccagtcga tagggaaacg ctgcttgccc ggatgaaaag    10320
ccatatcgaa aaggttgttg gccggtataa aggcattatt tacggctggg atgttgtgaa    10380
cgaggttatc gacgataaaa acggtgtctg gcttagggag tccaaatggc taaacttagc    10440
cggggaagat tttatcgcaa aagccttcga gtatgcgcat gccgccgacc cgaaagcgct    10500
tctgttctac aatgattaca acgagtgcat tccggagaag cgggataaaa ttatccgtat    10560
cgttcaatcg ctgcaggcta agcaagtgcc gattcacggt atcggcctgc agggggcattg    10620
gaatttgaac ggtccaagtc ttgccgagat ccgggaagcc atcgaacgtt acgcggcaac    10680
gggtcttaag ctgcaggtaa cggagctgga tatttcggta ttcgatcatg acgataagcg    10740
gacggatctg acggagccta cggcagacat gctggagcgg caggcggaac gttacgggca    10800
ggtattcgag ctgttccgcg aatacaaaga ggcgattacc gccgttacgt tctggggcgc    10860
agccgacgat tacacctggc tggataactt cccggtacgc gggcggaaaa attggccgtt    10920
```

```
tgtgtttgat gccaaccacg agcctaaagc ttccttccgg aaaataaccg attggcagga   10980
agcggggcaa atcgattcat gacatacgca tcaacaggca aaatcacgta caggaacccg   11040
gtactgccgg gcttttatcc ggatccaagc gctgttcggg taggcgaaga ttattacatg   11100
gtgaccagca cctttgaata ttttccggga gttccggtgt ttcgcagcaa ggatctcgtt   11160
cattgggagc agattggtca tgtgttaacc agggaaagcc aagtgaatct gctgagccgc   11220
aacagctcgg agggcatcta tgcgcctgct cttcgttatc atgaaggcgt attttatatg   11280
attacaacgg atgtgtacgg gataggcaac ttctatgtaa ccgcaacgga tccggcagga   11340
ccatggtccg atccgattcg gattccttac ggcaatatcg atccttctct gttttttgac   11400
gatgacggca aagcgtacgt ctcggcgcag gccggctttg gcgagacgtc tcatattatc   11460
caatacgaga ttgatatcct gacgggcgag gccttatcgg agcctgttgt tgtatttgag   11520
ggagacgaag ggccttgggt agaagggccg catctgtaca aaataaacgg cttttattat   11580
atgatgaccg catccggcgg aacggggccg atgcacaggg agattatcgg ccgcggcacc   11640
tctccttacg gaccgtttga aatgctgccg catccgattc tgacgcataa cgagttacag   11700
gatcatccga ttcaatacac cggccatgtt gagctgctcg atgacgttcg tggccagtgg   11760
tgggcattgt ttcttggcgt ccggccgcaa ggcggcaacg gcagcgtgct tggccgcgag   11820
acgttccttg ctcccgtacg ctggagtgaa gacggctggc cgatgattga taataacgaa   11880
ggtcatgtat caatggttat ggagggaccg gctatccggg agagcaaaac ctccatggcc   11940
ggcatggaca gtcggtgac caccaagttc acttccgaag gcttagtctc gaatggatg    12000
tataaccggg tgatccccgg accggaggag ctgtctttaa cggagaagga aggctgcctt   12060
agactaagcg gcaatgccaa aggtcttcgc gacggaggag ctaatgtatt cgtatgccgc   12120
cgccagcagc atcatcggat gagcatcgag actcgcctga cctttgttcc gggaagagaa   12180
ggggagcagg caggaattgc cgcgcggctg agtgacaagt cccattactc gatcggaatc   12240
acgaagaagg acgacaaac cggcattctt gtaacggcga tggcgcaagg aagcggaacg   12300
gaagtcttta cccccaattga ggagcaggtt cccgtccggc tctcgatccg ttcggacgag   12360
aaggaatacg agcttttgta taccttggga ggtgcgtccg cggagtgggt cagcctaagg   12420
accttgccgg tggaagcctt aacgccggat gcggacggag cttttacggg cgtatgtctt   12480
ggcatgtttg cagcaggaac ggaggaaggc cattcggctc ccgcttatta cgattacttc   12540
gagtatcgtc ccgagagcgg ttgacacgcc aatgaagact atagcggtgc agagttccga   12600
tctctgcacc gttattttg tttatgcggc agctcctttt ttatggacag aatataggg     12660
gataaaaaac ttacaattac ttgcttgact tcagtaactg tatataatat tattacagta   12720
acaaagttg ttacagttaa tgagcgaaaa gagcatagga taggagtgga gttttggag    12780
cagaattata aaccgttatt tgaatccttt actttcccga gcggagtgga agtaaagaac   12840
cgcattgtga tggcgccgat gacgcactca tcctctaatg atgatggaac ggtaacggat   12900
gcggagctgg aatactatgc ccgccggtcc gagggagctg gcatggtcat aacggcatgt   12960
atttatgtca cgccaaacgg caaaggattt cccggggaat tcgcgggaga cagcgatgct   13020
atgattccgg ggcttgctcg tcttgcagag acgattaaag ccagaggcgc gaaagctatt   13080
ctccaaattt tccatggcgg ccgccgtgta ccgccggcat tggtgccaaa cggcgatgtg   13140
gttagcgcaa gcgccgttgc ggcgacggaa agcccggatg ttgttccgcg cgagctgaag   13200
cacgaagaga ttgaagcgat tatccgcgat tttggcgaga cgaccgccg cgcggcgctt   13260
gccggcttcg acggagtcga aattcacggc gcgaacactt atctcctgca gcagttctat   13320
```

```
tccccgcatt ccaaccgcag aaacgatcaa tggggcggag atatcgaccg gagacttaca    13380
ttcccgctcg ccgttgttga tgaagtgaaa cgcgccgcgg ctgagcatgc caaagggcca    13440
ttcttggtcg gataccgatt ctctccggaa gaaccggaga caccgggact tacgatggag    13500
gataccttcc gcctgttgga tgagcttgcg cagaaggatt tggattacct tcatgtctcg    13560
ttgtttgact tccgttccaa gccgtcgcgt ggtgcggatg atagcaaaac aagactggaa    13620
tgggtcgcgg agcgggtagc gggccgcgta ccggttatcg gcgtaggttc gattaactcg    13680
gccgacgatg ccattgaagc tcagcaaacg ggcattccgc tggttgcgat tggccgcgta    13740
ctgctgacgg atccggactg ggtacagaag gttgaaaccg gacgcgagga tgagattcag    13800
tcccgcttaa gcttaagctc gcagaagaag cttgtaattc ccgacggttt atggcgcatg    13860
ttgacggcaa gagaaggctg gctgccattt accgattaat ataaatgagg gctgacaatg    13920
aggcgccggg tgcgctgatt gtcagccctt tttgttttgc ataaaatatg cggcaaaggt    13980
atactcgaat ccataagagc ataattggag gccaagtaat gacctttgat gaagttttgc    14040
gggcgttaga gggaatggga agcgagcaga ccaagagcac ctatgtgcgt catggtgcga    14100
aggagccttt ttttggcgta aagatcggcg atatgaagaa gctggtcaaa gaggtgaaga    14160
aagaccagga gctggtgtac aagctttacg attccggcaa tcatgatgcc atgtatttgg    14220
caggactgac cgttaatccg aaaacggtca ccaaagagat gctccggcat ggggtgaagc    14280
aggcttattg gtattcgctt gcggaatata cggtagcgaa tgtaacggcg gagagtcctt    14340
ttgcacggga gcttgcggta gaatggatgc agtcgccgga agagatggtt gcggtagcgg    14400
gatggagcgc ctatgcgaat tacgtgacga tcgctccgga tgaagaactc gatttgatgg    14460
agatccgaag gcttctggag caggttaaga agaccgtcca tgaagagcgg aaccgcgtgc    14520
ggtatacgat gaatacgttt gtcatctgcg ttgcgtctta cgtcttgccc ctgacggagg    14580
aagcaaaagc cgttgcggag gcgattggcg ccgtaaaagt cgatgttggc gataccgcct    14640
gcaaagttcc gctcgcctcc ggctatatcg ccaaggtaga agcaagagga aagatcggca    14700
cgaagaagaa aacttgtatt tgttgattaa aaaggctgct ccaccagacg atggagcagc    14760
ctttcgttct ttcgtttatc ccgcagcttg ctgcagggat gcttttcgg ctgaacgatc    14820 gagattatag ctataggccg ttgcggcaaa agcaagcaag gcgagtacgg ccgctgccca    14880
cggaagataa cgcagaccat aatgatcggt tacgaaggcg ccgaccgagg agccaaccgc    14940
aatcccgata ttggcgctga tcggaagcag ggaagaggcg aaatccttgg cttcgggcac    15000
atattgctcg gtcagatgga tgaagtacag ctggcaagcc gcattgatcg agaatgaaat    15060
gagagcaata gccatcaagc tgacgatgcc aagccaagtg aacgataagg taaaaccaaa    15120
aatgacgtaa acaacggcat ggaccaggaa cagcgttttc agcttcgcca tgtaagtgcc    15180
gcttgcgatt ttgccgccta gtatgttgct gacgattgtc acggctccgt atacgagcag    15240
gatggtgctg gttcggcctt ccgagatatg cataac                              15276
```

<210> SEQ ID NO 22
<211> LENGTH: 34
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (29)..(29)
<223> OTHER INFORMATION: n is a, c, g, or t

<400> SEQUENCE: 22

```
gcattaatgc aatttcaatt aataaygtna aygt                          34
```

<210> SEQ ID NO 23
<211> LENGTH: 33
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (31)..(31)
<223> OTHER INFORMATION: n is a, c, g, or t

<400> SEQUENCE: 23

```
cagatgtttt tgttggcctg trtaytcytg ngt                           33
```

<210> SEQ ID NO 24
<211> LENGTH: 25
<212> TYPE: DNA
<213> ORGANISM: Artificial sequence
<220> FEATURE:
<223> OTHER INFORMATION: Primer

<400> SEQUENCE: 24

```
cgagagacat tccttattac ggaga                                    25
```

<210> SEQ ID NO 25
<211> LENGTH: 23
<212> TYPE: DNA
<213> ORGANISM: Artificial sequence
<220> FEATURE:
<223> OTHER INFORMATION: Primer

<400> SEQUENCE: 25

```
catctggttg gtatgctcca tcg                                      23
```

<210> SEQ ID NO 26
<211> LENGTH: 24
<212> TYPE: DNA
<213> ORGANISM: Artificial sequence
<220> FEATURE:
<223> OTHER INFORMATION: Primer

<400> SEQUENCE: 26

```
ggccatggga gacaacggat acgc                                     24
```

<210> SEQ ID NO 27
<211> LENGTH: 27
<212> TYPE: DNA
<213> ORGANISM: Artificial sequence
<220> FEATURE:
<223> OTHER INFORMATION: Primer

<400> SEQUENCE: 27

```
cacctcgagt gaatcgattt gccccgc                                  27
```

<210> SEQ ID NO 28
<211> LENGTH: 28
<212> TYPE: DNA
<213> ORGANISM: Artificial sequence
<220> FEATURE:
<223> OTHER INFORMATION: Primer

<400> SEQUENCE: 28

```
cggacatgtc atatacttcg gagttgcc                                 28
```

<210> SEQ ID NO 29

```
<211> LENGTH: 27
<212> TYPE: DNA
<213> ORGANISM: Artificial sequence
<220> FEATURE:
<223> OTHER INFORMATION: Primer

<400> SEQUENCE: 29
cacctcgagt gaatcgattt gccccgc                                            27

<210> SEQ ID NO 30
<211> LENGTH: 25
<212> TYPE: DNA
<213> ORGANISM: Artificial sequence
<220> FEATURE:
<223> OTHER INFORMATION: PF54 primer

<400> SEQUENCE: 30
cgagagagag acattcctta ttacg                                              25

<210> SEQ ID NO 31
<211> LENGTH: 23
<212> TYPE: DNA
<213> ORGANISM: Artificial sequence
<220> FEATURE:
<223> OTHER INFORMATION: PR569 primer

<400> SEQUENCE: 31
catctggttg gtatgctcca tcg                                                23

<210> SEQ ID NO 32
<211> LENGTH: 22
<212> TYPE: DNA
<213> ORGANISM: Artificial sequence
<220> FEATURE:
<223> OTHER INFORMATION: rre178f primer

<400> SEQUENCE: 32
gtgctggacg gattggagct ta                                                 22

<210> SEQ ID NO 33
<211> LENGTH: 22
<212> TYPE: DNA
<213> ORGANISM: Artificial sequence
<220> FEATURE:
<223> OTHER INFORMATION: rre459r primer

<400> SEQUENCE: 33
ctccgagaac tggccttgaa ca                                                 22

<210> SEQ ID NO 34
<211> LENGTH: 22
<212> TYPE: DNA
<213> ORGANISM: Artificial sequence
<220> FEATURE:
<223> OTHER INFORMATION: sbp1081f primer

<400> SEQUENCE: 34
aactcgtatg gcgtaggcaa cc                                                 22

<210> SEQ ID NO 35
<211> LENGTH: 22
<212> TYPE: DNA
<213> ORGANISM: Artificial sequence
<220> FEATURE:
<223> OTHER INFORMATION: sbp1361r primer

<400> SEQUENCE: 35
```
tggcctgtat agtcgctcca ga                                    22

<210> SEQ ID NO 36
<211> LENGTH: 22
<212> TYPE: DNA
<213> ORGANISM: Artificial sequence
<220> FEATURE:
<223> OTHER INFORMATION: agua1069f primer

<400> SEQUENCE: 36
cggacgcttc aaggacaatg tg                                    22

<210> SEQ ID NO 37
<211> LENGTH: 22
<212> TYPE: DNA
<213> ORGANISM: Artificial sequence
<220> FEATURE:
<223> OTHER INFORMATION: agua1354r primer

<400> SEQUENCE: 37
ggccgtaatg ccgctatgag ta                                    22

<210> SEQ ID NO 38
<211> LENGTH: 22
<212> TYPE: DNA
<213> ORGANISM: Artificial sequence
<220> FEATURE:
<223> OTHER INFORMATION: xyl247f primer

<400> SEQUENCE: 38
catacgctgg tgtggcacaa tc                                    22

<210> SEQ ID NO 39
<211> LENGTH: 22
<212> TYPE: DNA
<213> ORGANISM: Artificial sequence
<220> FEATURE:
<223> OTHER INFORMATION: xyl623r primer

<400> SEQUENCE: 39
ccgtgaatcg gcacttgctt ag                                    22

<210> SEQ ID NO 40
<211> LENGTH: 22
<212> TYPE: DNA
<213> ORGANISM: Artificial sequence
<220> FEATURE:
<223> OTHER INFORMATION: bex948f primer

<400> SEQUENCE: 40
ggacaagtcg gtgaccacca ag                                    22

<210> SEQ ID NO 41
<211> LENGTH: 22
<212> TYPE: DNA
<213> ORGANISM: Artificial sequence
<220> FEATURE:
<223> OTHER INFORMATION: bex1291r primer

<400> SEQUENCE: 41
cttgcgccat cgccgttaca ag                                    22

<210> SEQ ID NO 42
<211> LENGTH: 22
<212> TYPE: DNA
<213> ORGANISM: Artificial sequence
<220> FEATURE:

```
<223> OTHER INFORMATION: xynA1-2237f primer

<400> SEQUENCE: 42
gcgtcggaat gcaaggccat ta                                              22

<210> SEQ ID NO 43
<211> LENGTH: 22
<212> TYPE: DNA
<213> ORGANISM: Artificial sequence
<220> FEATURE:
<223> OTHER INFORMATION: xynA1-2503r primer

<400> SEQUENCE: 43
tctcggctct ccagcttgtg tt                                              22

<210> SEQ ID NO 44
<211> LENGTH: 22
<212> TYPE: DNA
<213> ORGANISM: Artificial sequence
<220> FEATURE:
<223> OTHER INFORMATION: amp10f primer

<400> SEQUENCE: 44
gatctggcag cttcctgcat tc                                              22

<210> SEQ ID NO 45
<211> LENGTH: 22
<212> TYPE: DNA
<213> ORGANISM: Artificial sequence
<220> FEATURE:
<223> OTHER INFORMATION: amp204r primer

<400> SEQUENCE: 45
tccagtccgc ggctcttatc aa                                              22

<210> SEQ ID NO 46
<211> LENGTH: 22
<212> TYPE: DNA
<213> ORGANISM: Artificial sequence
<220> FEATURE:
<223> OTHER INFORMATION: oxr535f

<400> SEQUENCE: 46
tcacggcgcg aacacttatc tc                                              22

<210> SEQ ID NO 47
<211> LENGTH: 22
<212> TYPE: DNA
<213> ORGANISM: Artificial sequence
<220> FEATURE:
<223> OTHER INFORMATION: oxr774r primer

<400> SEQUENCE: 47
gctcatcaca ggcggaaggt at                                              22

<210> SEQ ID NO 48
<211> LENGTH: 22
<212> TYPE: DNA
<213> ORGANISM: Artificial sequence
<220> FEATURE:
<223> OTHER INFORMATION: perm-agua791f primer

<400> SEQUENCE: 48
taacggcggt tacgccaacc tc                                              22

<210> SEQ ID NO 49
```

```
<211> LENGTH: 22
<212> TYPE: DNA
<213> ORGANISM: Artificial sequence
<220> FEATURE:
<223> OTHER INFORMATION: perm-agua81r primer

<400> SEQUENCE: 49
ccagcctgcg tattgctcca ag                                              22

<210> SEQ ID NO 50
<211> LENGTH: 14
<212> TYPE: DNA
<213> ORGANISM: Artificial sequence
<220> FEATURE:
<223> OTHER INFORMATION: Candidate CcpA binding sites
<220> FEATURE:
<221> NAME/KEY: misc_feature
<222> LOCATION: (3)..(3)
<223> OTHER INFORMATION: w = a or t/u
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (12)..(12)
<223> OTHER INFORMATION: w = a or t/u

<400> SEQUENCE: 50
tgwaancgnt nwca                                                       14

<210> SEQ ID NO 51
<211> LENGTH: 14
<212> TYPE: DNA
<213> ORGANISM: Artificial sequence
<220> FEATURE:
<223> OTHER INFORMATION: Candidate CcpA binding sites

<400> SEQUENCE: 51
tgaaatcgct taca                                                       14

<210> SEQ ID NO 52
<211> LENGTH: 14
<212> TYPE: DNA
<213> ORGANISM: Artificial sequence
<220> FEATURE:
<223> OTHER INFORMATION: Candidate CcpA binding sites

<400> SEQUENCE: 52
tgaaagtgct taca                                                       14

<210> SEQ ID NO 53
<211> LENGTH: 14
<212> TYPE: DNA
<213> ORGANISM: Artificial sequence
<220> FEATURE:
<223> OTHER INFORMATION: Candidate CcpA binding sites

<400> SEQUENCE: 53
tgaagcggat gaca                                                       14

<210> SEQ ID NO 54
```

```
<211> LENGTH: 14
<212> TYPE: DNA
<213> ORGANISM: Artificial sequence
<220> FEATURE:
<223> OTHER INFORMATION: Candidate CcpA binding sites

<400> SEQUENCE: 54
tgaaccgctg gcag                                                        14

<210> SEQ ID NO 55
<211> LENGTH: 14
<212> TYPE: DNA
<213> ORGANISM: Artificial sequence
<220> FEATURE:
<223> OTHER INFORMATION: Candidate CcpA binding sites

<400> SEQUENCE: 55
tgtaagcgct taat                                                        14
```